(12) United States Patent
Rebar

(10) Patent No.: US 9,394,545 B2
(45) Date of Patent: Jul. 19, 2016

(54) METHODS AND COMPOSITIONS FOR REGULATION OF TRANSGENE EXPRESSION

(71) Applicant: Sangamo BioSciences, Inc., Richmond, CA (US)

(72) Inventor: Edward J. Rebar, San Francisco, CA (US)

(73) Assignee: Sangamo BioSciences, Inc., Richmond, CA (US)

(*) Notice: Subject to any disclaimer, the term of this patent is extended or adjusted under 35 U.S.C. 154(b) by 505 days.

(21) Appl. No.: 13/624,193

(22) Filed: Sep. 21, 2012

(65) Prior Publication Data

US 2013/0177983 A1     Jul. 11, 2013

Related U.S. Application Data

(60) Provisional application No. 61/537,349, filed on Sep. 21, 2011, provisional application No. 61/560,506, filed on Nov. 16, 2011, provisional application No. 61/670,490, filed on Jul. 11, 2012.

(51) Int. Cl.
| | | |
|---|---|---|
| C12N 15/00 | (2006.01) |
| C12N 5/00 | (2006.01) |
| C12N 15/62 | (2006.01) |
| C12N 15/85 | (2006.01) |
| C12N 9/96 | (2006.01) |
| C07K 14/00 | (2006.01) |
| C12N 9/22 | (2006.01) |

(52) U.S. Cl.
CPC ............. *C12N 15/62* (2013.01); *C07K 14/00* (2013.01); *C12N 9/22* (2013.01); *C12N 9/96* (2013.01); *C12N 15/85* (2013.01); *C07K 2319/81* (2013.01); *C12N 2799/025* (2013.01)

(58) Field of Classification Search
None
See application file for complete search history.

(56) References Cited

U.S. PATENT DOCUMENTS

| | | | |
|---|---|---|---|
| 5,789,538 A | 8/1998 | Rebar et al. |
| 5,925,523 A | 7/1999 | Dove et al. |
| 6,007,988 A | 12/1999 | Choo et al. |
| 6,013,453 A | 1/2000 | Choo et al. |
| 6,140,081 A | 10/2000 | Barbas et al. |
| 6,140,466 A | 10/2000 | Barbas et al. |
| 6,200,759 B1 | 3/2001 | Dove et al. |
| 6,242,568 B1 | 6/2001 | Barbas et al. |
| 6,410,248 B1 | 6/2002 | Greisman et al. |
| 6,453,242 B1 | 9/2002 | Eisenberg et al. |
| 6,479,626 B1 | 11/2002 | Kim et al. |
| 6,503,717 B2 | 1/2003 | Case et al. |
| 6,534,261 B1 | 3/2003 | Cox, III et al. |
| 6,599,692 B1 | 7/2003 | Case et al. |
| 6,607,882 B1 | 8/2003 | Cox, III et al. |
| 6,689,558 B2 | 2/2004 | Case |
| 6,723,551 B2 | 4/2004 | Kotin et al. |
| 6,794,136 B1 | 9/2004 | Eisenberg et al. |
| 6,824,978 B1 | 11/2004 | Cox, III et al. |
| 6,903,185 B2 | 6/2005 | Kim et al. |
| 6,933,113 B2 | 8/2005 | Case et al. |
| 6,979,539 B2 | 12/2005 | Cox, III et al. |
| 7,013,219 B2 | 3/2006 | Case et al. |
| 7,030,215 B2 | 4/2006 | Liu et al. |
| 7,067,317 B2 | 6/2006 | Rebar et al. |
| 7,070,934 B2 | 7/2006 | Cox, III et al. |
| 7,153,949 B2 | 12/2006 | Kim et al. |
| 7,163,824 B2 | 1/2007 | Cox, III et al. |
| 7,253,273 B2 | 8/2007 | Collingwood |
| 7,262,054 B2 | 8/2007 | Jamieson et al. |
| 7,361,635 B2 | 4/2008 | Miller et al. |
| 7,888,121 B2 | 2/2011 | Urnov et al. |
| 2001/0051611 A1 | 12/2001 | Srivastava et al. |
| 2003/0232410 A1 | 12/2003 | Liljedahl et al. |
| 2005/0026157 A1 | 2/2005 | Baltimore et al. |
| 2005/0064474 A1 | 3/2005 | Urnov et al. |
| 2005/0208489 A1 | 9/2005 | Carroll et al. |
| 2005/0267061 A1 | 12/2005 | Martin |
| 2006/0063231 A1 | 3/2006 | Li et al. |
| 2006/0188987 A1 | 8/2006 | Guschin et al. |
| 2007/0218528 A1 | 9/2007 | Miller |
| 2008/0131962 A1 | 6/2008 | Miller et al. |
| 2008/0159996 A1 | 7/2008 | Ando et al. |
| 2008/0299580 A1 | 12/2008 | DeKelver et al. |
| 2009/0069259 A1 | 3/2009 | Collingwood |
| 2009/0098134 A1 | 4/2009 | Buelow |
| 2009/0305419 A1 | 12/2009 | Miller |
| 2010/0047805 A1 | 2/2010 | Wang |
| 2010/0218264 A1 | 8/2010 | Cui et al. |
| 2011/0023158 A1 | 1/2011 | Bedell et al. |
| 2011/0041195 A1 | 2/2011 | Doyon |

(Continued)

FOREIGN PATENT DOCUMENTS

| | | |
|---|---|---|
| GB | 2338237 | 6/2011 |
| WO | WO 95/19431 | 7/1995 |

(Continued)

OTHER PUBLICATIONS

Beerli, et al., "Engineering Polydactyl Zinc-Finger Transcription Factors," *Nature Biotechnol* 20:135-141 (2002).
Boch, et al., "Breaking the Code of DNA Binding Specificity of TAL-Type III Effectors," *Science* 326:1509-1512 (2002).
Bonas, et al., "Genetic and Structural Characterization of the Avirulence Gene AVRBS3 From Xanthomonas Campestris PV. Vesicatoria," *Mol Gen Genet* 218:127-136 (1989).
Choo, et al., "Advances in Zinc Finger Engineering," *Curr Opin Struct Biol* 10:411-416 (2000).

(Continued)

*Primary Examiner* — Richard Hutson
(74) *Attorney, Agent, or Firm* — Pasternak Patent Law; Susan Abrahamson

(57) ABSTRACT

Nucleases and methods of using these nucleases for expressing a transgene from a safe harbor locus in a secretory tissue, and clones and animals derived therefrom.

5 Claims, 20 Drawing Sheets

(56) References Cited

U.S. PATENT DOCUMENTS

| | | |
|---|---|---|
| 2011/0145940 A1 | 6/2011 | Voytas et al. |
| 2011/0201055 A1 | 8/2011 | Doyon |
| 2011/0207221 A1 | 8/2011 | Cost et al. |
| 2011/0301073 A1 | 12/2011 | Gregory et al. |
| 2012/0128635 A1 | 5/2012 | Gregory et al. |

FOREIGN PATENT DOCUMENTS

| | | |
|---|---|---|
| WO | WO 96/06166 | 2/1996 |
| WO | WO 98/37186 | 8/1998 |
| WO | WO 98/53057 | 11/1998 |
| WO | WO 98/53058 | 11/1998 |
| WO | WO 98/53059 | 11/1998 |
| WO | WO 98/53060 | 11/1998 |
| WO | WO 98/54311 | 12/1998 |
| WO | WO 00/27878 | 5/2000 |
| WO | WO 01/60970 | 8/2001 |
| WO | WO 01/88197 | 11/2001 |
| WO | 0208286 A2 | 1/2002 |
| WO | WO 02/16536 | 2/2002 |
| WO | WO 02/099084 | 12/2002 |
| WO | WO 03/016496 | 2/2003 |
| WO | WO 2007/014275 | 2/2007 |
| WO | 2008021207 A2 | 2/2008 |
| WO | WO 2010/079430 | 7/2010 |
| WO | WO 02/077227 | 10/2010 |

OTHER PUBLICATIONS

Guschin, et al., "A Rapid and General Assay for Monitoring Endogenous Gene Modification," *Methods Mol Biol* 649:247-256 (2010).

Heuer, et al., "Repeat Domain Diversity of AVRBS3-Like Genes in Ralstonia Solanacearum Strains and Association With Host Preferences in the Field," *Appl and Envir Micro* 73(13):4379-4384 (2007).

Isalan, et al., "A Rapid, Generally Applicable Method to Engineer Zinc Fingers Illustrated by Targeting the HIV-1 Promoter.," *Nature Biotechnol* 19:656-660 (2001).

Kay, et al., "A Bacterial Effector Acts as a Plant Transcription Factor and Induces a Cell Size Regulator," *Science* 318:648-351 (2007).

Kim, et al., "Hybrid Restriction Enzymes: Zinc Finger Fusions to FOK I Cleavage Domain," *Proc Nat'l Acad Sci USA* 93:1156-1160 (1996).

Li, et al., "In Vivo Genome Editing Restores Haemostasis in a Mouse Model of Haemophilia," *Nature* 475:217-221 (2011).

Minghetti, et al., "Molecular Structure of the Human Albumin Gene Is Revealed by Nucleotide Sequence Within Q11-22 of Chromosome 4*," *J. Biol. Chem* 261:6747-6757 (1986).

Moscou, et al., "A Simple Cipher Governs DNA Recognition by TAL Effectors," *Science* 326:1501 (2009).

Osborn, et al., "Pharmacokinetic and Pharmacodynamic Studies of a Human Serum Albumin-Interferon-Alpha Fusion Protein in Cynomolgus Monkeys," *J Pharm Exp Thera* 303(2):540-548 (2002).

Pabo, et al., "Design and Selection of Novel CYS2HIS2 Zinc Finger Proteins.," *Annu Rev Biochem* 70:313-340 (2001).

Perez, et al., "Establishment of HIV-1 Resistance in CD4+ T Cells by Genome Editing Using Zinc-Finger Nucleases," *Nature Biotechnology* 26:808-816 (2008).

Schornack, et al., "Gene-For-Gene-Mediated Recognition of Nuclear-Targeted AVRBS3-Like Bacterial Effector Proteins," *J Plant Physiol* 163(3):256-272 (2006).

Segal, et al., "Custom DNA-Binding Proteins Come of Age: Polydactyl Zinc-Finger Proteins," *Curr Opin Biotechnol* 12:632-637 (2001).

Urnov, et al., "Highly Efficient Endogenous Human Gene Correction Using Designed Zinc-Finger Nucleases," *Nature* 435:646-651 (2005).

Watkins, et al., "Analbuminemia: Three Cases Resulting From Different Point Mutations in the Albumin Gene," *Proc Natl Acad Sci USA* 91:9417-9421 (1994).

Yang, et al., "Purification, Cloning, and Characterization of the CEL I Nuclease," *Biochemistry* 39:3533-3541 (2000).

Hockemeyer, et al., "Efficient Targeting of Expressed and Silent Genes in Human ESCS and IPSCS Using Zinc-Finger Nucleases," Nature Biotechnology 27(9):851-857 (2009) doi:10.1038/nbt.1562.

Maeder, et al., "Rapid Open-Source Engineering of Customized Zinc-Finger Nucleases for Highly Efficient Gene Modification," Molecular Cell 31:294-301 (2008).

Sander, et al., "Zinc Finger Targeter (ZIFIT): An Energized Zinc Finger/Target Site Design Tool," Nucleic Acids Research 35:W599-W605 (2007).

Watkins, et al., "Analbuminiemia: Three Cases Resulting From Different Point Mutations in the Albumin Gene," PNAS USA 91:9417-9421 (1994).

Wright, et al., "Standardized Reagents and Protocols for Engineering Zinc Finger Nucleases by Modular Assembly," Nature Protocols 1(3):1637-1652 (2006).

Zou, et al., "Oxidase-Deficient Neutrophils From X-Linked Chronic Granulomatous Disease IPS Cells: Functional Correction by Zinc Finger Nuclease-Mediated Safe Harbor Targeting," Blood 117:5561-5572 (2011).

Anguela, et al., "In Vivo Genome Editing of Liver Albumin for Therapeutic Gene Expression: Rescue of Hemophilic Mice Via Integration of Factor 9," 54th ASH Annual Meeting and Exposition Atlanta, GA, Dec. 10, 2012.

Carroll, "Genome Engineering With Zinc-Finger Nucleases," Genetics188:773-782 (2011).

Kim, et al., "Targeted Genome Editing in Human Cells With Zinc Finger Nucleases Constructed via Modular Assembly" Genome Research 19:1279-1288 (2009).

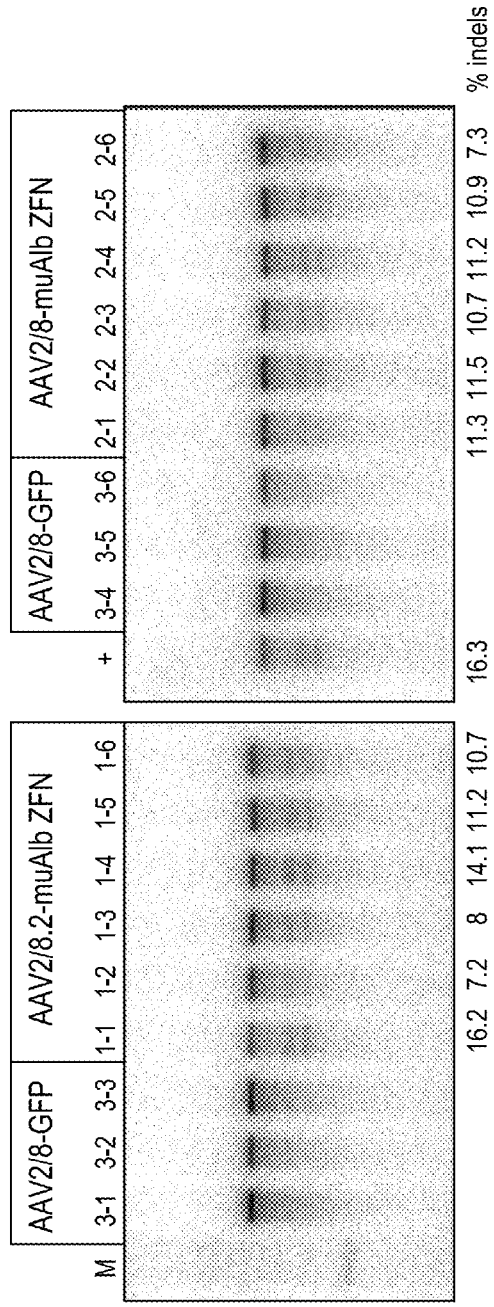
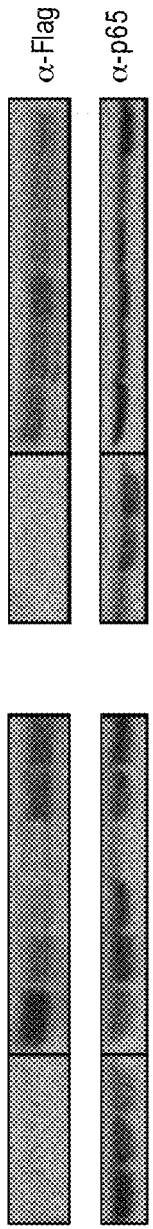
FIG. 5A
FIG. 5B

HUMAN ALBUMIN, EXON 1/INTRON 1 BORDER REGION

```
     EXON 1       INTRON 1
1141 GTCGAGATGCAC|GTAAGAAA TCCATTTTTC TATTGTTCAA CTTTTATTCT ATTTTCCCAG

1201 TAAAATAAAG TTTTAGTAAA CTCTGCATCT TTAAAGAATT ATTTTGGCAT TTATTTCTAA

1261 AATGGCATAG TATTTTGTAT TTGTGAAGTC TTACAAGGTT ATCTTATTAA TAAAATTCAA

1321 ACATCCTAGG TAAAAAAAAA AAAAGGTCAG AATTGTTTAG TGACTGTAAT TTTCTTTTGC

1381 GCACTAAGGA AAGTGCAAAG TAACTTAGAG TGACTGAAAC TTCACAGAAT AGGGTTGAAG
                                                        35426, 35428
             35361, 35364, 35370, 35379                  ─────────────
                                   35393, 35394, 35396, 35398, 35399, 35405

1441 ATTGAATTCA TAACTATCCC AAAGACCTAT CCATTGCACT ATGCTTTATT TAAAAACCAC
                ────────────────
                35458, 35480

1501 AAAACCTGTG CTGTTGATCT CATAAATAGA ACTTGTATTT ATATTTATTT TCATTTTAGT

2101 ATGGCTATTG AGTACTTCAA ATATGACAAG TGCAACTGAG AAACAAAAAC TTAAATTGTA
```

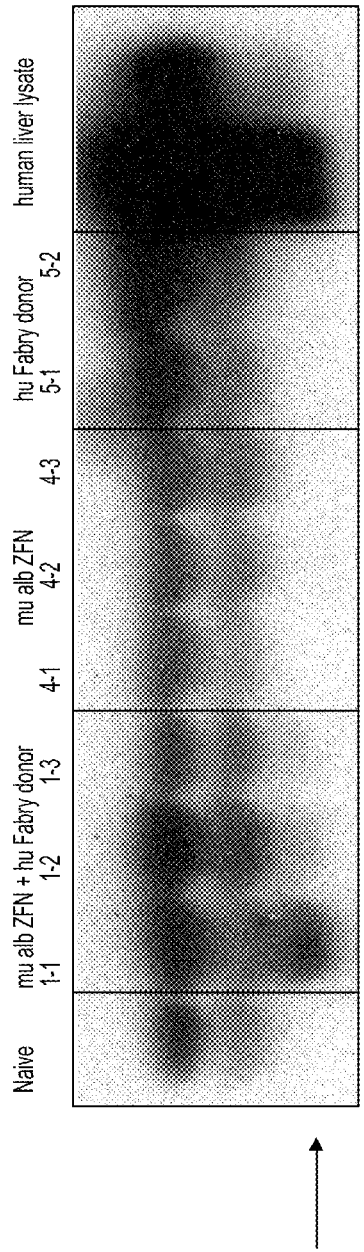
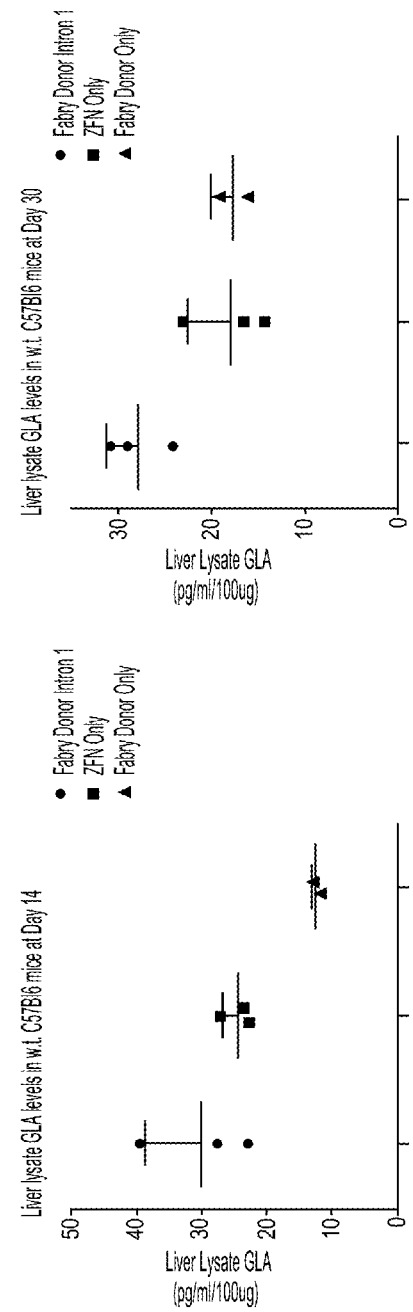
FIG. 13A
FIG. 13B

METHODS AND COMPOSITIONS FOR REGULATION OF TRANSGENE EXPRESSION

CROSS-REFERENCE TO RELATED APPLICATIONS

The present application claims the benefit of U.S. Provisional Application Nos. 61/537,349 filed Sep. 21, 2011; U.S. Provisional Application 61/560,506 filed Nov. 16, 2011; and U.S. Provisional Application 61/670,490 filed Jul. 11, 2012, the disclosures of which are hereby incorporated by reference in its entirety.

TECHNICAL FIELD

The present disclosure is in the field of genome editing.

BACKGROUND

Gene therapy holds enormous potential for a new era of human therapeutics. These methodologies will allow treatment for conditions that have not been addressable by standard medical practice. Gene therapy can include the many variations of genome editing techniques such as disruption or correction of a gene locus, and insertion of an expressible transgene that can be controlled either by a specific exogenous promoter fused to the transgene, or by the endogenous promoter found at the site of insertion into the genome.

Delivery and insertion of the transgene are examples of hurdles that must be solved for any real implementation of this technology. For example, although a variety of gene delivery methods are potentially available for therapeutic use, all involve substantial tradeoffs between safety, durability and level of expression. Methods that provide the transgene as an episome (e.g. basic adenovirus, AAV and plasmid-based systems) are generally safe and can yield high initial expression levels, however, these methods lack robust episome replication, which may limit the duration of expression in mitotically active tissues. In contrast, delivery methods that result in the random integration of the desired transgene (e.g. integrating lentivirus) provide more durable expression but, due to the untargeted nature of the random insertion, may provoke unregulated growth in the recipient cells, potentially leading to malignancy via activation of oncogenes in the vicinity of the randomly integrated transgene cassette. Moreover, although transgene integration avoids replication-driven loss, it does not prevent eventual silencing of the exogenous promoter fused to the transgene. Over time, such silencing results in reduced transgene expression for the majority of random insertion events. In addition, integration of a transgene rarely occurs in every target cell, which can make it difficult to achieve a high enough expression level of the transgene of interest to achieve the desired therapeutic effect.

In recent years, a new strategy for transgene integration has been developed that uses cleavage with site-specific nucleases to bias insertion into a chosen genomic locus (see, e.g., co-owned U.S. Pat. No. 7,888,121). This approach offers the prospect of improved transgene expression, increased safety and expressional durability, as compared to classic integration approaches, since it allows exact transgene positioning for a minimal risk of gene silencing or activation of nearby oncogenes.

One approach involves the integration of a transgene into its cognate locus, for example, insertion of a wild type transgene into the endogenous locus to correct a mutant gene. Alternatively, the transgene may be inserted into a non-cognate locus chosen specifically for its beneficial properties. See, e.g., U.S. Patent Publication No. 20120128635 relating to targeted insertion of a factor IX (FIX) transgene. Targeting the cognate locus can be useful if one wishes to replace expression of the endogenous gene with the transgene while still maintaining the expressional control exerted by the endogenous regulatory elements. Specific nucleases can be used that cleave within or near the endogenous locus and the transgene can be integrated at the site of cleavage through homology directed repair (HDR) or by end capture during non-homologous end joining (NHEJ). The integration process is determined by the use or non-use of regions of homology in the transgene donors between the donor and the endogenous locus.

Alternatively, the transgene may be inserted into a specific "safe harbor" location in the genome that may either utilize the promoter found at that safe harbor locus, or allow the expressional regulation of the transgene by an exogenous promoter that is fused to the transgene prior to insertion. Several such "safe harbor" loci have been described, including the AAVS1 and CCR5 genes in human cells, and Rosa26 in murine cells (see, e.g., co-owned United States patent applications nos. 20080299580; 20080159996 and 201000218264). As described above, nucleases specific for the safe harbor can be utilized such that the transgene construct is inserted by either HDR- or NHEJ-driven processes.

An especially attractive application of gene therapy involves the treatment of disorders that are either caused by an insufficiency of a secreted gene product or that are treatable by secretion of a therapeutic protein. Such disorders are potentially addressable via delivery of a therapeutic transgene to a modest number of cells, provided that each recipient cell expresses a high level of the therapeutic gene product. In such a scenario, relief from the need for gene delivery to a large number of cells can enable the successful development of gene therapies for otherwise intractable indications. Such applications would require permanent, safe, and very high levels of transgene expression. Thus the development of a safe harbor which exhibits these properties would provide substantial utility in the field of gene therapy.

A considerable number of disorders are either caused by an insufficiency of a secreted gene product or are treatable by secretion of a therapeutic protein. Clotting disorders, for example, are fairly common genetic disorders where factors in the clotting cascade are aberrant in some manner, i.e., lack of expression or production of a mutant protein. Most clotting disorders result in hemophilias such as hemophilia A (factor VIII deficiency), hemophilia B (factor IX deficiency), or hemophilia C (factor XI deficiency). Treatment for these disorders is often related to the severity. For mild hemophilias, treatments can involve therapeutics designed to increase expression of the under-expressed factor, while for more severe hemophilias, therapy involves regular infusion of the missing clotting factor (often 2-3 times a week) to prevent bleeding episodes. Patients with severe hemophilia are often discouraged from participating in many types of sports and must take extra precautions to avoid everyday injuries.

Alpha-1 antitrypsin (A1AT) deficiency is an autosomal recessive disease caused by defective production of alpha 1-antitrypsin which leads to inadequate A1AT levels in the blood and lungs. It can be associated with the development of chronic obstructive pulmonary disease (COPD) and liver disorders. Currently, treatment of the diseases associated with this deficiency can involve infusion of exogenous A1AT and lung or liver transplant.

Lysosomal storage diseases (LSDs) are a group of rare metabolic monogenic diseases characterized by the lack of functional individual lysosomal proteins normally involved in the breakdown of waste lipids, glycoproteins and mucopolysaccharides. These diseases are characterized by a buildup of these compounds in the cell since it is unable to process them for recycling due to the mis-functioning of a specific enzyme. Common examples include Gaucher's (glucocerebrosidase deficiency-gene name: GBA), Fabry's (α galactosidase deficiency—GLA), Hunter's (iduronate-2-sulfatase deficiency—IDS), Hurler's (alpha-L iduronidase deficiency—IDUA), and Niemann-Pick's (sphingomyelin phosphodiesterase 1deficiency—SMPD1) diseases. When grouped together, LSDs have an incidence in the population of about 1 in 7000 births. These diseases have devastating effects on those afflicted with them. They are usually first diagnosed in babies who may have characteristic facial and body growth patterns and may have moderate to severe mental retardation. Treatment options include enzyme replacement therapy (ERT) where the missing enzyme is given to the patient, usually through intravenous injection in large doses. Such treatment is only to treat the symptoms and is not curative, thus the patient must be given repeated dosing of these proteins for the rest of their lives, and potentially may develop neutralizing antibodies to the injected protein. Often these proteins have a short serum half-life, and so the patient must also endure frequent infusions of the protein. For example, Gaucher's disease patients receiving the Cerezyme® product (imiglucerase) must have infusions three times per week. Production and purification of the enzymes is also problematic, and so the treatments are very costly (>$100,000 per year per patient).

Type I diabetes is a disorder in which immune-mediated destruction of pancreatic beta cells results in a profound deficiency of insulin, which is the primary secreted product of these cells. Restoration of baseline insulin levels provide substantial relief from many of the more serious complications of this disorder which can include "macrovascular" complications involving the large vessels: ischemic heart disease (angina and myocardial infarction), stroke and peripheral vascular disease, as well as "microvascular" complications from damage to the small blood vessels. Microvascular complications may include diabetic retinopathy, which affects blood vessel formation in the retina of the eye, and can lead to visual symptoms, reduced vision, and potentially blindness, and diabetic nephropathy, which may involve scarring changes in the kidney tissue, loss of small or progressively larger amounts of protein in the urine, and eventually chronic kidney disease requiring dialysis. Diabetic neuropathy can cause numbness, tingling and pain in the feet and, together with vascular disease in the legs, contributes to the risk of diabetes-related foot problems (such as diabetic foot ulcers) that can be difficult to treat and occasionally require amputation as a result of associated infections.

Antibodies are secreted protein products whose binding plasticity has been exploited for development of a diverse range of therapies. Therapeutic antibodies can be used for neutralization of target proteins that directly cause disease (e.g. VEGF in macular degeneration) as well as highly selective killing of cells whose persistence and replication endanger the hose (e.g. cancer cells, as well as certain immune cells in autoimmune diseases). In such applications, therapeutic antibodies take advantage of the body's normal response to its own antibodies to achieve selective killing, neutralization, or clearance of target proteins or cells bearing the antibody's target antigen. Thus antibody therapy has been widely applied to many human conditions including oncology, rheumatology, transplant, and ocular disease Examples of antibody therapeutics include Lucentis® (Genentech) for the treatment of macular degeneration, Rituxan® (Biogen Idec) for the treatment of Non-Hodgkin lymphoma, and Herceptin® (Genentech) for the treatment of breast cancer. Albumin is a protein that is produced in the liver and secreted into the blood. In humans, serum albumin comprises 60% of the protein found in blood, and its function seems to be to regulate blood volume by regulating the colloid osmotic pressure. It also serves as a carrier for molecules with low solubility, for example lipid soluble hormones, bile salts, free fatty acids, calcium and transferrin. In addition, serum albumin carries therapeutics, including warfarin, phenobutazone, clofibrate and phenytoin. In humans, the albumin locus is highly expressed, resulting in the production of approximately 15 g of albumin protein each day. Albumin has no autocrine function, and there does not appear to be any phenotype associated with monoallelic knockouts and only mild phenotypic observations are found for biallelic knockouts (see Watkins et al (1994) *Proc Natl Acad Sci USA* 91:9417).

Albumin has also been used when coupled to therapeutic reagents to increase the serum half-life of the therapeutic. For example, Osborn et al (*J Pharm Exp Thera* (2002) 303(2): 540) disclose the pharmacokinetics of a serum albumin-interferon alpha fusion protein and demonstrate that the fusion protein had an approximate 140-fold slower clearance such that the half-life of the fusion was 18-fold longer than for the interferon alpha protein alone. Other examples of therapeutic proteins recently under development that are albumin fusions include Albulin-G™, Cardeva™ and Albugranin™ (Teva Pharmaceutical Industries, fused to Insulin, b-type natriuretic, or GCSF, respectively), Syncria® (GlaxoSmithKline, fused to Glucagon-like peptide-1) and Albuferon α-2B, fused to IFN-alpha (see *Current Opinion in Drug Discovery and Development*, (2009), vol 12, No. 2. p. 288). In these cases, Albulin-G™, Cardeva™ and Syncria® are all fusion proteins where the albumin is found on the N-terminus of the fusion, while Albugranin™ and Albuferon alpha 2G are fusions where the albumin is on the C-terminus of the fusion.

Thus, there remains a need for additional methods and compositions that can be used to express a desired transgene at a therapeutically relevant level, while avoiding any associated toxicity, and which may limit expression of the transgene to the desired tissue type, for example to treat genetic diseases such as hemophilias, diabetes, lysosomal storage diseases and A1AT deficiency. Additionally, there remains a need for additional methods and compositions to express a desired transgene at a therapeutically relevant level for the treatment of other diseases such as cancers.

SUMMARY

Disclosed herein are methods and compositions for creating a safe harbor in the genome of cells, for targeted insertion and subsequence expression of a transgene, for example expression of the transgene from a secretory tissue such as liver. In one aspect, described herein is a non-naturally occurring zinc-finger protein (ZFP) that binds to target site in a region of interest (e.g., an albumin gene) in a genome, wherein the ZFP comprises one or more engineered zinc-finger binding domains. In one embodiment, the ZFP is a zinc-finger nuclease (ZFN) that cleaves a target genomic region of interest, wherein the ZFN comprises one or more engineered zinc-finger binding domains and a nuclease cleavage domain or cleavage half-domain Cleavage domains and cleavage half domains can be obtained, for example, from various restriction endonucleases and/or homing endonucleases. In one embodiment, the cleavage half-domains are derived from a Type IIS restriction endonuclease (e.g., Fok I).

In certain embodiments, the zinc finger domain recognizes a target site in an albumin gene, for example a zinc finger protein with the recognition helix domains ordered as shown in a single row of Tables 1, 3, 5 or 8.

In another aspect, described herein is a Transcription Activator Like Effector (TALE) protein that binds to target site in a region of interest (e.g., an albumin gene) in a genome, wherein the TALE comprises one or more engineered TALE binding domains. In one embodiment, the TALE is a nuclease (TALEN) that cleaves a target genomic region of interest, wherein the TALEN comprises one or more engineered TALE DNA binding domains and a nuclease cleavage domain or cleavage half-domain. Cleavage domains and cleavage half domains can be obtained, for example, from various restriction endonucleases and/or homing endonucleases. In one embodiment, the cleavage half-domains are derived from a Type IIS restriction endonuclease (e.g., Fok I). In certain embodiments, the TALE DNA binding domain recognizes a target site in an albumin gene, for example TALE DNA binding domain having the target sequence shown in a single row of Table 12.

The ZFN and/or TALEN as described herein may bind to and/or cleave the region of interest in a coding or non-coding region within or adjacent to the gene, such as, for example, a leader sequence, trailer sequence or intron, or within a non-transcribed region, either upstream or downstream of the coding region. In certain embodiments, the ZFN binds to and/or cleaves an albumin gene. In other embodiments, the ZFN and/or TALEN binds to and/or cleaves a safe-harbor gene, for example a CCR5 gene, a PPP1R12C (also known as AAVS1) gene or a Rosa gene. See, e.g., U.S. Patent Publication Nos. 20080299580; 20080159996 and 201000218264. In another aspect, described herein are compositions comprising one or more of the zinc-finger and/or TALE nucleases described herein. In certain embodiments, the composition comprises one or more zinc-finger and/or TALE nucleases in combination with a pharmaceutically acceptable excipient.

In another aspect, described herein is a polynucleotide encoding one or more ZFNs and/or TALENs described herein. The polynucleotide may be, for example, mRNA. In some aspects, the mRNA may be chemically modified (See e.g. Kormann et al, (2011) *Nature Biotechnology* 29(2):154-157).

In another aspect, described herein is a ZFN and/or TALEN expression vector comprising a polynucleotide, encoding one or more ZFNs and/or TALENs described herein, operably linked to a promoter. In one embodiment, the expression vector is a viral vector. In one aspect, the viral vector exhibits tissue specific tropism.

In another aspect, described herein is a host cell comprising one or more ZFN and/or TALEN expression vectors. The host cell may be stably transformed or transiently transfected or a combination thereof with one or more ZFP or TALEN expression vectors. In one embodiment, the host cell is an embryonic stem cell. In other embodiments, the one or more ZFP and/or TALEN expression vectors express one or more ZFNs and/or TALENs in the host cell. In another embodiment, the host cell may further comprise an exogenous polynucleotide donor sequence. Non-limiting examples of suitable host cells include eukaryotic cells or cell lines such as secretory cells (e.g., liver cells, mucosal cells, salivary gland cells, pituitary cells, etc.), blood cells (red blood cells), stem cells, etc. In any of the embodiments described herein the host cell can comprise an embryo cell, for example, of a mouse, rat, rabbit or other mammal cell embryo.

In another aspect, described herein is a method for cleaving an albumin gene in a cell, the method comprising: introducing, into the cell, one or more polynucleotides encoding one or more ZFNs and/or TALENs that bind to a target site in the one or more albumin genes under conditions such that the ZFN(s) is (are) or TALENs is (are) expressed and the one or more albumin genes are cleaved.

In other embodiments, a genomic sequence in any target gene is replaced, for example using a ZFN or TALEN (or vector encoding said ZFN or TALEN) as described herein and a "donor" sequence (e.g., transgene) that is inserted into the gene following targeted cleavage with the ZFN and/or TALEN. The donor sequence may be present in the ZFN or TALEN vector, present in a separate vector (e.g., Ad or LV vector) or, alternatively, may be introduced into the cell using a different nucleic acid delivery mechanism. Such insertion of a donor nucleotide sequence into the target locus (e.g., albumin gene, other safe-harbor gene, etc.) results in the expression of the transgene carried by the donor under control of the target locus's (e.g. albumin) genetic control elements. In some aspects, insertion of the transgene of interest, for example into an albumin gene results in expression of an intact exogenous protein sequence and lacks any albumin encoded amino acids. In other aspects, the expressed exogenous protein is a fusion protein and comprises amino acids encoded by the transgene and by an albumin gene (e.g., from the endogenous target locus or, alternatively from albumin-encoding sequences on the transgene). In some instances, the albumin sequences will be present on the amino (N)-terminal portion of the exogenous protein, while in others, the albumin sequences will be present on the carboxy (C)-terminal portion of the exogenous protein. In other instances, albumin sequences will be present on both the N- and C-terminal portions of the exogenous protein. The albumin sequences may include full-length wild-type or mutant albumin sequences or, alternatively, may include partial albumin amino acid sequences. In certain embodiments, the albumin sequences (full-length or partial) serve to increase the serum half-life of the polypeptide expressed by the transgene to which it is fused and/or as a carrier. In some embodiments, the albumin-transgene fusion is located at the endogenous locus within the cell while in other embodiments, the albumin-transgene coding sequence is inserted into a safe harbor within a genome. In some aspects, the safe harbor is selected from the AAVS1, Rosa, HPRT or CCR5 locus (see co-owned US patent publications Nos. 20080299580; 20080159996 and 201000218264, and U.S. Provisional patent application No. 61/556,691).

In another aspect, the invention describes methods and compositions that can be used to express a transgene under the control of an albumin promoter in vivo (e.g., endogenous or exogenous albumin promoter). In some aspects, the transgene may encode a therapeutic protein of interest. The transgene may encode a protein such that the methods of the invention can be used for production of protein that is deficient or lacking (e.g., "protein replacement"). In some instances, the protein may be involved treatment for a lysosomal storage disease. Other therapeutic proteins may be expressed, including protein therapeutics for conditions as diverse as epidermolysis bullosa or AAT deficient emphysema. In other aspects, the transgene may comprise sequences (e.g., engineered sequences) such that the expressed protein has characteristics which give it novel and desirable features (increased half-life, changed plasma clearance characteristics etc.). Engineered sequences can also include amino acids derived from the albumin sequence. In some aspects, the transgenes encode therapeutic proteins, therapeutic hormones, plasma proteins, antibodies and the like. In some aspects, the transgenes may encode proteins involved in blood disorders such as clotting disorders. In some aspects, the transgenes encode structural nucleic acids (shRNAs, miRNAs and the like).

In some embodiments, the methods of the invention may be used in vivo in transgenic animal systems. In some aspects, the transgenic animal may be used in model development where the transgene encodes a human gene. In some instances, the transgenic animal may be knocked out at the corresponding endogenous locus, allowing the development of an in vivo system where the human protein may be studied in isolation. Such transgenic models may be used for screening purposes to identify small molecule, large biomolecules or other entities which may interact or modify the human protein of interest. In other aspects, the transgenic animals may be used for production purposes, for example, to produce antibodies or other biomolecules of interest. In certain embodiments, the animal is a small mammal, for example a dog, rabbit or a rodent such as rat, a mouse or a guinea pig. In other embodiments, the animal is a non-human primate. In yet further embodiments, the animal is a farm animal such as a cow, goat or pig. In some aspects, the transgene is integrated into the selected locus (e.g., albumin or safe-harbor) into a stem cell (e.g., an embryonic stem cell, an induced pluripotent stem cell, a hepatic stem cell, etc.) or animal embryo obtained by any of the methods described herein, and then the embryo is implanted such that a live animal is born. The animal is then raised to sexual maturity and allowed to produce offspring wherein at least some of the offspring comprise the integrated transgene.

In a still further aspect, provided herein is a method for site specific integration of a nucleic acid sequence into an endogenous locus (e.g., albumin gene) of a chromosome, for example into the chromosome of an embryo. In certain embodiments, the method comprises: (a) injecting an embryo with (i) at least one DNA vector, wherein the DNA vector comprises an upstream sequence and a downstream sequence flanking the nucleic acid sequence to be integrated, and (ii) at least one RNA molecule encoding a zinc finger and/or TALE nuclease that recognizes the site of integration in the target locus (e.g., albumin locus), and (b) culturing the embryo to allow expression of the zinc finger and/or TALE nuclease, wherein a double stranded break introduced into the site of integration by the zinc finger nuclease or TALEN is repaired, via homologous recombination with the DNA vector, so as to integrate the nucleic acid sequence into the chromosome.

Suitable embryos may be derived from several different vertebrate species, including mammalian, bird, reptile, amphibian, and fish species. Generally speaking, a suitable embryo is an embryo that may be collected, injected, and cultured to allow the expression of a zinc finger or TALE nuclease. In some embodiments, suitable embryos may include embryos from small mammals (e.g., rodents, rabbits, etc.), companion animals, livestock, and primates. Non-limiting examples of rodents may include mice, rats, hamsters, gerbils, and guinea pigs. Non-limiting examples of companion animals may include cats, dogs, rabbits, hedgehogs, and ferrets. Non-limiting examples of livestock may include horses, goats, sheep, swine, llamas, alpacas, and cattle. Non-limiting examples of primates may include capuchin monkeys, chimpanzees, lemurs, macaques, marmosets, tamarins, spider monkeys, squirrel monkeys, and vervet monkeys. In other embodiments, suitable embryos may include embryos from fish, reptiles, amphibians, or birds. Alternatively, suitable embryos may be insect embryos, for instance, a *Drosophila* embryo or a mosquito embryo.

In any of the methods or compositions described herein, the cell containing the engineered locus (e.g., albumin locus) can be a stem cell. Specific stem cell types that may be used with the methods and compositions of the invention include embryonic stem cells (ESC), induced pluripotent stem cells (iPSC) and hepatic or liver stem cells. The iPSCs can be derived from patient samples and from normal controls wherein the patient derived iPSC can be mutated to normal gene sequence at the gene of interest, or normal cells can be altered to the known disease allele at the gene of interest. Similarly, the hepatic stem cells can be isolated from a patient. These cells are then engineered to express the transgene of interest, expanded and then reintroduced into the patient.

In any of the methods described herein, the polynucleotide encoding the zinc finger nuclease(s) and/or TALEN(s) can comprise DNA, RNA or combinations thereof. In certain embodiments, the polynucleotide comprises a plasmid. In other embodiments, the polynucleotide encoding the nuclease comprises mRNA.

Also provided is an embryo comprising at least one DNA vector, wherein the DNA vector comprises an upstream sequence and a downstream sequence flanking the nucleic acid sequence to be integrated, and at least one RNA molecule encoding a zinc finger nuclease that recognizes the chromosomal site of integration. Organisms derived from any of the embryos as described herein are also provided (e.g., embryos that are allowed to develop to sexual maturity and produce progeny).

In another aspect provided by the methods and compositions of the invention is the use of cells, cell lines and animals (e.g., transgenic animals) in the screening of drug libraries and/or other therapeutic compositions (i.e., antibodies, structural RNAs, etc.) for use in treatment of an animal afflicted with a clotting factor disorder. Such screens can begin at the cellular level with manipulated cell lines or primary cells, and can progress up to the level of treatment of a whole animal (e.g., human).

A kit, comprising the ZFPs and/or TALENs of the invention, is also provided. The kit may comprise nucleic acids encoding the ZFPs or TALENs, (e.g. RNA molecules or ZFP or TALEN encoding genes contained in a suitable expression vector), donor molecules, suitable host cell lines, instructions for performing the methods of the invention, and the like.

Thus, the disclosure herein includes, but is not limited to, the following embodiments:

1. A non-naturally occurring fusion protein comprising a DNA-binding protein that binds to an endogenous albumin gene and a cleavage domain, wherein the fusion protein modifies the endogenous albumin gene.

2. The fusion protein of embodiment 1, wherein the DNA-binding protein comprises a zinc finger protein.

3. The fusion protein of embodiment 2, wherein the zinc finger protein comprises 4, 5 or 6 zinc finger domains comprising a recognition helix region, wherein the zinc finger proteins comprise the recognition helix regions shown in a single row of Table 1, Table 3, Table 5 or Table 8.

4. The fusion protein of embodiment 1, wherein the DNA-binding protein comprises a TALE DNA-binding domain.

5. The fusion protein of embodiment 4, wherein the TALE DNA-binding domain binds to a target sequence shown in a single row of Table 12.

6. A polynucleotide encoding one or more fusion proteins of embodiments 1 to 5.

7. An isolated cell comprising one or more fusion proteins according to embodiments 1 to 5 or one or more polynucleotides according to embodiment 6.

8. The cell of embodiment 7, wherein the cell is a stem cell or an embryo cell.

9. The cell of embodiment 8, wherein the stem cell is selected from the group consisting of an embryonic stem cell (ESC), an induced pluripotent stem cell (iPSC), a hepatic stem cell and a liver stem cell.

10. A kit comprising a fusion protein according to embodiments 1 to 5 or a polynucleotide according to embodiment 6 or a cell according to embodiment 7-9.

11. A method of cleaving an endogenous albumin gene in a cell, the method comprising:
introducing, into the cell, one or more expression vectors comprising at least one polynucleotide according to embodiment 6, under conditions such that the one or more fusion proteins are expressed and the albumin gene is cleaved.

12. The method of embodiment 11, wherein the polynucleotide comprises an AAV vector.

13. The method of embodiment 11, wherein the cell is a liver cell.

14. A method of introducing a transgene into an endogenous albumin gene, the method comprising:
cleaving the endogenous albumin gene according to the method of any of embodiments 15-17 in the presence of an exogenous polynucleotide comprising the transgene such that the transgene is integrated into the endogenous albumin gene.

15. The method of embodiment 14, wherein the transgene expresses a therapeutic protein.

16. The method of embodiment 15, wherein the therapeutic protein is involved in treating a lysosomal storage disease, epidermolysis bullosa, AAT deficient emphysema or blood disorders such as clotting disorders.

17. The method of embodiments 15 or 16, wherein expression of the transgene is driven by the endogenous albumin control sequences.

18. The method of any of embodiments 15-17, wherein the transgene further comprises albumin sequences.

19. The method of embodiment 18, wherein the albumin sequences are present on the amino (N)-terminal and/or carboxy (C)-terminal portion of the protein.

20. A method of increasing the serum half-life of a polypeptide expressed from a transgene integrated into an endogenous albumin gene, the method comprising introducing the transgene into the endogenous albumin gene according to the method of embodiment 18 or embodiment 19, wherein the transgene expresses the polypeptide and albumin sequences such that the serum half-life of the polypeptide in increased.

21. A method of treating a subject having a disease caused by a deficiency of a polypeptide, the method comprising, introducing a transgene encoding the polypeptide into an isolated cell according to the method of embodiments 14-19 such that the transgene is expressed in the isolated cell; and introducing the isolated cell into the subject, thereby treating the disease.

22. The method of embodiment 21, wherein the cell is a liver cell or a stem cell.

23. The cell of embodiment 22, wherein the stem cell is selected from the group consisting of an embryonic stem cell (ESC), an induced pluripotent stem cell (iPSC), a hepatic stem cell and a liver stem cell.

These and other aspects will be readily apparent to the skilled artisan in light of disclosure as a whole.

BRIEF DESCRIPTION OF THE DRAWINGS

FIG. 1, panels A and B, are gels depicting the results of a Cel-I mismatch assay (Surveyor™, Transgenomic) that quantifies the degree to which ZFN cleavage of an endogenous chromosomal target, followed by imperfect repair via NHEJ, has yielded small insertions or deletions ("indels") of the targeted locus. For a description of the assay see Horton et al. *Methods Mol Biol.* (2010) 649:247-56.

FIG. 2, panels A and B, are gels depicting the results of a Cel-I mismatch assay carried out on canine D17 cells transfected with constructs expressing the canine albumin specific ZFN pair SBS 33115/SBS34077 at two concentrations of plasmid DNA, 20 or 40 ng. FIG. 2A depicts the results after 3 days while

FIG. 3, panels A and B, show alignments of the albumin genes from a variety of species of interest. FIG. 3A shows an alignment of exon 1 and the 5' region of intron 1 of human (*H. sapiens*, SEQ ID NO:160), rhesus macaque monkeys (*M. mulatta*, SEQ ID NO:73), marmoset (*C. jacchus*, SEQ ID NO:74), dog (*C. familiaris*, SEQ ID NO:165), rat (*R. norvegicus*, SEQ ID NO:165) and mouse (*M. musculus*, SEQ ID NO:76). 3B shows an alignment of the remainder of intron 1 and a small fragment of exon 2. This region includes the Locus 1 to Locus 5 of human (SEQ ID NO:161), rhesus macaque monkeys (SEQ ID NO:77), marmoset (SEQ ID NO:78), dog (SEQ ID NO:79), rat (SEQ ID NO:80) and mouse (*M. musculus*, SEQ ID NO:81) which are loci in the albumin gene chosen for ZFN targeting. The sequences depicted show the starting codon ATG (large box in FIG. 3A) and the boundaries of exon1 and intron 1 (FIG. 3A) and intron 1 and exon 2 (FIG. 3B).

FIG. 4, panels A and B, depict the results of a Cel-I mismatch assay carried out on genomic DNA from liver tissue biopsied from mice injected with albumin-specific ZFNs expressed from a hepatotrophic AAV8 vector. The results are from 10 wild type mice (numbers 273-282) injected intravenously via tail vein injection with two sets of ZFN pairs (pair 1: SBS30724 and SBS30725 and pair 2: SBS30872 and SBS30873).

FIG. 5, panels A and B, show the results of a Cel-I mismatch assay carried out on genomic DNA from liver tissue biopsied from mice injected with albumin-specific ZFNs expressed from different chimeric AAV vectors. Experimental details are provided in Example 5. FIG. 5A demonstrates that the ZFNs are able to cleave the albumin target in the liver in vivo when introduced into the animal via AAV-mediated gene delivery. The percent of albumin genes bearing ZFN-induced modifications in the liver biopsies ranged up to 16 percent. FIG. 5B shows a Western blot of liver tissue using either anti-Flag antibodies or anti-p65. The open reading frames encoding the ZFNs were fused to a sequence encoding a polypeptide FLAG-tag. Thus, the anti-Flag antibody detected the ZFNs and demonstrated ZFN expression in the mice receiving ZFNs. The anti-p65 antibody served as a loading control in these experiments and indicated that comparable amounts of protein were loaded in each lane.

FIG. 9 (SEQ ID NO:82) provides a segment of the human albumin gene sequence encompassing parts of exon 1 and intron 1. Horizontal bars over the sequence indicate the target sites of the zinc finger nucleases.

FIG. 10 shows an alignment of a segment of the albumin genes in intron 1 from a variety of primate species including human, *H. sapiens* (SEQ ID NO:154), cynologous monkey variants (where sequences 'C' and 'S' derive from two different genome sequence sources): *M. fascicularis*_c (SEQ ID NO:155) and *M. fascicularis*_s (SEQ ID NO:156) and rhesus, *M mulatta* (SEQ ID NO:157). The figure depicts the DNA target locations of the albumin specific TALENs (indicated by the horizontal bars above the sequence).

FIG. 12, panels A, B and C depict the results of ZFN pairs directed to the rhesus macaque albumin locus.

FIG. 13, panels A and B, demonstrate the insertion of a huGLa transgene donor (deficient in patients afflicted with Fabry's disease) into the albumin locus in mice. FIG. 13A shows a Western blot against the huGLa protein encoded by the transgene, where the arrow indicates the presumed protein. Comparison of the mouse samples from those mice that received both ZFN and donor (samples 1-1, 1-2 and 1-3) with the samples that either received only ZFN (4-1, 4-2, 4-3) or those that only received the huGLa donor ("hu Fabry donor"), samples 5-1 and 5-2 leads to identification of a band that coincides with the human liver lysate control. FIG. 13B depicts ELISA results using a huGLa specific ELISA kit, where samples were analyzed from mice either 14 or 30 days following virus introduction (see text for details). Error bars represent standard deviations (n=3). The results demonstrate that the mice that received both the ZFN and donor had higher amounts of huGLa signal that those that only received ZFN or only received donor.

DETAILED DESCRIPTION

Figure 1A:
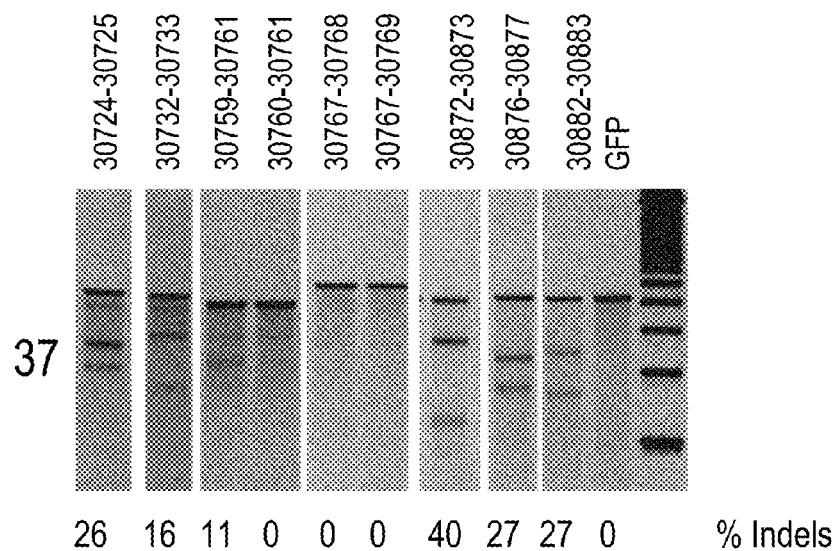
FIG. 1A shows results using expression constructs for ZFNs targeted to the mouse albumin gene which were transfected into Neuro2A cells, where the cells were treated for 3 days at 37° C. following transfection, and then analyzed for the fraction of modified target sites via Cel-I analysis.

Disclosed herein are compositions and methods for modifying an endogenous albumin gene, for example, for expressing a transgene in a secretory tissue. In some embodiments, the transgene is inserted into an endogenous albumin gene to allow for very high expression levels that are moreover limited to hepatic tissue. The transgene can encode any protein or peptide including those providing therapeutic benefit.

Thus, the methods and compositions of the invention can be used to express therapeutically beneficial proteins (from a transgene) from highly expressed loci in secretory tissues. For example, the transgene can encode a protein involved in disorders of the blood, for example, clotting disorders, and a variety of other monogenic diseases. In some embodiments, the transgene can be inserted into the endogenous albumin locus such that expression of the transgene is controlled by the albumin expressional control elements, resulting in liver-specific expression of the transgene encoded protein at high concentrations. Proteins that may be expressed may include clotting factors such as Factor VII, Factor VIII, Factor IX, Factor X, Factor XI, Factor XIII, vWF and the like, antibodies, proteins relevant to lyososomal storage, insulin, alpha 1-antitrypsin, and indeed any peptide or protein that when so expressed provides benefit.

In addition, any transgene can be introduced into patient derived cells, e.g. patient derived induced pluripotent stem cells (iPSCs) or other types of stem cells (embryonic, hematopoietic, neural, or mesenchymal as a non-limiting set) for use in eventual implantation into secretory tissues. The transgene can be introduced into any region of interest in these cells, including, but not limited to, into an albumin gene or a safe harbor gene. These altered stem cells can be differentiated for example, into hepatocytes and implanted into the liver. Alternately, the transgene can be directed to the secretory tissue as desired through the use of viral or other delivery systems that target specific tissues. For example, use of the liver-trophic adenovirus associated virus (AAV) vector AAV8 as a delivery vehicle can result in the integration of the transgene at the desired locus when specific nucleases are co-delivered with the transgene.

General

Practice of the methods, as well as preparation and use of the compositions disclosed herein employ, unless otherwise indicated, conventional techniques in molecular biology, biochemistry, chromatin structure and analysis, computational chemistry, cell culture, recombinant DNA and related fields as are within the skill of the art. These techniques are fully explained in the literature. See, for example, Sambrook et al. MOLECULAR CLONING: A LABORATORY MANUAL, Second edition, Cold Spring Harbor Laboratory Press, 1989 and Third edition, 2001; Ausubel et al., CURRENT PROTOCOLS IN MOLECULAR BIOLOGY, John Wiley & Sons, New York, 1987 and periodic updates; the series METHODS IN ENZYMOLOGY, Academic Press, San Diego; Wolffe, CHROMATIN STRUCTURE AND FUNCTION, Third edition, Academic Press, San Diego, 1998; METHODS IN ENZYMOLOGY, Vol. 304, "Chromatin" (P. M. Wassarman and A. P. Wolffe, eds.), Academic Press, San Diego, 1999; and METHODS IN MOLECULAR BIOLOGY, Vol. 119, "Chromatin Protocols" (P. B. Becker, ed.) Humana Press, Totowa, 1999.

DEFINITIONS

The terms "nucleic acid," "polynucleotide," and "oligonucleotide" are used interchangeably and refer to a deoxyribonucleotide or ribonucleotide polymer, in linear or circular conformation, and in either single- or double-stranded form. For the purposes of the present disclosure, these terms are not to be construed as limiting with respect to the length of a polymer. The terms can encompass known analogues of natural nucleotides, as well as nucleotides that are modified in the base, sugar and/or phosphate moieties (e.g., phosphorothioate backbones). In general, an analogue of a particular nucleotide has the same base-pairing specificity; i.e., an analogue of A will base-pair with T.

The teems "polypeptide," "peptide" and "protein" are used interchangeably to refer to a polymer of amino acid residues. The term also applies to amino acid polymers in which one or more amino acids are chemical analogues or modified derivatives of corresponding naturally-occurring amino acids.

"Binding" refers to a sequence-specific, non-covalent interaction between macromolecules (e.g., between a protein and a nucleic acid). Not all components of a binding interaction need be sequence-specific (e.g., contacts with phosphate residues in a DNA backbone), as long as the interaction as a whole is sequence-specific. Such interactions are generally characterized by a dissociation constant ($K_d$) of $10^{-6}$ $M^{-1}$ or lower. "Affinity" refers to the strength of binding: increased binding affinity being correlated with a lower $K_d$.

A "binding protein" is a protein that is able to bind non-covalently to another molecule. A binding protein can bind to, for example, a DNA molecule (a DNA-binding protein), an RNA molecule (an RNA-binding protein) and/or a protein molecule (a protein-binding protein). In the case of a protein-binding protein, it can bind to itself (to form homodimers, homotrimers, etc.) and/or it can bind to one or more molecules of a different protein or proteins. A binding protein can have more than one type of binding activity. For example, zinc finger proteins have DNA-binding, RNA-binding and protein-binding activity.

A "zinc finger DNA binding protein" (or binding domain) is a protein, or a domain within a larger protein, that binds DNA in a sequence-specific manner through one or more zinc fingers, which are regions of amino acid sequence within the binding domain whose structure is stabilized through coordination of a zinc ion. The term zinc finger DNA binding protein is often abbreviated as zinc finger protein or ZFP.

A "TALE DNA binding domain" or "TALE" is a polypeptide comprising one or more TALE repeat domains/units. The repeat domains are involved in binding of the TALE to its cognate target DNA sequence. A single "repeat unit" (also referred to as a "repeat") is typically 33-35 amino acids in length and exhibits at least some sequence homology with other TALE repeat sequences within a naturally occurring TALE protein. See, e.g., U.S. Patent Publication No. 20110301073, incorporated by reference herein in its entirety.

Zinc finger and TALE binding domains can be "engineered" to bind to a predetermined nucleotide sequence, for example via engineering (altering one or more amino acids) of the recognition helix region of a naturally occurring zinc finger or TALE protein. Therefore, engineered DNA binding proteins (zinc fingers or TALEs) are proteins that are non-naturally occurring. Non-limiting examples of methods for engineering DNA-binding proteins are design and selection. A designed DNA binding protein is a protein not occurring in nature whose design/composition results principally from rational criteria. Rational criteria for design include application of substitution rules and computerized algorithms for processing information in a database storing information of existing ZFP and/or TALE designs and binding data. See, for example, U.S. Pat. Nos. 6,140,081; 6,453,242; and 6,534,261; see also WO 98/53058; WO 98/53059; WO 98/53060; WO 02/016536 and WO 03/016496 and U.S. Publication No. 20110301073.

A "selected" zinc finger protein or TALE is a protein not found in nature whose production results primarily from an empirical process such as phage display, interaction trap or hybrid selection. See e.g., U.S. Pat. No. 5,789,538; U.S. Pat. No. 5,925,523; U.S. Pat. No. 6,007,988; U.S. Pat. No. 6,013,453; U.S. Pat. No. 6,200,759; WO 95/19431; WO 96/06166; WO 98/53057; WO 98/54311; WO 00/27878; WO 01/60970 WO 01/88197; WO 02/099084 and U.S. Publication No. 20110301073.

"Recombination" refers to a process of exchange of genetic information between two polynucleotides. For the purposes of this disclosure, "homologous recombination (HR)" refers to the specialized form of such exchange that takes place, for example, during repair of double-strand breaks in cells via homology-directed repair mechanisms. This process requires nucleotide sequence homology, uses a "donor" molecule to template repair of a "target" molecule (i.e., the one that experienced the double-strand break), and is variously known as "non-crossover gene conversion" or "short tract gene conversion," because it leads to the transfer of genetic information from the donor to the target. Without wishing to be bound by any particular theory, such transfer can involve mismatch correction of heteroduplex DNA that forms between the broken target and the donor, and/or "synthesis-dependent strand annealing," in which the donor is used to re-synthesize genetic information that will become part of the target, and/or related processes. Such specialized HR often results in an alteration of the sequence of the target molecule such that part or all of the sequence of the donor polynucleotide is incorporated into the target polynucleotide.

In the methods of the disclosure, one or more targeted nucleases as described herein create a double-stranded break in the target sequence (e.g., cellular chromatin) at a predetermined site, and a "donor" polynucleotide, having homology to the nucleotide sequence in the region of the break, can be introduced into the cell. The presence of the double-stranded break has been shown to facilitate integration of the donor sequence. The donor sequence may be physically integrated or, alternatively, the donor polynucleotide is used as a template for repair of the break via homologous recombination, resulting in the introduction of all or part of the nucleotide sequence as in the donor into the cellular chromatin. Thus, a first sequence in cellular chromatin can be altered and, in certain embodiments, can be converted into a sequence present in a donor polynucleotide. Thus, the use of the terms "replace" or "replacement" can be understood to represent replacement of one nucleotide sequence by another, (i.e., replacement of a sequence in the informational sense), and does not necessarily require physical or chemical replacement of one polynucleotide by another.

In any of the methods described herein, additional pairs of zinc-finger or TALEN proteins can be used for additional double-stranded cleavage of additional target sites within the cell.

In certain embodiments of methods for targeted recombination and/or replacement and/or alteration of a sequence in a region of interest in cellular chromatin, a chromosomal sequence is altered by homologous recombination with an exogenous "donor" nucleotide sequence. Such homologous recombination is stimulated by the presence of a double-stranded break in cellular chromatin, if sequences homologous to the region of the break are present.

In any of the methods described herein, the first nucleotide sequence (the "donor sequence") can contain sequences that are homologous, but not identical, to genomic sequences in the region of interest, thereby stimulating homologous recombination to insert a non-identical sequence in the region of interest. Thus, in certain embodiments, portions of the donor sequence that are homologous to sequences in the region of interest exhibit between about 80 to 99% (or any value therebetween) sequence identity to the genomic sequence that is replaced. In other embodiments, the homology between the donor and genomic sequence is higher than 99%, for example if only 1 nucleotide differs as between donor and genomic sequences of over 101 contiguous base pairs. In certain cases, a non-homologous portion of the donor sequence can contain sequences not present in the region of interest, such that new sequences are introduced into the region of interest. In these instances, the non-homologous sequence is generally flanked by sequences of 50-1,000 base pairs (or any integral value therebetween) or any number of base pairs greater than 1,000, that are homologous or identical to sequences in the region of interest. In other embodiments, the donor sequence is non-homologous to the first sequence, and is inserted into the genome by non-homologous recombination mechanisms.

Any of the methods described herein can be used for partial or complete inactivation of one or more target sequences in a cell by targeted integration of donor sequence that disrupts expression of the gene(s) of interest. Cell lines with partially or completely inactivated genes are also provided.

Furthermore, the methods of targeted integration as described herein can also be used to integrate one or more exogenous sequences. The exogenous nucleic acid sequence can comprise, for example, one or more genes or cDNA molecules, or any type of coding or non-coding sequence, as well as one or more control elements (e.g., promoters). In addition, the exogenous nucleic acid sequence may produce one or more RNA molecules (e.g., small hairpin RNAs (shRNAs), inhibitory RNAs (RNAis), microRNAs (miRNAs), etc.).

"Cleavage" refers to the breakage of the covalent backbone of a DNA molecule. Cleavage can be initiated by a variety of methods including, but not limited to, enzymatic or chemical hydrolysis of a phosphodiester bond. Both single-stranded cleavage and double-stranded cleavage are possible, and double-stranded cleavage can occur as a result of two distinct single-stranded cleavage events. DNA cleavage can result in the production of either blunt ends or staggered ends. In certain embodiments, fusion polypeptides are used for targeted double-stranded DNA cleavage.

A "cleavage half-domain" is a polypeptide sequence which, in conjunction with a second polypeptide (either identical or different) forms a complex having cleavage activity (preferably double-strand cleavage activity). The terms "first and second cleavage half-domains;" "+ and − cleavage half-domains" and "right and left cleavage half-domains" are used interchangeably to refer to pairs of cleavage half-domains that dimerize.

An "engineered cleavage half-domain" is a cleavage half-domain that has been modified so as to form obligate heterodimers with another cleavage half-domain (e.g., another engineered cleavage half-domain). See, also, U.S. Patent Publication Nos. 2005/0064474, 20070218528, 2008/0131962 and 2011/0201055, incorporated herein by reference in their entireties.

The term "sequence" refers to a nucleotide sequence of any length, which can be DNA or RNA; can be linear, circular or branched and can be either single-stranded or double stranded. The term "donor sequence" refers to a nucleotide sequence that is inserted into a genome. A donor sequence can be of any length, for example between 2 and 10,000 nucleotides in length (or any integer value therebetween or thereabove), preferably between about 100 and 1,000 nucleotides in length (or any integer therebetween), more preferably between about 200 and 500 nucleotides in length.

"Chromatin" is the nucleoprotein structure comprising the cellular genome. Cellular chromatin comprises nucleic acid, primarily DNA, and protein, including histones and non-histone chromosomal proteins. The majority of eukaryotic cellular chromatin exists in the form of nucleosomes, wherein a nucleosome core comprises approximately 150 base pairs of DNA associated with an octamer comprising two each of histones H2A, H2B, H3 and H4; and linker DNA (of variable length depending on the organism) extends between nucleosome cores. A molecule of histone H1 is generally associated with the linker DNA. For the purposes of the present disclosure, the term "chromatin" is meant to encompass all types of cellular nucleoprotein, both prokaryotic and eukaryotic. Cellular chromatin includes both chromosomal and episomal chromatin.

A "chromosome," is a chromatin complex comprising all or a portion of the genome of a cell. The genome of a cell is often characterized by its karyotype, which is the collection of all the chromosomes that comprise the genome of the cell. The genome of a cell can comprise one or more chromosomes.

An "episome" is a replicating nucleic acid, nucleoprotein complex or other structure comprising a nucleic acid that is not part of the chromosomal karyotype of a cell. Examples of episomes include plasmids and certain viral genomes.

A "target site" or "target sequence" is a nucleic acid sequence that defines a portion of a nucleic acid to which a binding molecule will bind, provided sufficient conditions for binding exist.

An "exogenous" molecule is a molecule that is not normally present in a cell, but can be introduced into a cell by one or more genetic, biochemical or other methods. "Normal presence in the cell" is determined with respect to the particular developmental stage and environmental conditions of the cell. Thus, for example, a molecule that is present only during embryonic development of muscle is an exogenous molecule with respect to an adult muscle cell. Similarly, a molecule induced by heat shock is an exogenous molecule with respect to a non-heat-shocked cell. An exogenous molecule can comprise, for example, a functioning version of a malfunctioning endogenous molecule or a malfunctioning version of a normally-functioning endogenous molecule.

An exogenous molecule can be, among other things, a small molecule, such as is generated by a combinatorial chemistry process, or a macromolecule such as a protein, nucleic acid, carbohydrate, lipid, glycoprotein, lipoprotein, polysaccharide, any modified derivative of the above molecules, or any complex comprising one or more of the above molecules. Nucleic acids include DNA and RNA, can be single- or double-stranded; can be linear, branched or circular; and can be of any length. Nucleic acids include those capable of forming duplexes, as well as triplex-forming nucleic acids. See, for example, U.S. Pat. Nos. 5,176,996 and 5,422,251. Proteins include, but are not limited to, DNA-binding proteins, transcription factors, chromatin remodeling factors, methylated DNA binding proteins, polymerases, methylases, demethylases, acetylases, deacetylases, kinases, phosphatases, integrases, recombinases, ligases, topoisomerases, gyrases and helicases.

An exogenous molecule can be the same type of molecule as an endogenous molecule, e.g., an exogenous protein or nucleic acid. For example, an exogenous nucleic acid can comprise an infecting viral genome, a plasmid or episome introduced into a cell, or a chromosome that is not normally present in the cell. Methods for the introduction of exogenous molecules into cells are known to those of skill in the art and include, but are not limited to, lipid-mediated transfer (i.e., liposomes, including neutral and cationic lipids), electroporation, direct injection, cell fusion, particle bombardment, calcium phosphate co-precipitation, DEAE-dextran-mediated transfer and viral vector-mediated transfer. An exogenous molecule can also be the same type of molecule as an endogenous molecule but derived from a different species than the cell is derived from. For example, a human nucleic acid sequence may be introduced into a cell line originally derived from a mouse or hamster.

By contrast, an "endogenous" molecule is one that is normally present in a particular cell at a particular developmental stage under particular environmental conditions. For example, an endogenous nucleic acid can comprise a chromosome, the genome of a mitochondrion, chloroplast or other organelle, or a naturally-occurring episomal nucleic acid. Additional endogenous molecules can include proteins, for example, transcription factors and enzymes.

A "fusion" molecule is a molecule in which two or more subunit molecules are linked, preferably covalently. The subunit molecules can be the same chemical type of molecule, or can be different chemical types of molecules. Examples of the first type of fusion molecule include, but are not limited to, fusion proteins (for example, a fusion between a ZFP or TALE DNA-binding domain and one or more activation domains) and fusion nucleic acids (for example, a nucleic acid encoding the fusion protein described supra). Examples of the second type of fusion molecule include, but are not limited to, a fusion between a triplex-forming nucleic acid and a polypeptide, and a fusion between a minor groove binder and a nucleic acid.

Expression of a fusion protein in a cell can result from delivery of the fusion protein to the cell or by delivery of a polynucleotide encoding the fusion protein to a cell, wherein the polynucleotide is transcribed, and the transcript is translated, to generate the fusion protein. Trans-splicing, polypeptide cleavage and polypeptide ligation can also be involved in expression of a protein in a cell. Methods for polynucleotide and polypeptide delivery to cells are presented elsewhere in this disclosure.

A "gene," for the purposes of the present disclosure, includes a DNA region encoding a gene product (see infra), as well as all DNA regions which regulate the production of the gene product, whether or not such regulatory sequences are adjacent to coding and/or transcribed sequences. Accordingly, a gene includes, but is not necessarily limited to, promoter sequences, terminators, translational regulatory sequences such as ribosome binding sites and internal ribosome entry sites, enhancers, silencers, insulators, boundary elements, replication origins, matrix attachment sites and locus control regions.

"Gene expression" refers to the conversion of the information, contained in a gene, into a gene product. A gene product can be the direct transcriptional product of a gene (e.g., mRNA, tRNA, rRNA, antisense RNA, ribozyme, structural RNA or any other type of RNA) or a protein produced by translation of an mRNA. Gene products also include RNAs which are modified, by processes such as capping, polyadenylation, methylation, and editing, and proteins modified by, for example, methylation, acetylation, phosphorylation, ubiquitination, ADP-ribosylation, myristilation, and glycosylation.

"Modulation" of gene expression refers to a change in the activity of a gene. Modulation of expression can include, but is not limited to, gene activation and gene repression. Genome editing (e.g., cleavage, alteration, inactivation, random mutation) can be used to modulate expression. Gene inactivation refers to any reduction in gene expression as compared to a cell that does not include a ZFP or TALEN as described herein. Thus, gene inactivation may be partial or complete.

A "region of interest" is any region of cellular chromatin, such as, for example, a gene or a non-coding sequence within or adjacent to a gene, in which it is desirable to bind an exogenous molecule. Binding can be for the purposes of targeted DNA cleavage and/or targeted recombination. A region of interest can be present in a chromosome, an episome, an organellar genome (e.g., mitochondrial, chloroplast), or an infecting viral genome, for example. A region of interest can be within the coding region of a gene, within transcribed non-coding regions such as, for example, leader sequences, trailer sequences or introns, or within non-transcribed regions, either upstream or downstream of the coding region. A region of interest can be as small as a single nucleotide pair or up to 2,000 nucleotide pairs in length, or any integral value of nucleotide pairs.

"Eukaryotic" cells include, but are not limited to, fungal cells (such as yeast), plant cells, animal cells, mammalian cells and human cells (e.g., T-cells).

"Secretory tissues" are those tissues that secrete products. Examples of secretory tissues that are localized to the gastrointestinal tract include the cells that line the gut, the pancreas, and the gallbladder. Other secretory tissues include the liver, tissues associated with the eye and mucous membranes such as salivary glands, mammary glands, the prostate gland, the pituitary gland and other members of the endocrine system. Additionally, secretory tissues include individual cells of a tissue type which are capable of secretion.

The terms "operative linkage" and "operatively linked" (or "operably linked") are used interchangeably with reference to a juxtaposition of two or more components (such as sequence elements), in which the components are arranged such that both components function normally and allow the possibility that at least one of the components can mediate a function that is exerted upon at least one of the other components. By way of illustration, a transcriptional regulatory sequence, such as a promoter, is operatively linked to a coding sequence if the transcriptional regulatory sequence controls the level of transcription of the coding sequence in response to the presence or absence of one or more transcriptional regulatory factors. A transcriptional regulatory sequence is generally operatively linked in cis with a coding sequence, but need not be directly adjacent to it. For example, an enhancer is a transcriptional regulatory sequence that is operatively linked to a coding sequence, even though they are not contiguous.

With respect to fusion polypeptides, the term "operatively linked" can refer to the fact that each of the components performs the same function in linkage to the other component as it would if it were not so linked. For example, with respect to a fusion polypeptide in which a ZFP or TALE DNA-binding domain is fused to an activation domain, the ZFP or TALE DNA-binding domain and the activation domain are in operative linkage if, in the fusion polypeptide, the ZFP or TALE DNA-binding domain portion is able to bind its target site and/or its binding site, while the activation domain is able to up-regulate gene expression. When a fusion polypeptide in which a ZFP or TALE DNA-binding domain is fused to a cleavage domain, the ZFP or TALE DNA-binding domain and the cleavage domain are in operative linkage if, in the fusion polypeptide, the ZFP or TALE DNA-binding domain portion is able to bind its target site and/or its binding site, while the cleavage domain is able to cleave DNA in the vicinity of the target site.

A "functional fragment" of a protein, polypeptide or nucleic acid is a protein, polypeptide or nucleic acid whose sequence is not identical to the full-length protein, polypeptide or nucleic acid, yet retains the same function as the full-length protein, polypeptide or nucleic acid. A functional fragment can possess more, fewer, or the same number of residues as the corresponding native molecule, and/or can contain one or more amino acid or nucleotide substitutions. Methods for determining the function of a nucleic acid (e.g., coding function, ability to hybridize to another nucleic acid) are well-known in the art. Similarly, methods for determining protein function are well-known. For example, the DNA-binding function of a polypeptide can be determined, for example, by filter-binding, electrophoretic mobility-shift, or immunoprecipitation assays. DNA cleavage can be assayed by gel electrophoresis. See Ausubel et al., supra. The ability of a protein to interact with another protein can be determined, for example, by co-immunoprecipitation, two-hybrid assays or complementation, both genetic and biochemical. See, for example, Fields et al. (1989) Nature 340:245-246; U.S. Pat. No. 5,585,245 and PCT WO 98/44350.

A "vector" is capable of transferring gene sequences to target cells. Typically, "vector construct," "expression vector," and "gene transfer vector," mean any nucleic acid construct capable of directing the expression of a gene of interest and which can transfer gene sequences to target cells. Thus, the lean includes cloning, and expression vehicles, as well as integrating vectors.

A "reporter gene" or "reporter sequence" refers to any sequence that produces a protein product that is easily measured, preferably although not necessarily in a routine assay. Suitable reporter genes include, but are not limited to, sequences encoding proteins that mediate antibiotic resistance (e.g., ampicillin resistance, neomycin resistance, G418 resistance, puromycin resistance), sequences encoding colored or fluorescent or luminescent proteins (e.g., green fluorescent protein, enhanced green fluorescent protein, red fluorescent protein, luciferase), and proteins which mediate enhanced cell growth and/or gene amplification (e.g., dihydrofolate reductase). Epitope tags include, for example, one or more copies of FLAG, His, myc, Tap, HA or any detectable amino acid sequence. "Expression tags" include sequences that encode gene reporters that may be operably linked to a desired gene sequence in order to monitor expression of the gene of interest.

Nucleases

Described herein are compositions, particularly nucleases, which are useful targeting a gene for the insertion of a transgene, for example, nucleases that are specific for albumin. In certain embodiments, the nuclease is naturally occurring. In other embodiments, the nuclease is non-naturally occurring, i.e., engineered in the DNA-binding domain and/or cleavage domain. For example, the DNA-binding domain of a naturally-occurring nuclease may be altered to bind to a selected target site (e.g., a meganuclease that has been engineered to bind to site different than the cognate binding site). In other embodiments, the nuclease comprises heterologous DNA-binding and cleavage domains (e.g., zinc finger nucleases; TAL-effector nucleases; meganuclease DNA-binding domains with heterologous cleavage domains).

A. DNA-Binding Domains

In certain embodiments, the nuclease is a meganuclease (homing endonuclease). Naturally-occurring meganucleases recognize 15-40 base-pair cleavage sites and are commonly grouped into four families: the LAGLIDADG (SEQ ID NO: 162) family, the GIY-YIG family, the His-Cyst box family and the HNH family. Exemplary homing endonucleases include I-SceI, I-CeuI, PI-PspI, PI-Sce, I-SceIV, I-CsmI, I-PanI, I-SceII, I-PpoI, I-SceIII, I-CreI, I-TevI, I-TevII and I-TevIII. Their recognition sequences are known. See also U.S. Pat. No. 5,420,032; U.S. Pat. No. 6,833,252; Belfort et al. (1997) Nucleic Acids Res. 25:3379-3388; Dujon et al. (1989) Gene 82:115-118; Perler et al. (1994) Nucleic Acids Res. 22, 1125-1127; Jasin (1996) Trends Genet. 12:224-228; Gimble et al. (1996) J. Mol. Biol. 263:163-180; Argast et al. (1998) J. Mol. Biol. 280:345-353 and the New England Biolabs catalogue.

In certain embodiments, the nuclease comprises an engineered (non-naturally occurring) homing endonuclease (meganuclease). The recognition sequences of homing endonucleases and meganucleases such as I-SceI, I-CeuI, PI-PspI, PI-Sce, I-SceIV, I-CsmI, I-PanI, I-SceII, I-PpoI, I-SceIII, I-CreI, I-TevI, I-TevII and I-TevIII are known. See also U.S. Pat. No. 5,420,032; U.S. Pat. No. 6,833,252; Belfort et al. (1997) Nucleic Acids Res. 25:3379-3388; Dujon et al. (1989)

*Gene* 82:115-118; Perler et al. (1994) *Nucleic Acids Res.* 22, 1125-1127; Jasin (1996) *Trends Genet.* 12:224-228; Gimble et al. (1996) *J. Mol. Biol.* 263:163-180; Argast et al. (1998) *J. Mol. Biol.* 280:345-353 and the New England Biolabs catalogue. In addition, the DNA-binding specificity of homing endonucleases and meganucleases can be engineered to bind non-natural target sites. See, for example, Chevalier et al. (2002) *Molec. Cell* 10:895-905; Epinat et al. (2003) *Nucleic Acids Res.* 31:2952-2962; Ashworth et al. (2006) *Nature* 441: 656-659; Paques et al. (2007) *Current Gene Therapy* 7:49-66; U.S. Patent Publication No. 20070117128. The DNA-binding domains of the homing endonucleases and meganucleases may be altered in the context of the nuclease as a whole (i.e., such that the nuclease includes the cognate cleavage domain) or may be fused to a heterologous cleavage domain.

In other embodiments, the DNA-binding domain comprises a naturally occurring or engineered (non-naturally occurring) TALE DNA binding domain. See, e.g., U.S. Patent Publication No. 2011/0301073, incorporated by reference in its entirety herein. The plant pathogenic bacteria of the genus *Xanthomonas* are known to cause many diseases in important crop plants. Pathogenicity of *Xanthomonas* depends on a conserved type III secretion (T3S) system which injects more than 25 different effector proteins into the plant cell. Among these injected proteins are transcription activator-like effectors (TALE) which mimic plant transcriptional activators and manipulate the plant transcriptome (see Kay et al (2007) *Science* 318:648-651). These proteins contain a DNA binding domain and a transcriptional activation domain. One of the most well characterized TALEs is AvrBs3 from *Xanthomonas campestgris* pv. *Vesicatoria* (see Bonas et al (1989) *Mol Gen Genet* 218: 127-136 and WO2010079430). TALEs contain a centralized domain of tandem repeats, each repeat containing approximately 34 amino acids, which are key to the DNA binding specificity of these proteins. In addition, they contain a nuclear localization sequence and an acidic transcriptional activation domain (for a review see Schornack S, et al (2006) *J Plant Physiol* 163(3): 256-272). In addition, in the phytopathogenic bacteria *Ralstonia solanacearum* two genes, designated brg11 and hpx17 have been found that are homologous to the AvrBs3 family of *Xanthomonas* in the *R. solanacearum* biovar 1 strain GMI1000 and in the biovar 4 strain RS1000 (See Heuer et al (2007) *Appl and Envir Micro* 73(13): 4379-4384). These genes are 98.9% identical in nucleotide sequence to each other but differ by a deletion of 1,575 bp in the repeat domain of hpx17. However, both gene products have less than 40% sequence identity with AvrBs3 family proteins of *Xanthomonas*.

Thus, in some embodiments, the DNA binding domain that binds to a target site in a target locus (e.g., albumin or safe harbor) is an engineered domain from a TALE similar to those derived from the plant pathogens *Xanthomonas* (see Boch et al, (2009) *Science* 326: 1509-1512 and Moscou and Bogdanove, (2009) *Science* 326: 1501) and Ralstonia (see Heuer et al (2007) *Applied and Environmental Microbiology* 73(13): 4379-4384); U.S. Patent Publication No. 2011/0301073 and U.S. Patent Publication No. 20110145940.

In certain embodiments, the DNA binding domain comprises a zinc finger protein (e.g., a zinc finger protein that binds to a target site in an albumin or safe-harbor gene). Preferably, the zinc finger protein is non-naturally occurring in that it is engineered to bind to a target site of choice. See, for example, See, for example, Beerli et al. (2002) *Nature Biotechnol.* 20:135-141; Pabo et al. (2001) *Ann. Rev. Biochem.* 70:313-340; Isalan et al. (2001) *Nature Biotechnol.* 19:656-660; Segal et al. (2001) *Curr. Opin. Biotechnol.* 12:632-637; Choo et al. (2000) *Curr. Opin. Struct. Biol.* 10:411-416; U.S. Pat. Nos. 6,453,242; 6,534,261; 6,599,692; 6,503,717; 6,689,558; 7,030,215; 6,794,136; 7,067,317; 7,262,054; 7,070,934; 7,361,635; 7,253,273; and U.S. Patent Publication Nos. 2005/0064474; 2007/0218528; 2005/0267061, all incorporated herein by reference in their entireties.

An engineered zinc finger binding or TALE domain can have a novel binding specificity, compared to a naturally-occurring zinc finger protein. Engineering methods include, but are not limited to, rational design and various types of selection. Rational design includes, for example, using databases comprising triplet (or quadruplet) nucleotide sequences and individual zinc finger amino acid sequences, in which each triplet or quadruplet nucleotide sequence is associated with one or more amino acid sequences of zinc fingers which bind the particular triplet or quadruplet sequence. See, for example, co-owned U.S. Pat. Nos. 6,453,242 and 6,534,261, incorporated by reference herein in their entireties.

Exemplary selection methods, including phage display and two-hybrid systems, are disclosed in U.S. Pat. Nos. 5,789,538; 5,925,523; 6,007,988; 6,013,453; 6,410,248; 6,140,466; 6,200,759; and 6,242,568; as well as WO 98/37186; WO 98/53057; WO 00/27878; WO 01/88197 and GB 2,338,237. In addition, enhancement of binding specificity for zinc finger binding domains has been described, for example, in co-owned WO 02/077227.

In addition, as disclosed in these and other references, DNA-binding domains (e.g., multi-finger zinc finger proteins or TALE domains) may be linked together using any suitable linker sequences, including for example, linkers of 5 or more amino acids in length. See, also, U.S. Pat. Nos. 6,479,626; 6,903,185; and 7,153,949 for exemplary linker sequences 6 or more amino acids in length. The DNA binding proteins described herein may include any combination of suitable linkers between the individual zinc fingers of the protein. In addition, enhancement of binding specificity for zinc finger binding domains has been described, for example, in co-owned WO 02/077227.

Selection of target sites; DNA-binding domains and methods for design and construction of fusion proteins (and polynucleotides encoding same) are known to those of skill in the art and described in detail in U.S. Pat. Nos. 6,140,0815; 789,538; 6,453,242; 6,534,261; 5,925,523; 6,007,988; 6,013,453; 6,200,759; WO 95/19431; WO 96/06166; WO 98/53057; WO 98/54311; WO 00/27878; WO 01/60970 WO 01/88197; WO 02/099084; WO 98/53058; WO 98/53059; WO 98/53060; WO 02/016536 and WO 03/016496 and U.S. Publication No. 20110301073.

In addition, as disclosed, in these and other references, DNA-binding domains (e.g., multi-finger zinc finger proteins) may be linked together using any suitable linker sequences, including for example, linkers of 5 or more amino acids in length. See, also, U.S. Pat. Nos. 6,479,626; 6,903,185; and 7,153,949 for exemplary linker sequences 6 or more amino acids in length. The proteins described herein may include any combination of suitable linkers between the individual zinc fingers of the protein.

B. Cleavage Domains

Any suitable cleavage domain can be operatively linked to a DNA-binding domain to form a nuclease. For example, ZFP DNA-binding domains have been fused to nuclease domains to create ZFNs—a functional entity that is able to recognize its intended nucleic acid target through its engineered (ZFP) DNA binding domain and cause the DNA to be cut near the ZFP binding site via the nuclease activity. See, e.g., Kim et al. (1996) *Proc Nat'l Acad Sci USA* 93(3):1156-1160. More recently, ZFNs have been used for genome modification in a variety of organisms. See, for example, United States Patent Publications 20030232410; 20050208489; 20050026157; 20050064474; 20060188987; 20060063231; and International Publication WO 07/014,275. Likewise, TALE DNA-binding domains have been fused to nuclease domains to create TALENs. See, e.g., U.S. Publication No. 20110301073.

As noted above, the cleavage domain may be heterologous to the DNA-binding domain, for example a zinc finger DNA-binding domain and a cleavage domain from a nuclease or a TALEN DNA-binding domain and a cleavage domain, or meganuclease DNA-binding domain and cleavage domain from a different nuclease. Heterologous cleavage domains can be obtained from any endonuclease or exonuclease. Exemplary endonucleases from which a cleavage domain can be derived include, but are not limited to, restriction endonucleases and homing endonucleases. See, for example, 2002-2003 Catalogue, New England Biolabs, Beverly, Mass.; and Belfort et al. (1997) *Nucleic Acids Res.* 25:3379-3388. Additional enzymes which cleave DNA are known (e.g., 51 Nuclease; mung bean nuclease; pancreatic DNase I; micrococcal nuclease; yeast HO endonuclease; see also Linn et al. (eds.) *Nucleases*, Cold Spring Harbor Laboratory Press, 1993). One or more of these enzymes (or functional fragments thereof) can be used as a source of cleavage domains and cleavage half-domains.

Similarly, a cleavage half-domain can be derived from any nuclease or portion thereof, as set forth above, that requires dimerization for cleavage activity. In general, two fusion proteins are required for cleavage if the fusion proteins comprise cleavage half-domains. Alternatively, a single protein comprising two cleavage half-domains can be used. The two cleavage half-domains can be derived from the same endonuclease (or functional fragments thereof), or each cleavage half-domain can be derived from a different endonuclease (or functional fragments thereof). In addition, the target sites for the two fusion proteins are preferably disposed, with respect to each other, such that binding of the two fusion proteins to their respective target sites places the cleavage half-domains in a spatial orientation to each other that allows the cleavage half-domains to form a functional cleavage domain, e.g., by dimerizing. Thus, in certain embodiments, the near edges of the target sites are separated by 5-8 nucleotides or by 15-18 nucleotides. However any integral {why are we always using the qualifiers "integral" and "integer"—are these really necessary? They just seem restrictive and their use would seem to open us up to workarounds}. number of nucleotides or nucleotide pairs can intervene between two target sites (e.g., from 2 to 50 nucleotide pairs or more). In general, the site of cleavage lies between the target sites.

Restriction endonucleases (restriction enzymes) are present in many species and are capable of sequence-specific binding to DNA (at a recognition site), and cleaving DNA at or near the site of binding. Certain restriction enzymes (e.g., Type IIS) cleave DNA at sites removed from the recognition site and have separable binding and cleavage domains. For example, the Type IIS enzyme Fok I catalyzes double-stranded cleavage of DNA, at 9 nucleotides from its recognition site on one strand and 13 nucleotides from its recognition site on the other. See, for example, U.S. Pat. Nos. 5,356,802; 5,436,150 and 5,487,994; as well as Li et al. (1992) *Proc. Natl. Acad. Sci. USA* 89:4275-4279; Li et al. (1993) *Proc. Natl. Acad. Sci. USA* 90:2764-2768; Kim et al. (1994a) *Proc. Natl. Acad. Sci. USA* 91:883-887; Kim et al. (1994b) *J. Biol. Chem.* 269:31,978-31,982. Thus, in one embodiment, fusion proteins comprise the cleavage domain (or cleavage half-domain) from at least one Type IIS restriction enzyme and one or more zinc finger binding domains, which may or may not be engineered.

An exemplary Type IIS restriction enzyme, whose cleavage domain is separable from the binding domain, is Fok I. This particular enzyme is active as a dimer. Bitinaite et al. (1998) *Proc. Natl. Acad. Sci. USA* 95: 10,570-10,575. Accordingly, for the purposes of the present disclosure, the portion of the Fok I enzyme used in the disclosed fusion proteins is considered a cleavage half-domain. Thus, for targeted double-stranded cleavage and/or targeted replacement of cellular sequences using zinc finger-Fok I fusions, two fusion proteins, each comprising a FokI cleavage half-domain, can be used to reconstitute a catalytically active cleavage domain. Alternatively, a single polypeptide molecule containing a DNA binding domain and two Fok I cleavage half-domains can also be used.

A cleavage domain or cleavage half-domain can be any portion of a protein that retains cleavage activity, or that retains the ability to multimerize (e.g., dimerize) to form a functional cleavage domain.

Exemplary Type IIS restriction enzymes are described in International Publication WO 07/014,275, incorporated herein in its entirety. Additional restriction enzymes also contain separable binding and cleavage domains, and these are contemplated by the present disclosure. See, for example, Roberts et al. (2003) *Nucleic Acids Res.* 31:418-420.

In certain embodiments, the cleavage domain comprises one or more engineered cleavage half-domain (also referred to as dimerization domain mutants) that minimize or prevent homodimerization, as described, for example, in U.S. Patent Publication Nos. 20050064474; 20060188987; 20080131962 and 20110201055, the disclosures of all of which are incorporated by reference in their entireties herein. Amino acid residues at positions 446, 447, 479, 483, 484, 486, 487, 490, 491, 496, 498, 499, 500, 531, 534, 537, and 538 of Fok I are all targets for influencing dimerization of the Fok I cleavage half-domains.

Exemplary engineered cleavage half-domains of Fok I that form obligate heterodimers include a pair in which a first cleavage half-domain includes mutations at amino acid residues at positions 490 and 538 of Fok I and a second cleavage half-domain includes mutations at amino acid residues 486 and 499.

Thus, in one embodiment, a mutation at 490 replaces Glu (E) with Lys (K); the mutation at 538 replaces Iso (I) with Lys (K); the mutation at 486 replaced Gln (Q) with Glu (E); and the mutation at position 499 replaces Iso (I) with Lys (K). Specifically, the engineered cleavage half-domains described herein were prepared by mutating positions 490 (E→K) and 538 (I→K) in one cleavage half-domain to produce an engineered cleavage half-domain designated "E490K:I538K" and by mutating positions 486 (Q→E) and 499 (I→L) in another cleavage half-domain to produce an engineered cleavage half-domain designated "Q486E:I499L". The engineered cleavage half-domains described herein are obligate heterodimer mutants in which aberrant cleavage is minimized or abolished. See, e.g., U.S. Patent Publication No. 2008/0131962, the disclosure of which is incorporated by reference in its entirety for all purposes.

In certain embodiments, the engineered cleavage half-domain comprises mutations at positions 486, 499 and 496 (numbered relative to wild-type FokI), for instance mutations that replace the wild type Gln (Q) residue at position 486 with a Glu (E) residue, the wild type Iso (I) residue at position 499 with a Leu (L) residue and the wild-type Asn (N) residue at position 496 with an Asp (D) or Glu (E) residue (also referred to as a "ELD" and "ELE" domains, respectively). In other embodiments, the engineered cleavage half-domain comprises mutations at positions 490, 538 and 537 (numbered relative to wild-type FokI), for instance mutations that replace the wild type Glu (E) residue at position 490 with a Lys (K) residue, the wild type Iso (I) residue at position 538 with a Lys (K) residue, and the wild-type His (H) residue at position 537 with a Lys (K) residue or a Arg (R) residue (also referred to as "KKK" and "KKR" domains, respectively). In other embodiments, the engineered cleavage half-domain comprises mutations at positions 490 and 537 (numbered relative to wild-type FokI), for instance mutations that replace the wild type Glu (E) residue at position 490 with a Lys (K) residue and the wild-type His (H) residue at position 537 with a Lys (K) residue or a Arg (R) residue (also referred to as "KIK" and "KIR" domains, respectively). (See US Patent Publication No. 20110201055). Engineered cleavage half-domains described herein can be prepared using any suitable method, for example, by site-directed mutagenesis of wild-type cleavage half-domains (Fok I) as described in U.S. Patent Publication Nos. 20050064474; 20080131962 and 20110201055.

Alternatively, nucleases may be assembled in vivo at the nucleic acid target site using so-called "split-enzyme" technology (see e.g. U.S. Patent Publication No. 20090068164). Components of such split enzymes may be expressed either on separate expression constructs, or can be linked in one open reading frame where the individual components are separated, for example, by a self-cleaving 2A peptide or IRES sequence. Components may be individual zinc finger binding domains or domains of a meganuclease nucleic acid binding domain.

Nucleases can be screened for activity prior to use, for example in a yeast-based chromosomal system as described in WO 2009/042163 and 20090068164. Nuclease expression constructs can be readily designed using methods known in the art. See, e.g., United States Patent Publications 20030232410; 20050208489; 20050026157; 20050064474; 20060188987; 20060063231; and International Publication WO 07/014,275. Expression of the nuclease may be under the control of a constitutive promoter or an inducible promoter, for example the galactokinase promoter which is activated (de-repressed) in the presence of raffinose and/or galactose and repressed in presence of glucose.

Target Sites

As described in detail above, DNA domains can be engineered to bind to any sequence of choice in a locus, for example an albumin or safe-harbor gene. An engineered DNA-binding domain can have a novel binding specificity, compared to a naturally-occurring DNA-binding domain. Engineering methods include, but are not limited to, rational design and various types of selection. Rational design includes, for example, using databases comprising triplet (or quadruplet) nucleotide sequences and individual (e.g., zinc finger) amino acid sequences, in which each triplet or quadruplet nucleotide sequence is associated with one or more amino acid sequences of DNA binding domain which bind the particular triplet or quadruplet sequence. See, for example, co-owned U.S. Pat. Nos. 6,453,242 and 6,534,261, incorporated by reference herein in their entireties. Rational design of TAL-effector domains can also be performed. See, e.g., U.S. Patent Publication No. 20110301073.

Exemplary selection methods applicable to DNA-binding domains, including phage display and two-hybrid systems, are disclosed in U.S. Pat. Nos. 5,789,538; 5,925,523; 6,007,988; 6,013,453; 6,410,248; 6,140,466; 6,200,759; and 6,242,568; as well as WO 98/37186; WO 98/53057; WO 00/27878; WO 01/88197 and GB 2,338,237.

Selection of target sites; nucleases and methods for design and construction of fusion proteins (and polynucleotides encoding same) are known to those of skill in the art and described in detail in U.S. Patent Application Publication Nos. 20050064474 and 20060188987, incorporated by reference in their entireties herein.

In addition, as disclosed in these and other references, DNA-binding domains (e.g., multi-finger zinc finger proteins) may be linked together using any suitable linker sequences, including for example, linkers of 5 or more amino acids. See, e.g., U.S. Pat. Nos. 6,479,626; 6,903,185; and 7,153,949 for exemplary linker sequences 6 or more amino acids in length. The proteins described herein may include any combination of suitable linkers between the individual DNA-binding domains of the protein. See, also, U.S. Publication No. 20110301073.

Donors

As noted above, insertion of an exogenous sequence (also called a "donor sequence" or "donor"), for example for correction of a mutant gene or for increased expression of a wild-type gene. It will be readily apparent that the donor sequence is typically not identical to the genomic sequence where it is placed. A donor sequence can contain a non-homologous sequence flanked by two regions of homology to allow for efficient HDR at the location of interest. Additionally, donor sequences can comprise a vector molecule containing sequences that are not homologous to the region of interest in cellular chromatin. A donor molecule can contain several, discontinuous regions of homology to cellular chromatin. For example, for targeted insertion of sequences not normally present in a region of interest, said sequences can be present in a donor nucleic acid molecule and flanked by regions of homology to sequence in the region of interest.

The donor polynucleotide can be DNA or RNA, single-stranded or double-stranded and can be introduced into a cell in linear or circular form. See, e.g., U.S. Patent Publication Nos. 20100047805 and 20110207221. If introduced in linear form, the ends of the donor sequence can be protected (e.g., from exonucleolytic degradation) by methods known to those of skill in the art. For example, one or more dideoxynucleotide residues are added to the 3' terminus of a linear molecule and/or self-complementary oligonucleotides are ligated to one or both ends. See, for example, Chang et al. (1987) *Proc. Natl. Acad. Sci. USA* 84:4959-4963; Nehls et al. (1996) *Science* 272:886-889. Additional methods for protecting exogenous polynucleotides from degradation include, but are not limited to, addition of terminal amino group(s) and the use of modified internucleotide linkages such as, for example, phosphorothioates, phosphoramidates, and O-methyl ribose or deoxyribose residues.

A polynucleotide can be introduced into a cell as part of a vector molecule having additional sequences such as, for example, replication origins, promoters and genes encoding antibiotic resistance. Moreover, donor polynucleotides can be introduced as naked nucleic acid, as nucleic acid complexed with an agent such as a liposome or poloxamer, or can be delivered by viruses (e.g., adenovirus, AAV, herpesvirus, retrovirus, lentivirus and integrase defective lentivirus (IDLV)).

The donor is generally inserted so that its expression is driven by the endogenous promoter at the integration site, namely the promoter that drives expression of the albumin gene. However, it will be apparent that the donor may comprise a promoter and/or enhancer, for example a constitutive promoter or an inducible or tissue specific promoter.

The donor molecule may be inserted into an endogenous gene such that all, some or none of the endogenous gene is expressed. For example, a transgene as described herein may be inserted into an albumin locus such that some or none of the endogenous albumin sequences are expressed, for example as a fusion with the transgene. In other embodiments, the transgene (e.g., with or without albumin encoding sequences) is integrated into any endogenous locus, for example a safe-harbor locus. See, e.g., US patent publications 20080299580; 20080159996 and 201000218264.

When albumin sequences (endogenous or part of the transgene) are expressed with the transgene, the albumin sequences may be full-length sequences (wild-type or mutant) or partial sequences. Preferably the albumin sequences are functional. Non-limiting examples of the function of these full length or partial albumin sequences include increasing the serum half-life of the polypeptide expressed by the transgene (e.g., therapeutic gene) and/or acting as a carrier.

Furthermore, although not required for expression, exogenous sequences may also include transcriptional or translational regulatory sequences, for example, promoters, enhancers, insulators, internal ribosome entry sites, sequences encoding 2A peptides and/or polyadenylation signals.

Delivery

The nucleases, polynucleotides encoding these nucleases, donor polynucleotides and compositions comprising the proteins and/or polynucleotides described herein may be delivered in vivo or ex vivo by any suitable means.

Methods of delivering nucleases as described herein are described, for example, in U.S. Pat. Nos. 6,453,242; 6,503,717; 6,534,261; 6,599,692; 6,607,882; 6,689,558; 6,824,978; 6,933,113; 6,979,539; 7,013,219; and 7,163,824, the disclosures of all of which are incorporated by reference herein in their entireties.

Nucleases and/or donor constructs as described herein may also be delivered using vectors containing sequences encoding one or more of the zinc finger or TALEN protein(s). Any vector systems may be used including, but not limited to, plasmid vectors, retroviral vectors, lentiviral vectors, adenovirus vectors, poxvirus vectors; herpesvirus vectors and adeno-associated virus vectors, etc. See, also, U.S. Pat. Nos. 6,534,261; 6,607,882; 6,824,978; 6,933,113; 6,979,539; 7,013,219; and 7,163,824, incorporated by reference herein in their entireties. Furthermore, it will be apparent that any of these vectors may comprise one or more of the sequences needed for treatment. Thus, when one or more nucleases and a donor construct are introduced into the cell, the nucleases and/or donor polynucleotide may be carried on the same vector or on different vectors. When multiple vectors are used, each vector may comprise a sequence encoding one or multiple nucleases and/or donor constructs.

Conventional viral and non-viral based gene transfer methods can be used to introduce nucleic acids encoding nucleases and donor constructs in cells (e.g., mammalian cells) and target tissues. Non-viral vector delivery systems include DNA plasmids, naked nucleic acid, and nucleic acid complexed with a delivery vehicle such as a liposome or poloxamer. Viral vector delivery systems include DNA and RNA viruses, which have either episomal or integrated genomes after delivery to the cell. For a review of gene therapy procedures, see Anderson, *Science* 256:808-813 (1992); Nabel & Feigner, *TIBTECH* 11:211-217 (1993); Mitani & Caskey, *TIBTECH* 11:162-166 (1993); Dillon, *TIBTECH* 11:167-175 (1993); Miller, *Nature* 357:455-460 (1992); Van Brunt, *Biotechnology* 6(10):1149-1154 (1988); Vigne, *Restorative Neurology and Neuroscience* 8:35-36 (1995); Kremer & Perricaudet, *British Medical Bulletin* 51(1):31-44 (1995); Haddada et al., in *Current Topics in Microbiology and Immunology* Doerfler and Bohm (eds.) (1995); and Yu et al., *Gene Therapy* 1:13-26 (1994).

Methods of non-viral delivery of nucleic acids include electroporation, lipofection, microinjection, biolistics, virosomes, liposomes, immunoliposomes, polycation or lipid:nucleic acid conjugates, naked DNA, artificial virions, and agent-enhanced uptake of DNA. Sonoporation using, e.g., the Sonitron 2000 system (Rich-Mar) can also be used for delivery of nucleic acids.

Additional exemplary nucleic acid delivery systems include those provided by Amaxa Biosystems (Cologne, Germany), Maxcyte, Inc. (Rockville, Md.), BTX Molecular Delivery Systems (Holliston, Mass.) and Copernicus Therapeutics Inc, (see for example U.S. Pat. No. 6,008,336). Lipofection is described in e.g., U.S. Pat. Nos. 5,049,386; 4,946,787; and 4,897,355) and lipofection reagents are sold commercially (e.g., Transfectam™ and Lipofectin™). Cationic and neutral lipids that are suitable for efficient receptor-recognition lipofection of polynucleotides include those of Feigner, WO 91/17424, WO 91/16024.

The preparation of lipid:nucleic acid complexes, including targeted liposomes such as immunolipid complexes, is well known to one of skill in the art (see, e.g., Crystal, *Science* 270:404-410 (1995); Blaese et al., *Cancer Gene Ther.* 2:291-297 (1995); Behr et al., *Bioconjugate Chem.* 5:382-389 (1994); Remy et al., *Bioconjugate Chem.* 5:647-654 (1994); Gao et al., *Gene Therapy* 2:710-722 (1995); Ahmad et al., *Cancer Res.* 52:4817-4820 (1992); U.S. Pat. Nos. 4,186,183, 4,217,344, 4,235,871, 4,261,975, 4,485,054, 4,501,728, 4,774,085, 4,837,028, and 4,946,787).

Additional methods of delivery include the use of packaging the nucleic acids to be delivered into EnGeneIC delivery vehicles (EDVs). These EDVs are specifically delivered to target tissues using bispecific antibodies where one arm of the antibody has specificity for the target tissue and the other has specificity for the EDV. The antibody brings the EDVs to the target cell surface and then the EDV is brought into the cell by endocytosis. Once in the cell, the contents are released (see MacDiarmid et al (2009) *Nature Biotechnology* 27(7):643).

The use of RNA or DNA viral based systems for the delivery of nucleic acids encoding engineered ZFPs take advantage of highly evolved processes for targeting a virus to specific cells in the body and trafficking the viral payload to the nucleus. Viral vectors can be administered directly to patients (in vivo) or they can be used to treat cells in vitro and the modified cells are administered to patients (ex vivo). Conventional viral based systems for the delivery of ZFPs include, but are not limited to, retroviral, lentivirus, adenoviral, adeno-associated, vaccinia and herpes simplex virus vectors for gene transfer. Integration in the host genome is possible with the retrovirus, lentivirus, and adeno-associated virus gene transfer methods, often resulting in long term expression of the inserted transgene. Additionally, high transduction efficiencies have been observed in many different cell types and target tissues.

The tropism of a retrovirus can be altered by incorporating foreign envelope proteins, expanding the potential target population of target cells. Lentiviral vectors are retroviral vectors that are able to transduce or infect non-dividing cells and typically produce high viral titers. Selection of a retroviral gene transfer system depends on the target tissue. Retroviral vectors are comprised of cis-acting long terminal repeats with packaging capacity for up to 6-10 kb of foreign sequence. The minimum cis-acting LTRs are sufficient for replication and packaging of the vectors, which are then used to integrate the therapeutic gene into the target cell to provide permanent transgene expression. Widely used retroviral vectors include those based upon murine leukemia virus (MuLV), gibbon ape leukemia virus (GaLV), Simian Immunodeficiency virus (SIV), human immunodeficiency virus (HIV), and combinations thereof (see, e.g., Buchscher et al., *J. Virol.* 66:2731-2739 (1992); Johann et al., *J. Virol.* 66:1635-1640 (1992); Sommerfelt et al., *Virol.* 176:58-59 (1990); Wilson et al., *J. Virol.* 63:2374-2378 (1989); Miller et al., *J. Virol.* 65:2220-2224 (1991); PCT/US94/05700).

In applications in which transient expression is preferred, adenoviral based systems can be used. Adenoviral based vectors are capable of very high transduction efficiency in many cell types and do not require cell division. With such vectors, high titer and high levels of expression have been obtained. This vector can be produced in large quantities in a relatively simple system. Adeno-associated virus ("AAV") vectors are also used to transduce cells with target nucleic acids, e.g., in the in vitro production of nucleic acids and peptides, and for in vivo and ex vivo gene therapy procedures (see, e.g., West et al., *Virology* 160:38-47 (1987); U.S. Pat. No. 4,797,368; WO 93/24641; Kotin, *Human Gene Therapy* 5:793-801 (1994); Muzyczka, *J. Clin. Invest.* 94:1351 (1994). Construction of recombinant AAV vectors is described in a number of publications, including U.S. Pat. No. 5,173,414; Tratschin et al., *Mol. Cell. Biol.* 5:3251-3260 (1985); Tratschin, et al., *Mol. Cell. Biol.* 4:2072-2081 (1984); Hermonat & Muzyczka, *PNAS* 81:6466-6470 (1984); and Samulski et al., *J. Virol.* 63:03822-3828 (1989).

At least six viral vector approaches are currently available for gene transfer in clinical trials, which utilize approaches that involve complementation of defective vectors by genes inserted into helper cell lines to generate the transducing agent.

pLASN and MFG-S are examples of retroviral vectors that have been used in clinical trials (Dunbar et al., *Blood* 85:3048-305 (1995); Kohn et al., *Nat. Med.* 1:1017-102 (1995); Malech et al., *PNAS* 94:22 12133-12138 (1997)). PA317/pLASN was the first therapeutic vector used in a gene therapy trial. (Blaese et al., *Science* 270:475-480 (1995)). Transduction efficiencies of 50% or greater have been observed for MFG-S packaged vectors. (Ellem et al., *Immunol Immunother.* 44(1):10-20 (1997); Dranoff et al., *Hum. Gene Ther.* 1:111-2 (1997).

Recombinant adeno-associated virus vectors (rAAV) are a promising alternative gene delivery systems based on the defective and nonpathogenic parvovirus adeno-associated type 2 virus. All vectors are derived from a plasmid that retains only the AAV 145 bp inverted terminal repeats flanking the transgene expression cassette. Efficient gene transfer and stable transgene delivery due to integration into the genomes of the transduced cell are key features for this vector system. (Wagner et al., *Lancet* 351:9117 1702-3 (1998), Kearns et al., *Gene Ther.* 9:748-55 (1996)). Other AAV serotypes, including AAV1, AAV3, AAV4, AAV5, AAV6, AAV8, AAV 8.2, AAV9, AAV rh10 and pseudotyped AAV such as AAV2/8, AAV2/5 and AAV2/6 can also be used in accordance with the present invention.

Replication-deficient recombinant adenoviral vectors (Ad) can be produced at high titer and readily infect a number of different cell types. Most adenovirus vectors are engineered such that a transgene replaces the Ad E1a, E1b, and/or E3 genes; subsequently the replication defective vector is propagated in human 293 cells that supply deleted gene function in trans. Ad vectors can transduce multiple types of tissues in vivo, including non-dividing, differentiated cells such as those found in liver, kidney and muscle. Conventional Ad vectors have a large carrying capacity. An example of the use of an Ad vector in a clinical trial involved polynucleotide therapy for anti-tumor immunization with intramuscular injection (Sterman et al., *Hum. Gene Ther.* 7:1083-9 (1998)). Additional examples of the use of adenovirus vectors for gene transfer in clinical trials include Rosenecker et al., *Infection* 24:1 5-10 (1996); Sterman et al., *Hum. Gene Ther.* 9:7 1083-1089 (1998); Welsh et al., *Hum. Gene Ther.* 2:205-18 (1995); Alvarez et al., *Hum. Gene Ther.* 5:597-613 (1997); Topf et al., *Gene Ther.* 5:507-513 (1998); Sterman et al., *Hum. Gene Ther.* 7:1083-1089 (1998).

Packaging cells are used to form virus particles that are capable of infecting a host cell. Such cells include 293 cells, which package adenovirus, and ψ2 cells or PA317 cells, which package retrovirus. Viral vectors used in gene therapy are usually generated by a producer cell line that packages a nucleic acid vector into a viral particle. The vectors typically contain the minimal viral sequences required for packaging and subsequent integration into a host (if applicable), other viral sequences being replaced by an expression cassette encoding the protein to be expressed. The missing viral functions are supplied in trans by the packaging cell line. For example, AAV vectors used in gene therapy typically only possess inverted terminal repeat (ITR) sequences from the AAV genome which are required for packaging and integration into the host genome. Viral DNA is packaged in a cell line, which contains a helper plasmid encoding the other AAV genes, namely rep and cap, but lacking ITR sequences. The cell line is also infected with adenovirus as a helper. The helper virus promotes replication of the AAV vector and expression of AAV genes from the helper plasmid. The helper plasmid is not packaged in significant amounts due to a lack of ITR sequences. Contamination with adenovirus can be reduced by, e.g., heat treatment to which adenovirus is more sensitive than AAV.

In many gene therapy applications, it is desirable that the gene therapy vector be delivered with a high degree of specificity to a particular tissue type. Accordingly, a viral vector can be modified to have specificity for a given cell type by expressing a ligand as a fusion protein with a viral coat protein on the outer surface of the virus. The ligand is chosen to have affinity for a receptor known to be present on the cell type of interest. For example, Han et al., *Proc. Natl. Acad. Sci. USA* 92:9747-9751 (1995), reported that Moloney murine leukemia virus can be modified to express human heregulin fused to gp70, and the recombinant virus infects certain human breast cancer cells expressing human epidermal growth factor receptor. This principle can be extended to other virus-target cell pairs, in which the target cell expresses a receptor and the virus expresses a fusion protein comprising a ligand for the cell-surface receptor. For example, filamentous phage can be engineered to display antibody fragments (e.g., FAB or Fv) having specific binding affinity for virtually any chosen cellular receptor. Although the above description applies primarily to viral vectors, the same principles can be applied to nonviral vectors. Such vectors can be engineered to contain specific uptake sequences which favor uptake by specific target cells.

Gene therapy vectors can be delivered in vivo by administration to an individual patient, typically by systemic administration (e.g., intravenous, intraperitoneal, intramuscular, subdermal, or intracranial infusion) or topical application, as described below. Alternatively, vectors can be delivered to cells ex vivo, such as cells explanted from an individual patient (e.g., lymphocytes, bone marrow aspirates, tissue biopsy) or universal donor hematopoietic stem cells, followed by reimplantation of the cells into a patient, usually after selection for cells which have incorporated the vector.

Vectors (e.g., retroviruses, adenoviruses, liposomes, etc.) containing nucleases and/or donor constructs can also be administered directly to an organism for transduction of cells in vivo. Alternatively, naked DNA can be administered. Administration is by any of the routes normally used for introducing a molecule into ultimate contact with blood or tissue cells including, but not limited to, injection, infusion, topical application and electroporation. Suitable methods of administering such nucleic acids are available and well known to those of skill in the art, and, although more than one route can be used to administer a particular composition, a particular route can often provide a more immediate and more effective reaction than another route.

Vectors suitable for introduction of polynucleotides described herein include non-integrating lentivirus vectors (IDLV). See, for example, Ory et al. (1996) *Proc. Natl. Acad. Sci. USA* 93:11382-11388; Dull et al. (1998) *J. Virol.* 72:8463-8471; Zuffery et al. (1998) *J. Virol.* 72:9873-9880; Follenzi et al. (2000) *Nature Genetics* 25:217-222; U.S. Patent Publication No 2009/054985.

Pharmaceutically acceptable carriers are determined in part by the particular composition being administered, as well as by the particular method used to administer the composition. Accordingly, there is a wide variety of suitable formulations of pharmaceutical compositions available, as described below (see, e.g., *Remington's Pharmaceutical Sciences*, 17th ed., 1989).

It will be apparent that the nuclease-encoding sequences and donor constructs can be delivered using the same or different systems. For example, a donor polynucleotide can be carried by a plasmid, while the one or more nucleases can be carried by a AAV vector. Furthermore, the different vectors can be administered by the same or different routes (intramuscular injection, tail vein injection, other intravenous injection, intraperitoneal administration and/or intramuscular injection. The vectors can be delivered simultaneously or in any sequential order.

Formulations for both ex vivo and in vivo administrations include suspensions in liquid or emulsified liquids. The active ingredients often are mixed with excipients which are pharmaceutically acceptable and compatible with the active ingredient. Suitable excipients include, for example, water, saline, dextrose, glycerol, ethanol or the like, and combinations thereof. In addition, the composition may contain minor amounts of auxiliary substances, such as, wetting or emulsifying agents, pH buffering agents, stabilizing agents or other reagents that enhance the effectiveness of the pharmaceutical composition.

Applications

The methods and compositions of the invention can be used in any circumstance wherein it is desired to supply a transgene encoding one or more proteins such that the protein(s) is(are) secreted from the targeted cell. Thus, this technology is of use in a condition where a patient is deficient in some protein due to problems (e.g., problems in expression level or problems with the protein expressed as sub- or non-functioning). Particularly useful with this invention is the expression of transgenes to correct or restore functionality in clotting disorders. Additionally, A1AT-deficiency disorders such as COPD or liver damage, or other disorders, conditions or diseases that can be mitigated by the supply of exogenous proteins by a secretory organ may be successfully treated by the methods and compositions of this invention. Lysosomal storage diseases can be treated by the methods and compositions of the invention, as are metabolic diseases such as diabetes.

Proteins that are useful therapeutically and that are typically delivered by injection or infusion are also useful with the methods and compositions of the invention. By way of non-limiting examples, production of a C-peptide (e.g. Ersatta™ by Cebix) or insulin for use in diabetic therapy. A further application includes treatment of Epidermolysis Bullosa via production of collagen VII. Expression of IGF-1 in secretory tissue as described herein can be used to increase levels of this protein in patients with liver cirrhosis and lipoprotein lipase deficiency by expression of lipoprotein lipase. Antibodies may also be secreted for therapeutic benefit, for example, for the treatment of cancers, autoimmune and other diseases. Other proteins related to clotting could be produced in secretory tissue, include fibrinogen, prothrombin, tissue factor, Factor V, Factor XI, Factor XII (Hageman factor), Factor XIII (fibrin-stabilizing factor), von Willebrand factor, prekallikrein, high molecular weight kininogen (Fitzgerald factor), fibronectin, antithrombin III, heparin cofactor II, protein C, protein S, protein Z, protein Z-related protease inhibitor, plasminogen, alpha 2-antiplasmin, tissue plasminogen activator, urokinase, plasminogen activator inhibitor-1, and plasminogen activator inhibitor-2.

The following Examples relate to exemplary embodiments of the present disclosure in which the nuclease comprises a zinc finger nuclease (ZFN) or TALEN. It will be appreciated that this is for purposes of exemplification only and that other nucleases can be used, for instance homing endonucleases (meganucleases) with engineered DNA-binding domains and/or fusions of naturally occurring of engineered homing endonucleases (meganucleases) DNA-binding domains and heterologous cleavage domains.

EXAMPLES

Example 1

Design, Construction and Characterization of Zinc Finger Protein Nucleases (ZFN) Targeted to the Mouse Albumin Gene Zinc finger proteins were designed to target cleavage sites within introns 1, 12 and 13 of the mouse albumin gene. Corresponding expression constructs were assembled and incorporated into plasmids, AAV or adenoviral vectors essentially as described in Umov et al. (2005) *Nature* 435(7042): 646-651, Perez et al (2008) *Nature Biotechnology* 26(7):808-816, and as described in U.S. Pat. No. 6,534,261. Table 1 shows the recognition helices within the DNA binding domain of exemplary mouse albumin specific ZFPs while Table 2 shows the target sites for these ZFPs. Nucleotides in the target site that are contacted by the ZFP recognition helices are indicated in uppercase letters; non-contacted nucleotides indicated in lowercase.

TABLE 1

Murine albumin-specific zinc finger nucleases helix designs

| Target SBS # | F1 | F2 | F3 | F4 | F5 | F6 |
|---|---|---|---|---|---|---|
| Intron 1 30724 | TSGSLTR (SEQ ID NO: 1) | RSDALST (SEQ ID NO: 2) | QSATRTK (SEQ ID NO: 3) | TSGHLSR (SEQ ID NO: 4) | QSGNLAR (SEQ ID NO: 5) | NA |
| Intron 1 30725 | RSDHLSA (SEQ ID NO: 6) | TKSNRTK (SEQ ID NO: 7) | DRSNLSR (SEQ ID NO: 8) | WRSSLRA (SEQ ID NO: 9) | DSSDRKK (SEQ ID NO: 10) | NA |
| Intron 1 30732 | TSGNLTR (SEQ ID NO: 11) | DRSTRRQ (SEQ ID NO: 12) | TSGSLTR (SEQ ID NO: 1) | ERGTLAR (SEQ ID NO: 13) | TSANLSR (SEQ ID NO: 14) | NA |
| Intron 1 30733 | DRSALAR (SEQ ID NO: 15) | RSDHLSE (SEQ ID NO: 16) | HRSDRTR (SEQ ID NO: 17) | QSGALAR (SEQ ID NO: 18) | QSGHLSR (SEQ ID NO: 19) | NS |
| Intron 13 30759 | RSDNLST (SEQ ID NO: 20) | DRSALAR (SEQ ID NO: 15) | DRSNLSR (SEQ ID NO: 8) | DGRNLRH (SEQ ID NO: 21) | RSDNLAR (SEQ ID NO: 22) | QSNALNR (SEQ ID NO: 23) |
| Intron 13 30761 | DRSNLSR (SEQ ID NO: 8) | LKQVLVR (SEQ ID NO: 24) | QSGNLAR (SEQ ID NO: 5) | QSTPLFA (SEQ ID NO: 25) | QSGALAR (SEQ ID NO: 18) | NA |
| Intron 13 30760 | DRSNLSR (SEQ ID NO: 8) | DGRNLRH (SEQ ID NO: 21) | RSDNLAR (SEQ ID NO: 22) | QSNALNR (SEQ ID NO: 23) | NA | NA |
| Intron 13 30767 | RSDNLSV (SEQ ID NO: 26) | HSNARKT (SEQ ID NO: 27) | RSDSLSA (SEQ ID NO: 28) | QSGNLAR (SEQ ID NO: 5) | RSDSLSV (SEQ ID NO: 29) | QSGHLSR (SEQ ID NO: 19) |
| Intron 13 30768 | RSDNLSE (SEQ ID NO: 30) | ERANRNS (SEQ ID NO: 31) | QSANRTK (SEQ ID NO: 32) | ERGTLAR (SEQ ID NO: 13) | RSDALTQ (SEQ ID NO: 33) | NA |
| Intron 13 30769 | TSGSLTR (SEQ ID NO: 1) | DRSNLSR (SEQ ID NO: 8) | DGRNLRH (SEQ ID NO: 21) | ERGTLAR (SEQ ID NO: 13) | RSDALTQ (SEQ ID NO: 33) | NA |
| Intron 12 30872 | QSGHLAR (SEQ ID NO: 34) | RSDHLTQ (SEQ ID NO: 35) | RSDHLSQ (SEQ ID NO: 36) | WRSSLVA (SEQ ID NO: 37) | RSDVLSE (SEQ ID NO: 38) | RNQHRKT (SEQ ID NO: 39) |
| Intron 12 30873 | QSGDLTR (SEQ ID NO: 40) | RSDALAR (SEQ ID NO: 41) | QSGDLTR (SEQ ID NO: 40) | RRDPLIN (SEQ ID NO: 42) | RSDNLSV (SEQ ID NO: 26) | IRSTLRD (SEQ ID NO: 43) |
| Intron 12 30876 | RSDNLSV (SEQ ID NO: 26) | YSSTRNS (SEQ ID NO: 44) | RSDHLSA (SEQ ID NO: 6) | SYWSRTV (SEQ ID NO: 45) | QSSDLSR (SEQ ID NO: 46) | RTDALRG (SEQ ID NO: 47) |
| Intron 12 30877 | RSDNLST (SEQ ID NO: 20) | QKSPLNT (SEQ ID NO: 48) | TSGNLTR (SEQ ID NO: 11) | QAENLKS (SEQ ID NO: 49) | QSSDLSR (SEQ ID NO: 46) | RTDALRG (SEQ ID NO: 47) |
| Intron 12 30882 | RSDNLSV (SEQ ID NO: 26) | RRAHLNQ (SEQ ID NO: 50) | TSGNLTR (SEQ ID NO: 11) | SDTNRFK (SEQ ID NO: 51) | RSDNLST (SEQ ID NO: 20) | QSGHLSR (SEQ ID NO: 19) |
| Intron 12 30883 | DSSDRKK (SEQ ID NO: 10) | DRSALSR (SEQ ID NO: 52) | TSSNRKT (SEQ ID NO: 53) | QSGALAR (SEQ ID NO: 18) | RSDHLSR (SEQ ID NO: 54) | NA |

TABLE 2

Target sites of murine albumin-specific ZFNs

| Target | SBS # | Target site |
|---|---|---|
| Intron 1 | 30724 | ctGAAGGTgGCAATGGTTcctctotgct_ (SEQ ID NO: 55) |
| Intron 1 | 30725 | ttTCCTGTAACGATCGGgaactggcatc_ (SEQ ID NO: 56) |
| Intron 1 | 30732 | aaGATGCCaGTTCCCGATcgttacagga_ (SEQ ID NO: 57) |
| Intron 1 | 30733 | agGGAGTAGCTTAGGTCagtgaagagaa_ (SEQ ID NO: 58) |
| Intron 13 | 30759 | acGTAGAGAACAACATCTAGattggtgg_ (SEQ ID NO: 59) |
| Intron 13 | 30761 | ctGTAATAGAAACTGACttacgtagctt_ (SEQ ID NO: 60) |
| Intron 13 | 30760 | acGTAGAGAACAACatctagattggtgg_ (SEQ ID NO: 59) |
| Intron 13 | 30767 | agGGAATGtGAAATGATTCAGatatata_ (SEQ ID NO: 61) |
| Intron 13 | 30768 | ccATGGCCTAACAACAGtttatottctt_ (SEQ ID NO: 62) |
| Intron 13 | 30769 | ccATGGCCtAACAACaGTTtatcttctt_ (SEQ ID NO: 62) |
| Intron 12 | 30872 | ctTGGCTGTGTAGGAGGGGAgtagcagt_ (SEQ ID NO: 63) |
| Intron 12 | 30873 | ttCCTAAGTTGGCAGTGGCAtgottaat_ (SEQ ID NO: 64) |
| Intron 12 | 30876 | ctTTGGCTTTGAGGATTAAGcatgccac_ (SEQ ID NO: 65) |
| Intron 12 | 30877 | acTTGGCTcCAAGATTTATAGccttaaa_ (SEQ ID NO: 66) |
| Intron 12 | 30882 | caGGAAAGTAAGATAGGAAGgaatgtga_ (SEQ ID NO: 67) |
| Intron 12 | 30883 | ctGGGGTAAATGTCTCCttgctcttctt_ (SEQ ID NO: 68) |

Example 2

Activity of Murine Albumin-Specific ZFNs

The ZFNs in Table 1 were tested for the ability to cleave their endogenous target sequences in mouse cells. To accomplish this, constructs expressing the ZFNs in Table 1 were transfected into Neuro2A cells in the pairings indicated in FIG. 1. Cells were then maintained at 37° C. for 3 days or subjected to a hypothermic shock (30° C., see co-owned US Patent Publication No. 20110041195). Genomic DNA was then isolated from Neuro2A cells using the DNeasy kit (Qiagen) and subjected to the Cel-I assay (Surveyor™, Transgenomics) as described in Perez et al, (2008) *Nat. Biotechnol.* 26: 808-816 and Guschin et al, (2010) *Methods Mol Biol.* 649:247-56), in order to quantify chromosomal modifications induced by ZFN-cleavage. In this assay, PCR is used to amplify a DNA fragment bearing the ZFN target site, and then the resultant amplicon is digested with the mismatch-specific nuclease Cel-I (Yang et al, (2000) *Biochemistry* 39, 3533-3541), followed by resolution of intact and cleaved amplicon on an agarose gel. By quantifying the degree of amplicon cleavage, one may calculate the fraction of mutated alleles in amplicon and therefore in the original cellular pool. In these experiments, all ZFN pairs were ELD/KKR FokI mutation pairs (described above).

Figure 1B:
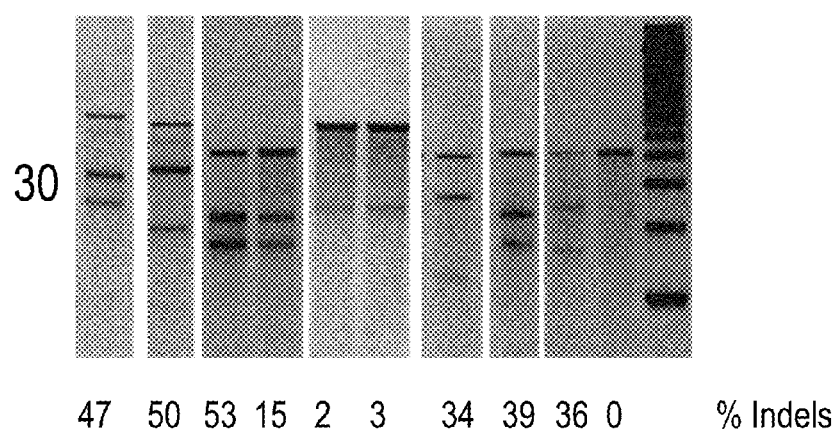
FIG. 1B shows results for the same ZFNs and cells as FIG. 1A except cells were subjected to hypothermic shock (30° C.) during their 3 days of growth following transfection. The percent mismatch, or % indels shown at the bottom of the lanes, is a measure of the ZFN activity and demonstrates that the mouse albumin specific ZFNs are able to induce up to 53% indels following cleavage of their endogenous chromosomal target in Neuro 2A cells.

Results from the Cel-I assay are shown in FIG. 1, and demonstrate that the ZFNs are capable of inducing cleavage and consequent mutations at their respective target sites. The "percent indel" value shown beneath each lane indicates the fraction of ZFN targets that were successfully cleaved and subsequently mutated during cellular repair of the double stranded break via NHEJ. The data also demonstrate increased activity when the transduction procedure incorporates the hypothermic shock.

Example 3

Canine Albumin-Specific ZFNs

A pair of ZFNs targeting the canine albumin locus was constructed for use in in vivo models. The pair was constructed as described in Example 1, and is shown below in Table 3. The target for each ZFN is provided in Table 4.

TABLE 3

Canine albumin-specific zinc finger nucleases helix designs

| Target | SBS # | F1 | F2 | F3 | F4 | F5 |
|---|---|---|---|---|---|---|
| Intron 1 | 33115 | QRSNLDS (SEQ ID NO: 83) | QSSDLSR (SEQ ID NO: 46) | YHWYLKK (SEQ ID NO: 84) | RSDDLSV (SEQ ID NO: 85) | TSSNRTK (SEQ ID NO: 86) |
| Intron 1 | 34077 | QSGNLAR (SEQ ID NO: 5) | QYTHLVA (SEQ ID NO: 87) | RSDHLST (SEQ ID NO: 88) | RSDARTT (SEQ ID NO: 89) | DRSALAR (SEQ ID NO: 15) |

TABLE 4

Target sites of canine albumin-specific ZFNs

| Target | SBS # | Target site |
|---|---|---|
| Intron 1 | 33115 | agTATTCGTTTGCTcCAAaatatttgcc (SEQ ID NO: 90) |
| Intron 1 | 34077 | aaGTCATGTGGAGAGAAacacaaagagt (SEQ ID NO: 91) |

Figure 2A:
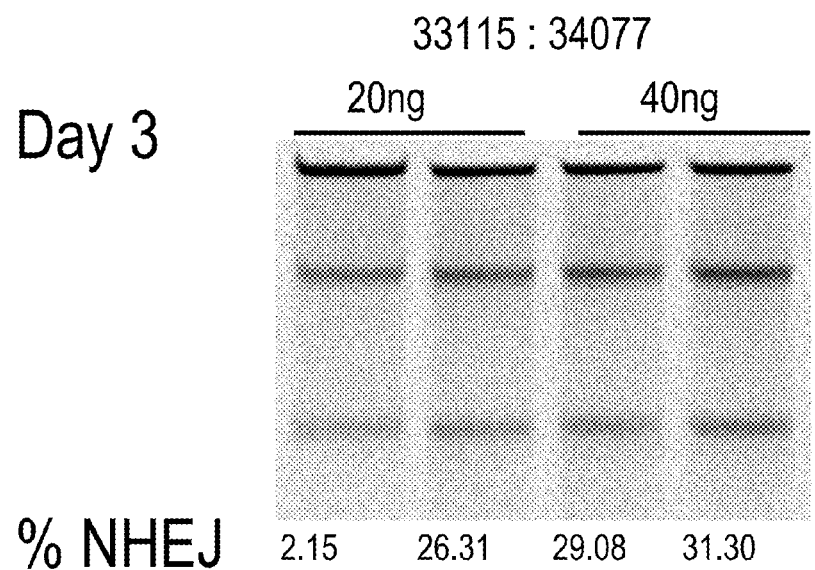
Figure 2B:
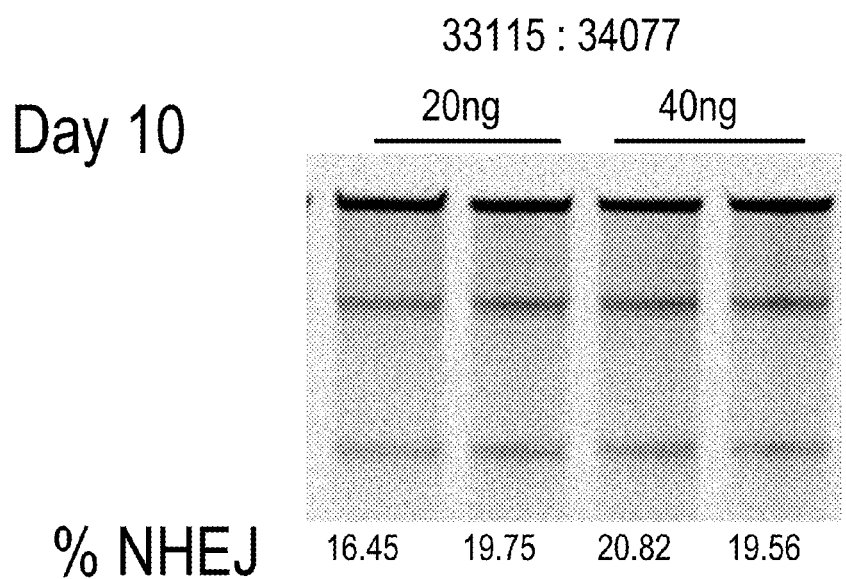
FIG. 2B depicts the results after 10 days. This ZFN pair was able to induce indels in ~25-30% of target site sequences at day 3.

The canine specific ZFNs were tested in vitro for activity essentially as described in example 2, except that the canine cell line D17 was used. As shown in FIG. 2, the ZFNs were shown to generate ~30% indels in this study.

Example 4

Non-Human Primate Albumin Specific ZFNs

ZFNs targeting the albumin locus in rhesus macaque monkeys (*Macaca mulatta*) were also made. The pairs were constructed as described above and are shown below in Table 5. The targets for the ZFNs are shown in Table 6. As shown below, the human (SEQ ID NO:92) and rhesus macaque (SEQ ID NO:93) sequences for the binding site for SBS#35396 (see below, Table 7 and 8) are perfectly conserved. The differences between the human and rhesus sequences are boxed.

```
HUMAN LEADS          35364
                              35396
HUMAN ATTGAATTCA TAACTATCCC AAAGACCTAT CCATTGCACT ATGCTTTATT TAAAAACCAC
RHESUS ATTGAATTCA TAACTGTCCC TAAGACCTAT CCATTGCACT ATGCTTTATT TAAAAGCCAC
                  G          (NOTE: G IN SOME INSTANCES)
```

Thus, for the development of the rhesus albumin specific pair, 35396 was paired with a series of partners which were designed to replace the human 35364 partner in rhesus. These proteins are shown below (Table 5) along with their target sequences (Table 6).

TABLE 5

Rhesus albumin-specific zinc finger nucleases helix designs

| | | Rhesus | | | | |
|---|---|---|---|---|---|---|
| Target | SBS # | F1 | F2 | F3 | F4 | F5 |
| Intron 1 | 36813 | QSGNLAR (SEQ ID NO: 5) | HLGNLKT (SEQ ID NO: 94) | LKHHLTD (SEQ ID NO: 95) | DRSNLSR (SEQ ID NO: 8) | RLDNRTA (SEQ ID NO: 96) |
| Intron 1 | 36808 | QSGNLAR (SEQ ID NO: 5) | LMQNRNQ (SEQ ID NO: 97) | LKHHLTD (SEQ ID NO: 95) | DRSNLSR (SEQ ID NO: 8) | RSDHLTT (SEQ ID NO: 98) |
| Intron 1 | 36820 | QRSNLVR (SEQ ID NO: 99) | LRMNLTK (SEQ ID NO: 100) | LKHHLTD (SEQ ID NO: 95) | DRSNLSR (SEQ ID NO: 8) | RSDHLTT (SEQ ID NO: 98) |
| Intron 1 | 36819 | QRSNLVR (SEQ ID NO: 99) | LRMNLTK (SEQ ID NO: 100) | LKHHLTD (SEQ ID NO: 95) | DRSNLSR (SEQ ID NO: 8) | RSDHLTQ (SEQ ID NO: 35) |
| Intron 1 | 36806 | QSGNLAR (SEQ ID NO: 5) | LMQNRNQ (SEQ ID NO: 97) | LKHHLTD (SEQ ID NO: 95) | DRSNLSR (SEQ ID NO: 8) | RSDHLTQ (SEQ ID NO: 35) |

TABLE 6

Target sites of rhesus albumin-specific ZFNs

| Target | SBS # | Target site |
|---|---|---|
| Intron 1 | 36813 | ttAGGGACAGTTATGAAttcaatcttca_ (SEQ ID NO: 101) |
| Intron 1 | 36808 | ttAGGGACAGTTATGAAttcaatcttca_ (SEQ ID NO: 101) |
| Intron 1 | 36820 | ttAGGGACAGTTATGAAttcaatcttca_ (SEQ ID NO: 101) |
| Intron 1 | 36819 | ttAGGGACAGTTATGAAttcaatcttca_ (SEQ ID NO: 101) |
| Intron 1 | 36806 | ttAGGGACAGTTATGAAttcaatcttca_ (SEQ ID NO: 101) |

The rhesus albumin specific ZFNs were tested in pairs to determine the pair with the greatest activity. In each pair, SBS#35396 was tested with the potential partners shown in Tables 5 and 6 in the rhesus cell line RF/6A using the methods described above.

The resultant activity, as determined by percent of mismatch detected using the Cel-I assay is shown in the body of the matrix (Table 7), and demonstrate that the ZFNs pairs have activity against the rhesus albumin locus.

TABLE 7

| Activity at the rhesus macaque albumin locus | | | | | |
|---|---|---|---|---|---|
|  | 36813 | 36808 | 36820 | 36819 | 36806 |
| 35396 | 21% | 26% | 23% | 30% | 20.5% |

Two pairs were examined more extensively, comparing sequence specificity by SELEX analysis and by a titration of each pair for activity in vitro. The results demonstrate that the 35396/36806 pair was the most desirable lead pair (see FIG. 12).

Figure 3A:
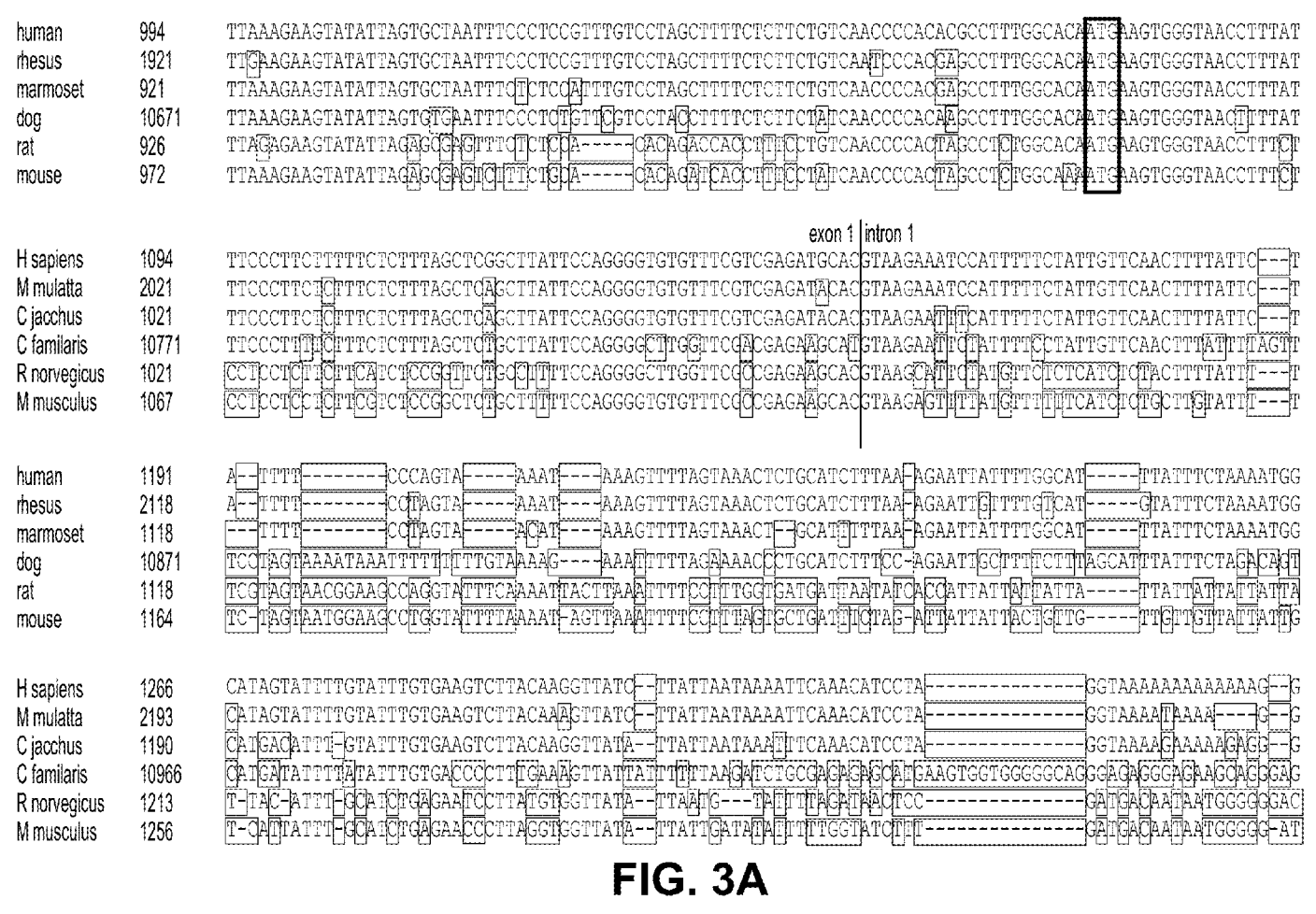
Figure 3B:
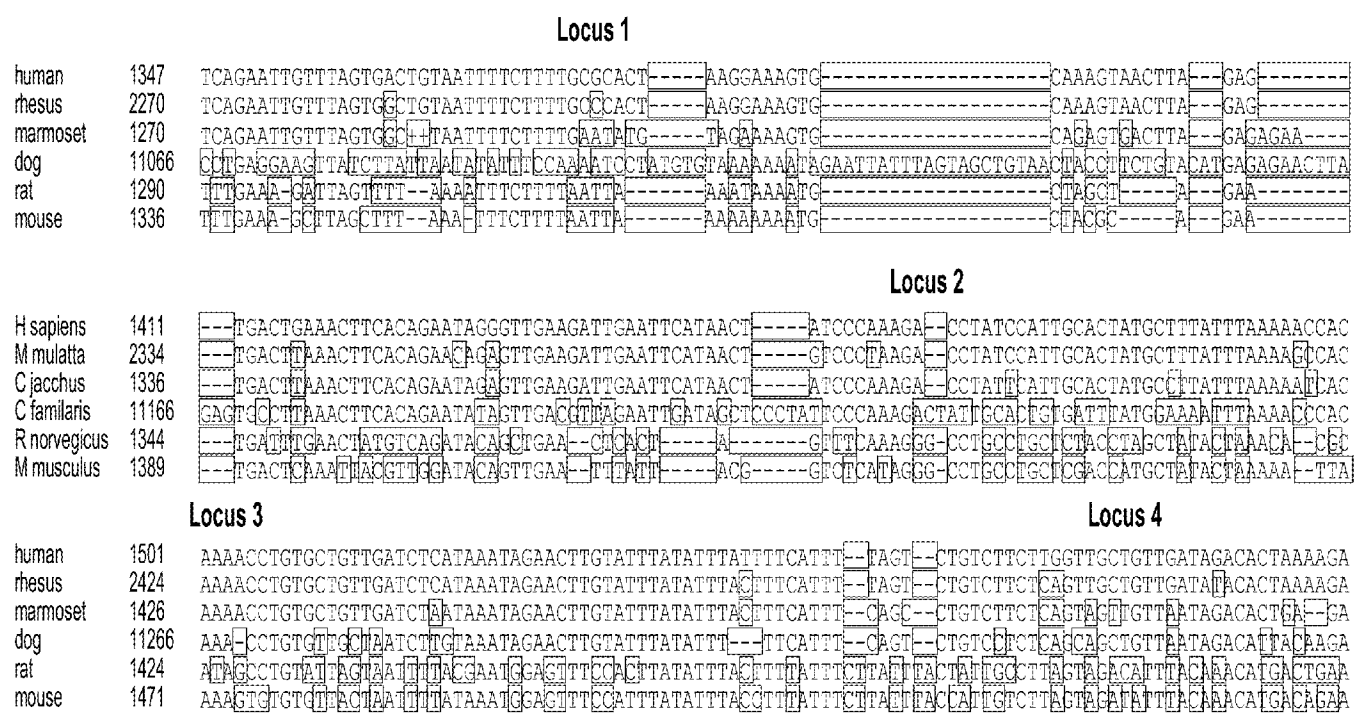
Figure 3B:
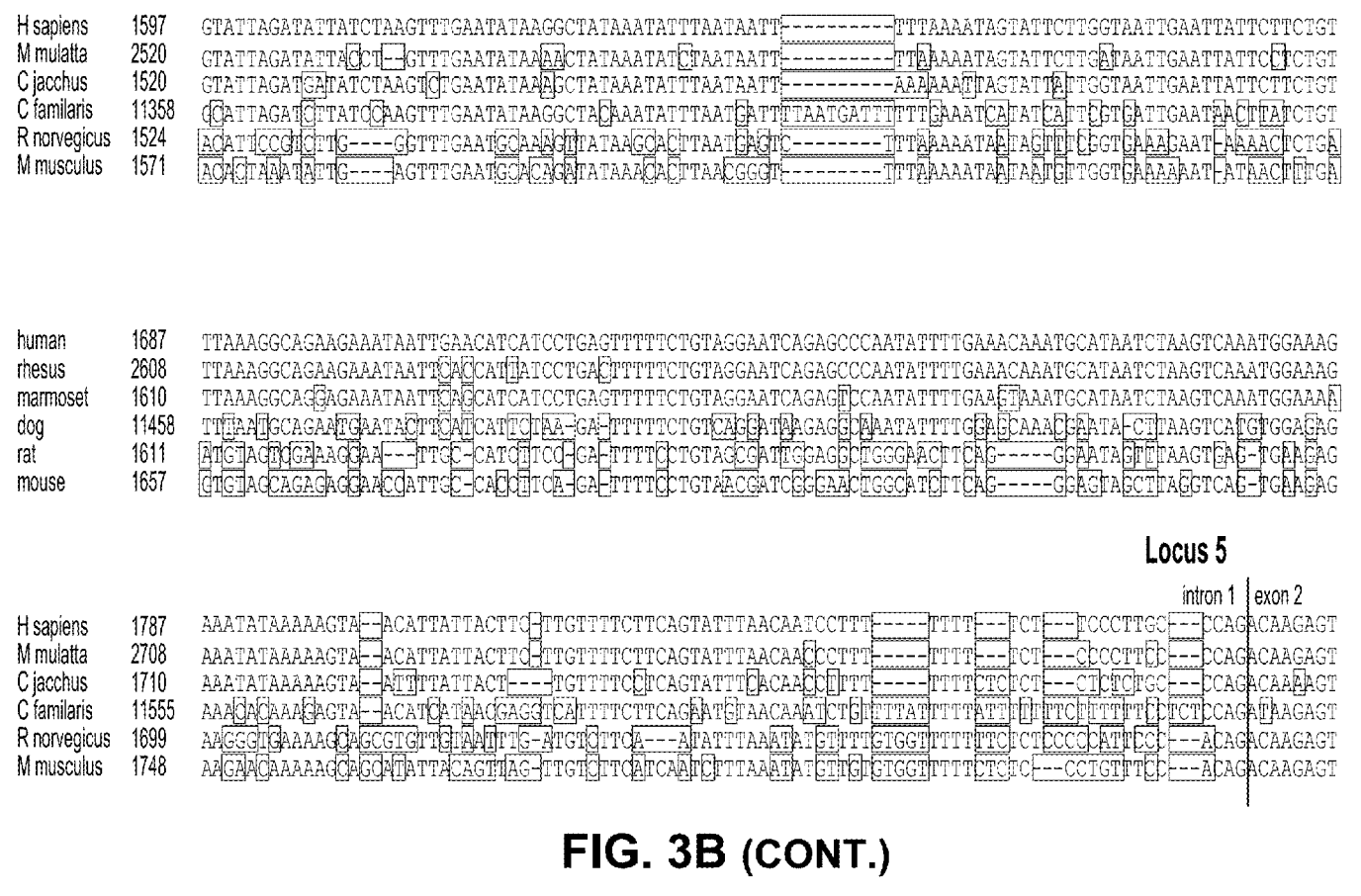

Comparison of the sequence of the human albumin locus with the sequences of other non-human primates demonstrates that similar pairs may be developed for work in other primates such as cynologous monkeys (see, FIGS. 3A and 3B).

Example 5

In Vivo Cleavage by ZFNs in Mice

To deliver the albumin-specific ZFNs to the liver in vivo, the normal site of albumin production, we generated a hepatotropic adeno-associated virus vector, serotype 8 expressing the albumin-specific ZFNs from a liver-specific enhancer and promoter (Shen et al, ibid and Miao et al, ibid). Adult C57BL/6 mice were subjected to genome editing at the albumin gene as follows: adult mice were treated by i.v. (intravenous) injection with $1 \times 10^{11}$ v.g. (viral genomes)/mouse of either ZFN pair 1 (SBS 30724 and SBS 30725), or ZFN pair 2 (SBS 30872 and SBS 30873) and sacrificed seven days later. The region of the albumin gene encompassing the target site for pair 1 was amplified by PCR for the Cel-I mismatch assay using the following 2 PCR primers:

```
                                     (SEQ ID NO: 69)
Cel1 F1:    5' CCTGCTCGACCATGCTATACT 3'

(SEQ ID NO: 70)
Cel1R1:     5' CAGGCCTTTGAAATGTTGTTC 3'
```

The region of the albumin gene encompassing the target site for pair 2 was amplified by PCR for the Cel-I assay using these PCR primers:

```
                                     (SEQ ID NO: 71)
mAlb set4F4: 5' AAGTGCAAAGCCTTTCAGGA 3'

(SEQ ID NO: 72)
mAlb set4R4: 5' GTGTCCTTGTCAGCAGCCTT 3'
```

Figure 4A:
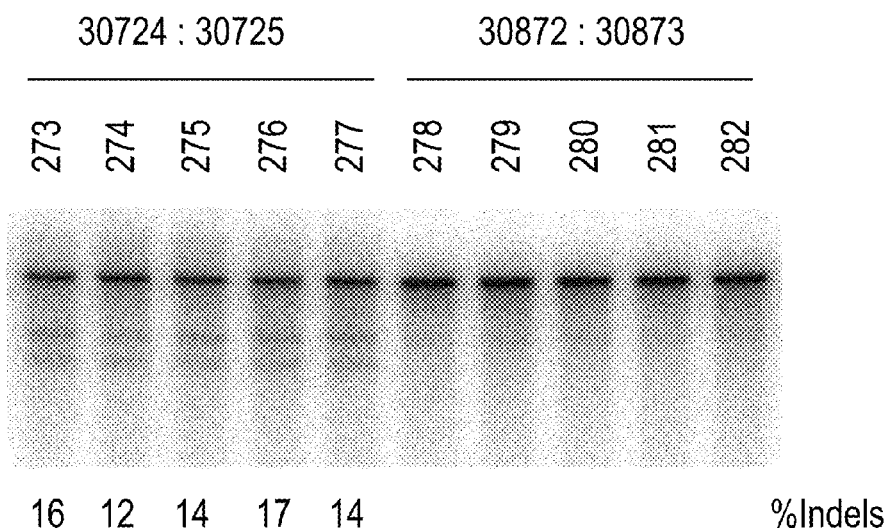
FIG. 4A is a gel that quantifies the indels present in the amplicon encompassing the pair 1 site and FIG. 4B is another gel that quantifies the indels present in the amplicon that encompasses the pair 2 site. The percent of albumin genes bearing ZFN-induced modifications in the liver biopsies is indicated at the bottom of the lanes, and demonstrates that the albumin ZFN pairs are capable of modifying up to 17% of targets when the nucleases are delivered in vivo.
Figure 4B:
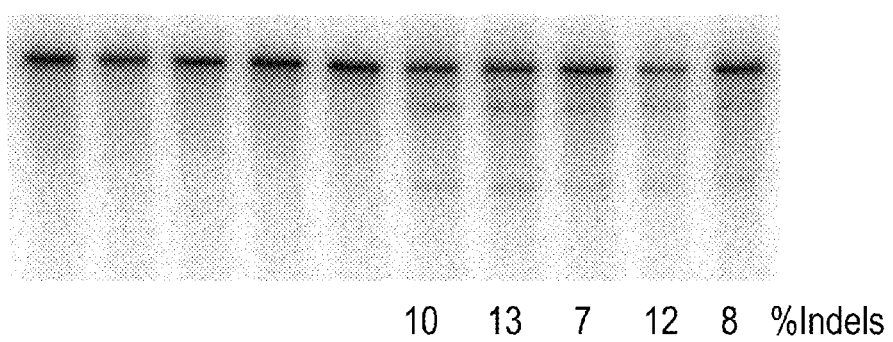

As shown in FIG. 4, the ZFNs induce indels in up to 17% of their target sites in vivo in this study.

The mouse albumin specific ZFNs SBS30724 and SBS30725 which target a sequence in intron 1 were also tested in a second study. Genes for expressing the ZFNs were introduced into an AAV2/8 vector as described previously (Li et al (2011) *Nature* 475 (7355): 217). To facilitate AAV production in the baculovirus system, a baculovirus containing a chimeric serotype 8.2 capsid gene was used. Serotype 8.2 capsid differs from serotype 8 capsid in that the phopholipase A2 domain in capsid protein VP1 of AAV8 has been replaced by the comparable domain from the AAV2 capsid creating a chimeric capsid. Production of the ZFN containing virus particles was done either by preparation using a HEK293 system or a baculovirus system using standard methods in the art (See Li et al, ibid, see e.g. US6723551). The virus particles were then administered to normal male mice (n=6) using a single dose of 200 microliter of 1.0e11 total vector genomes of either AAV2/8 or AAV2/8.2 encoding the mouse albumin-specific ZFN. 14 days post administration of rAAV vectors, mice were sacrificed, livers harvested and processed for DNA or total proteins using standard methods known in the art. Detection of AAV vector genome copies was performed by quantitative PCR. Briefly, qPCR primers were made specific to the bGHpA sequences within the AAV as follows:

```
                                    (SEQ ID NO: 102)
Oligo200 (Forward)   5'-GTTGCCAGCCATCTGTTGTTT-3'

(SEQ ID NO: 103)
Oligo201 (Reverse)   5'-GACAGTGGGAGTGGCACCTT-3'

(SEQ ID NO: 104)
Oligo202 (Probe)     5'-CTCCCCCGTGCCTTCCTTGACC-3'
```

Cleavage activity of the ZFN was measured using a Cel-I assay performed using a LC-GX apparatus (Perkin Elmer), according to manufacturer's protocol. Expression of the ZFNs in vivo was measured using a FLAG-Tag system according to standard methods.

As shown in FIG. 5 (for each mouse in the study) the ZFNs were expressed, and cleave the target in the mouse liver gene. The % indels generated in each mouse sample is provided at the bottom of each lane. The type of vector and their contents are shown above the lanes. Mismatch repair following ZFN cleavage (indicated % indels) was detected at nearly 16% in some of the mice.

The mouse specific albumin ZFNs were also tested for in vivo activity when delivered via use of a variety of AAV serotypes including AAV2/5, AAV2/6, AAV2/8 and AAV2/8.2. In these AAV vectors, all the ZFN encoding sequence is flanked by the AAV2 ITRs, contain, and then encapsulated using capsid proteins from AAV5, 6, or 8, respectively. The 8.2 designation is the same as described above. The SBS30724 and SBS30725 ZFNs were cloned into the AAV as described previously (Li et al, ibid), and the viral particles were produced either using baculovirus or a HEK293 transient transfection purification as described above. Dosing was done in normal mice in a volume of 200 μL per mouse via tail injection, at doses from 5e10 to 1e12 vg per dose. Viral genomes per diploid mouse genome were analyzed at days 14, and are analyzed at days 30 and 60. In addition, ZFN directed cleavage of the albumin locus was analyzed by Cel-I assay as described previously at day 14 and is analyzed at days 30 and 60.

Figure 6:
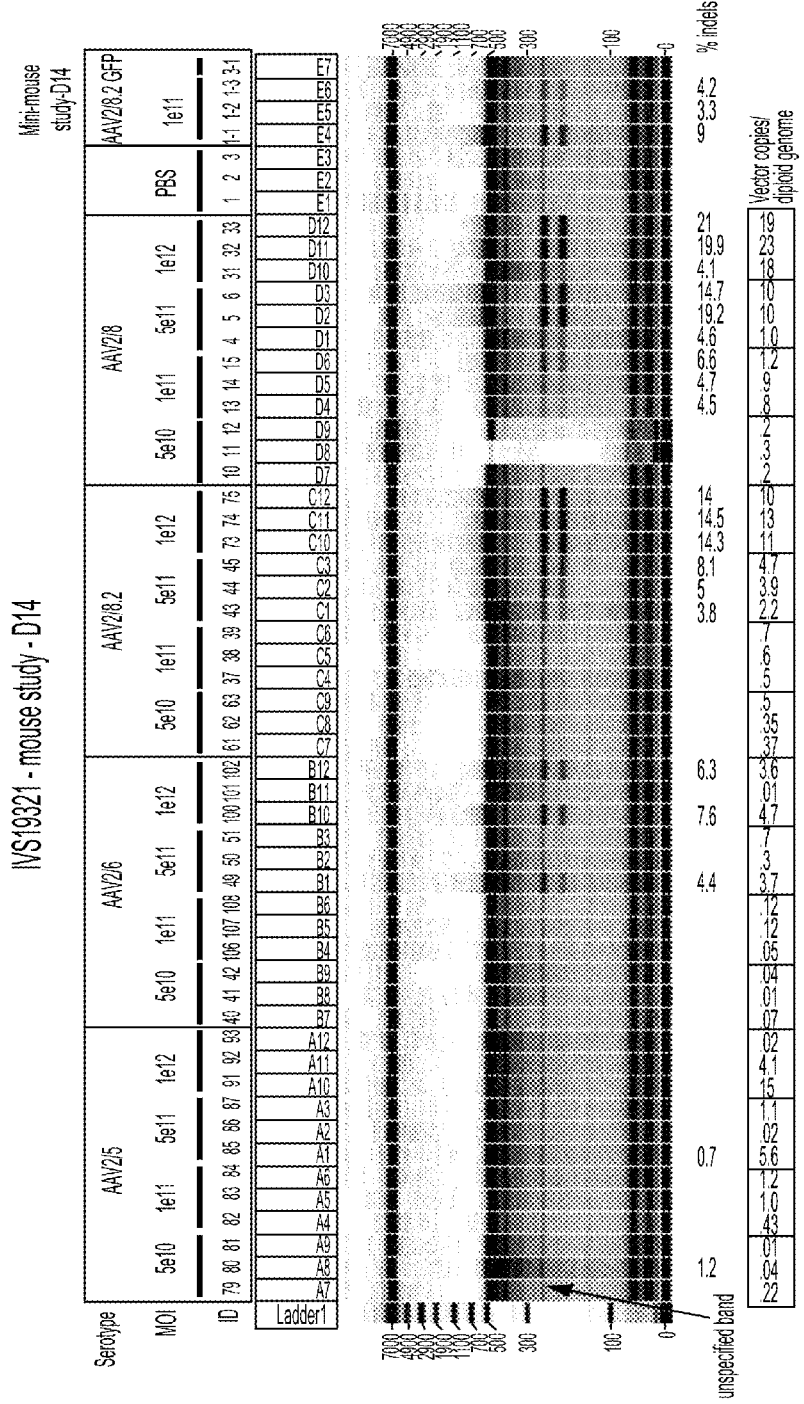
FIG. 6 shows results from a mouse study in which groups of mice were treated with the mouse albumin specific ZFN pair 30724/30725 via delivery of differing doses of different AAV serotypes, and then assessed for gene modification using the Cel-I assay. The AAV serotypes tested in this study were AAV2/5, AAV2/6, AAV2/8.2 and AAV2/8 (see text for details). The dose levels ranged from 5e10 to 1e12 viral genomes, and three mice were injected per group. Viral genomes present per diploid cell were also calculated and are indicated at the bottom of each lane. The percent indels induced by each treatment is also indicated below each lane and demonstrates that this ZFN pair is capable of cleaving the albumin locus. Control mice were injected with phosphate buffered saline. A non-specific band is also indicated in the figure.

As shown in FIG. 6, cleavage was observed at a level of up to 21% indels. Also included in Figure are the samples from the previous study as a comparison (far right, "mini-mouse" study-D14 and a background band ("unspecific band")).

Example 6

In Vivo Co-Delivery of a Donor Nucleic Acid and Albumin ZFNs

Insertion of human Factor IX: ZFNs were used to target integration of the gene for the clotting protein Factor IX (F.IX) into the albumin locus in adult wild-type mice. In these experiments, the mice were treated by I.V. injection with either $1 \times 10^{11}$ v.g./mouse albumin-specific ZFN pair 1 targeting intron 1+donor ("mAlb (intron1)"), $1 \times 10^{11}$ v.g./mouse albumin-specific ZFN pair 2 targeting intron 12+donor ("mAlb(intron12)") or a ZFN set that targets a human gene plus donor as a control ("Control"). The ZFN pair #1 was 30724/30725, targeting intron 1, and ZFN pair 2 was 30872/30873, targeting exon 12. In these experiments, the F.IX donor transgene was integrated via end capture following ZFN-induced cleavage. Alternatively, the F.IX transgene was inserted into a donor vector such that the transgene was flanked by arms with homology to the site of cleavage. In either case, the F.IX transgene was the "SA-wild-type hF9 exons 2-8" cassette (see co-owned U.S. patent application 61/392,333).

Figure 7:
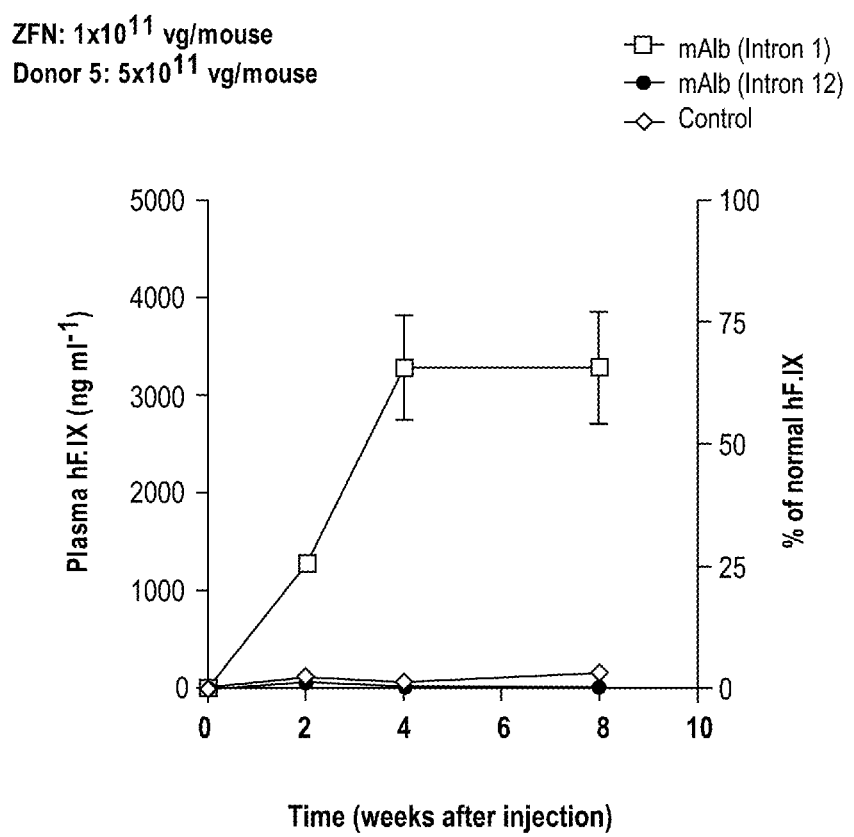
FIG. 7 is a graph depicting the expression of human factor IX (F.IX) from a transgene inserted into the mouse albumin locus in vivo. A human F.IX donor transgene was inserted into either the mouse albumin locus at intron 1 or intron 12 following cleavage with mouse albumin-specific ZFNs in wild type mice. The graph shows expression levels of F.IX over a period of 8 weeks following injection of the vectors. ZFN pairs targeting either intron 1 or intron 12 of mouse albumin were used in this experiment, as well as ZFNs targeted to a human gene as a control. The donor F.IX gene was designed to be used following insertion into intron 1, and thus is not expressed properly when inserted into intron 12. The human F.IX transgene is expressed at a robust level for at least 8 weeks following insertion into the mouse albumin intron 1 locus.
Figures 8A, 8B:
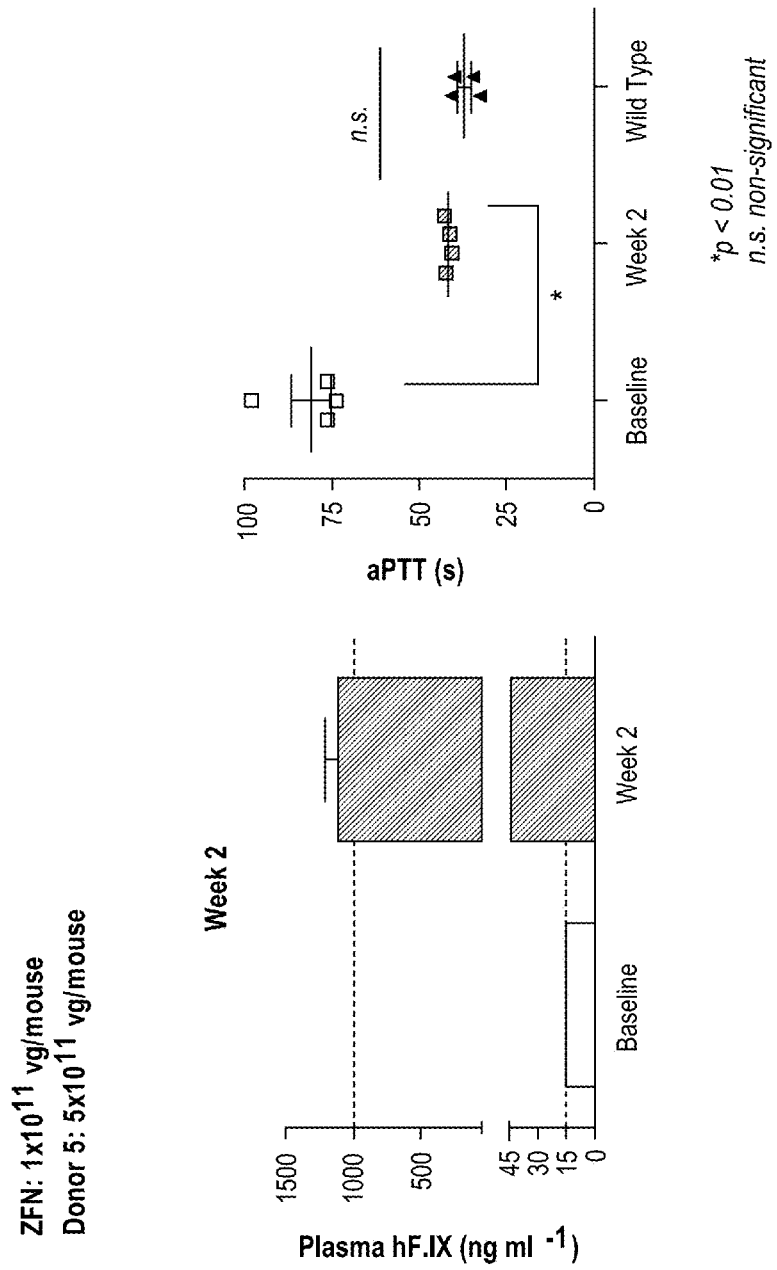
FIG. 8, panels A and B, are graphs depicting the expression and functionality of the human F.IX gene in the plasma of hemophilic mice following ZFN-induced F.IX transgene insertion. The experiment described in FIG. 7 was repeated in hemophilic mice using the albumin intron 1 specific ZFNs and the human F.IX donor. Two weeks following treatment, expression level in the serum (FIG. 8A) and clotting time (FIG. 8B) were analyzed. The expression of the human F.IX transgene in hemophilic mice was able to restore clotting time to that of normal mice.

Transduced mice were then sampled for serum human F.IX levels, which were elevated (see FIG. 7, showing stabilized expression of human F.IX for at least eight weeks following insertion into intron 1). The expressed human F.IX is also functional, as evidenced by the reduction in clotting time in hemophilic mice with a human F.IX transgene targeted into the albumin locus (see FIG. 8). Notably, within two weeks following transgene insertion, the clotting time is not significantly different than clotting time in a wild type mouse. When the intron 1 specific donor was inserted into the intron 12 locus, correct splicing to result in expression of the huF.IX cannot occur. The lack of signal in this sample verifies that the signal from the intron 1 donor being integrated into the intron 1 site is truly from correct transgene integration, and not from random integration and expression at another non-specific site.

Insertion of human alpha galactosidase (huGLa): Similar to the insertion of the human F.IX gene, the gene encoding human alpha galatosidase (deficient in patients with Fabry's disease) was inserted into the mouse albumin locus. The ZFN pair 30724/30725 was used as described above using an alpha galactosidase transgene in place of the F.IX transgene. In this experiment, 3 mice were treated with an AAV2/8 virus containing the ZFN pair at a dose of 3.0e11 viral genomes per mouse and an AAV2/8 virus containing the huGLa donor at 1.5e12 viral genomes per mouse. Control animals were given either the ZFN containing virus alone or the huGLa donor virus alone. Western blots done on liver homogenates showed an increase in alpha galactosidase-specific signal, indicating that the alpha galactosidase gene had been integrated and was being expressed (FIG. 13A). In addition, an ELISA was performed on the liver lysate using a human alpha galactosidase assay kit (Sino) according to manufacturer's protocol. The results, shown in FIG. 13B, demonstrated an increase in signal in the mice that had been treated with both the ZFNs and the huGLa donor.

Example 7

Design of Human Albumin Specific ZFNs

To design ZFNs with specificity for the human albumin gene, the DNA sequence of human albumin intron 1 was analyzed using previously described methods to identify target sequences with the best potential for ZFN binding. Regions throughout the intron (loci 1-5) were chosen and several ZFNs were designed to target these regions region (for example, see FIG. 9 which shows the binding sites of ZFNs from loci 1-3). In this analysis, five loci were identified to target in the albumin intron1 (see FIG. 3B). The target and helices are shown in Tables 8 and 9.

TABLE 8

Human albumin-specific zinc finger nucleases helix designs

| Target SBS # | Design | | | | | |
|---|---|---|---|---|---|---|
| | F1 | F2 | F3 | F4 | F5 | F6 |
| Intron 1 35393 | QSSDLSR (SEQ ID NO: 46) | LRHNLRA (SEQ ID NO: 105) | DQSNLRA (SEQ ID NO: 106) | RPYTLRL (SEQ ID NO: 107) | QSSDLSR (SEQ ID NO: 46) | HRSNLNK (SEQ ID NO: 108) |
| Intron 1 35394 | QSSDLSR (SEQ ID NO: 46) | HRSNLNK (SEQ ID NO: 108) | DQSNLRA (SEQ ID NO: 106) | RPYTLRL (SEQ ID NO: 107) | QSSDLSR (SEQ ID NO: 46) | HRSNLNK (SEQ ID NO: 108) |
| Intron 1 35396 | QSSDLSR (SEQ ID NO: 46) | LKWNLRT (SEQ ID NO: 109) | DQSNLRA (SEQ ID NO: 106) | RPYTLRL (SEQ ID NO: 107) | QSSDLSR (SEQ ID NO: 46) | HRSNLNK (SEQ ID NO: 108) |
| Intron 1 35398 | QSSDLSR (SEQ ID NO: 46) | LRHNLRA (SEQ ID NO: 105) | DQSNLRA (SEQ ID NO: 106) | RPYTLRL (SEQ ID NO: 107) | QSSDLSR (SEQ ID NO: 46) | HRSNLNK (SEQ ID NO: 108) |
| Intron 1 35399 | QSSDLSR (SEQ ID NO: 46) | HRSNLNK (SEQ ID NO: 108) | DQSNLRA (SEQ ID NO: 106) | RPYTLRL (SEQ ID NO: 107) | QSSDLSR (SEQ ID NO: 46) | HRSNLNK (SEQ ID NO: 108) |
| Intron 1 35405 | QSSDLSR (SEQ ID NO: 46) | WKWNLRA (SEQ ID NO: 110) | DQSNLRA (SEQ ID NO: 106) | RPYTLRL (SEQ ID NO: 107) | QSSDLSR (SEQ ID NO: 46) | HRSNLNK (SEQ ID NO: 108) |
| Intron 1 35361 | QSGNLAR (SEQ ID NO: 5) | LMQNRNQ (SEQ ID NO: 9) | LKQHLNE (SEQ ID NO: 111) | TSGNLTR (SEQ ID NO: 11) | RRYYLRL (SEQ ID NO: 112) | N/A |
| Intron 1 35364 | QSGNLAR (SEQ ID NO: 5) | HLGNLKT (SEQ ID NO: 94) | LKQHLNE (SEQ ID NO: 111) | TSGNLTR (SEQ ID NO: 11) | RRDWRRD (SEQ ID NO: 113) | N/A |
| Intron 1 35370 | QSGNLAR (SEQ ID NO: 5) | LMQNRNQ (SEQ ID NO: 9) | LKQHLNE (SEQ ID NO: 111) | TSGNLTR (SEQ ID NO: 11) | RRDWRRD (SEQ ID NO: 113) | N/A |

TABLE 8-continued

Human albumin-specific zinc finger nucleases helix designs

| Target SBS # | F1 | F2 | F3 | F4 | F5 | F6 |
|---|---|---|---|---|---|---|
| Intron 1 35379 | QRSNLVR (SEQ ID NO: 99) | TSSNRKT (SEQ ID NO: 53) | LKHHLTD (SEQ ID NO: 95) | TSGNLTR (SEQ ID NO: 11) | RRDWRRD (SEQ ID NO: 113) | N/A |
| Intron 1 35458 | DKSYLRP (SEQ ID NO: 114) | TSGNLTR (SEQ ID NO: 11) | HRSARKR (SEQ ID NO: 115) | QSSDLSR (SEQ ID NO: 46) | WRSSLKT (SEQ ID NO: 163) | N/A |
| Intron 1 35480 | TSGNLTR (SEQ ID NO: 11) | HRSARKR (SEQ ID NO: 115) | QSGDLTR (SEQ ID NO: 40) | NRHHLKS (SEQ ID NO: 116) | N/A | N/A |
| Intron 1 35426 | QSGDLTR (SEQ ID NO: 40) | QSGNLHV (SEQ ID NO: 117) | QSAHRKN (SEQ ID NO: 118) | STAALSY (SEQ ID NO: 119) | TSGSLSR (SEQ ID NO: 120) | RSDALAR (SEQ ID NO: 41) |
| Intron 1 35428 | QSGDLTR (SEQ ID NO: 40) | QRSNLNI (SEQ ID NO: 121) | QSAHRKN (SEQ ID NO: 118) | STAALSY (SEQ ID NO: 119) | DRSALSR (SEQ ID NO: 52) | RSDALAR (SEQ ID NO: 41) |
| Intron 1 34931 | QRTHLTQ (SEQ ID NO: 122) | DRSNLTR (SEQ ID NO: 123) | QSGNLAR (SEQ ID NO: 5) | QKVNRAG (SEQ ID NO: 124) | N/A | N/A |
| Intron 1 33940 | RSDNLSV (SEQ ID NO: 26) | QNANRIT (SEQ ID NO: 125) | DQSNLRA (SEQ ID NO: 106) | QSAHRIT (SEQ ID NO: 126) | TSGNLTR (SEQ ID NO: 11) | HRSARKR (SEQ ID NO: 115) |

TABLE 9

Target sites of Human albumin-specific ZFNs

| Target | SBS # | Target site |
|---|---|---|
| Intron 1 (locus 2) | 35393 | ccTATCCATTGCACTATGCTttatttaa (SEQ ID NO: 127) |
| Intron 1 (locus 2) | 35394 | ccTATCCATTGCACTATGCTttatttaa (SEQ ID NO: 127) |
| Intron 1 (locus 2) | 35396 | ccTATCCATTGCACTATGCTttatttaa (SEQ ID NO: 127) |
| Intron 1 (locus 2) | 35398 | ccTATCCATTGCACTATGCTttatttaa (SEQ ID NO: 127) |
| Intron 1 (locus 2) | 35399 | ccTATCCATTGCACTATGCTttatttaa (SEQ ID NO: 127) |
| Intron 1 (locus 2) | 35405 | ccTATCCATTGCACTATGCTttatttaa (SEQ ID NO: 127) |
| Intron 1 (locus 2) | 35361 | ttTGGGATAGTTATGAAttcaatcttca (SEQ ID NO: 128) |
| Intron 1 (locus 2) | 35364 | ttTGGGATAGTTATGAAttcaatcttca (SEQ ID NO: 128) |
| Intron 1 (locus 2) | 35370 | ttTGGGATAGTTATGAAttcaatcttca (SEQ ID NO: 128) |
| Intron 1 (locus 2) | 35379 | ttTGGGATAGTTATGAAttcaatcttca (SEQ ID NO: 128) |
| Intron 1 (locus 3) | 35458 | ccTGTGCTGTTGATCTCataaatagaac (SEQ ID NO: 129) |
| Intron 1 (locus 3) | 35480 | ccTGTGCTGTTGATctcataaatagaac (SEQ ID NO: 129) |
| Intron 1 (locus 3) | 35426 | ttGTGGTTTTTAAAtAAAGCAtagtgca (SEQ ID NO: 130) |
| Intron 1 (locus 3) | 35428 | ttGTGGTTTTTAAAtAAAGCAtagtgca (SEQ ID NO: 130) |
| Intron 1 (locus 4) | 34931 | acCAAGAAGACAGActaaaatgaaaata (SEQ ID NO: 131) |
| Intron 1 (locus 4) | 33940 | ctGTTGATAGACACTAAAAGagtattag (SEQ ID NO: 132) |

These nucleases were tested in pairs to determine the pair with the highest activity. The resultant matrices of tested pairs are shown in Tables 10 and 11, below where the ZFN used for the right side of the dimer is shown across the top of each matrix, and the ZFN used for the left side of the dimer is listed on the left side of each matrix. The resultant activity, as determined by percent of mismatch detected using the Cel-I assay is shown in the body of both matrices:

TABLE 10

Activity of Human albumin-specific ZFNs (% mutated targets)

|  | 35393 | 35394 | 35396 | 35398 | 35399 | 35405 | ave. |
|---|---|---|---|---|---|---|---|
| 35361 | 18 | 19 | 25 | 22 | 23 | 21 | 21 |
| 35364 | n.d. | 24 | 23 | 19 | 21 | 21 | 22 |
| 35370 | 21 | 19 | 22 | n.d. | 22 | 23 | 21 |
| 35379 | 21 | 21 | n.d. | 19 | 19 | 21 | 20 |

TABLE 11

Activity of Human albumin-specific ZFNs (% mutated targets))

|  | 35458 | 35480 | ave. |
|---|---|---|---|
| 35426 | 4.5 | 7 | 3 |
| 35428 | 4.9 | 6 | 3.6 |

(note:
'n.d.' means the assay on this pair was not done)

Thus, highly active nucleases have been developed that recognize target sequences in intron 1 of human albumin.

Example 8

Design of Albumin Specific TALENs

TALENs were designed to target sequences within human albumin intron 1. Base recognition was achieved using the canonical RVD-base correspondences (the "TALE code": NI for A, HD for C, NN for G (NK in half repeat), NG for T). TALENs were constructed as previously described (see co-owned U.S. Patent Publication No. 20110301073). Targets for a subset of TALENs were conserved in cynomolgus monkey and rhesus macaque albumin genes (see FIG. 10). The TALENs were constructed in the "+17" and "+63" TALEN backbones as described in US20110301073. The targets and numeric identifiers for the TALENs tested are shown below in Table 12.

TABLE 12

Albumin specific TALENs

| SBS # | site | # of RVDs | SEQ ID NO: |
|---|---|---|---|
| 102249 | gtTGAAGATTGAATTCAta | 15 | 133 |
| 102250 | gtTGAAGATTGAATTCATAac | 17 | 164 |
| 102251 | gtGCAATGGATAGGTCTtt | 15 | 134 |
| 102252 | atAGTGCAATGGATAGGtc | 15 | 135 |
| 102253 | atTGAATTCATAACTATcc | 15 | 136 |
| 102254 | atTGAATTCATAACTATCCca | 17 | 137 |
| 102255 | atAAAGCATAGTGCAATGGat | 17 | 138 |
| 102256 | atAAAGCATAGTGCAATgg | 15 | 139 |
| 102257 | ctATGCTTTATTTAAAAac | 15 | 140 |
| 102258 | ctATGCTTTATTTAAAAACca | 17 | 141 |
| 102259 | atTTATGAGATCAACAGCAca | 17 | 142 |
| 102260 | ctATTTATGAGATCAACAGca | 17 | 158 |
| 102261 | ttCATTTTAGTCTGTCTTCtt | 17 | 143 |
| 102262 | atTTTAGTCTGTCTTCTtg | 15 | 144 |
| 102263 | ctAATACTCTTTTAGTGTct | 16 | 145 |
| 102264 | atCTAATACTCTTTTAGTGtc | 17 | 146 |
| 102265 | atAATTGAACATCATCCtg | 15 | 147 |
| 102266 | atAATTGAACATCATCCTGag | 17 | 148 |
| 102267 | atATTGGGCTCTGATTCCTac | 17 | 149 |
| 102268 | atATTGGGCTCTGATTCct | 15 | 150 |
| 102269 | ttTTTCTGTAGGAATCAga | 15 | 159 |
| 102270 | ttTTTCTGTAGGAATCAGag | 16 | 151 |
| 102271 | ttATGCATTTGTTTCAAaa | 15 | 152 |
| 102272 | atTATGCATTTGTTTCAaa | 15 | 153 |

Figure 11A:
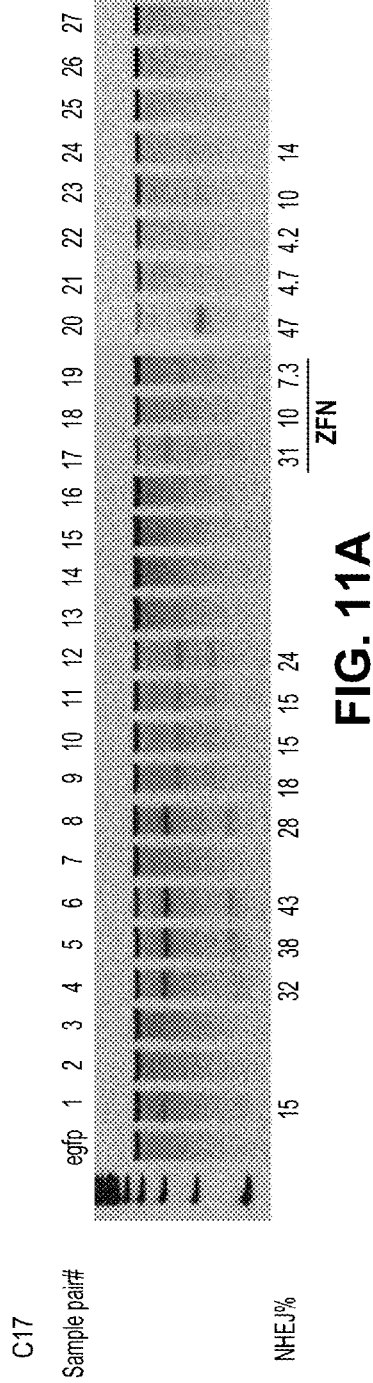
FIG. 11, panels A to C, show the results of a Cel-I assay carried out on genomic DNA isolated from HepG2 cells treated with TALENs or ZFNs targeted to human albumin (FIGS. 11A and B) and NHEJ activity of TALENs with different gap spacings (FIG. 11C). The nucleases were introduced into HepG2 cells via transient plasmid transfection and quantified 3 days later for target modification via the Cel-I assay. Two variations of the TALE DNA binding domain were used, which differed in the location of their C-terminal truncation points, the +17 version and the +63 version (see text). Pairs used are described in Table 10. In addition, three ZFN pairs were also tested and the % indels detected by the Cel 1 assay is indicated at the bottom of the lanes.
FIG. 11C is a graph depicting NHEJ activity in terms of the gap spacing (bp) between TALEN binding sites.
Figure 11B:
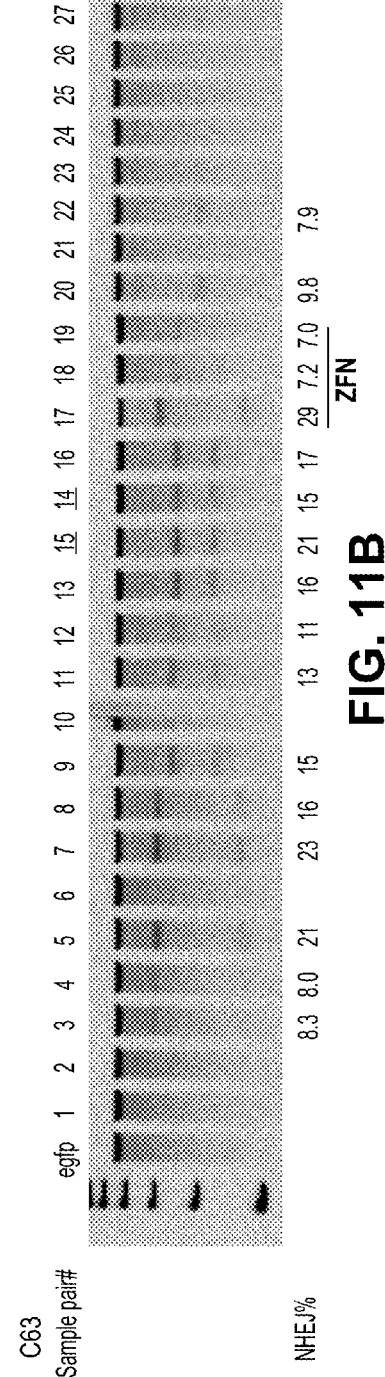
Figure 11C:
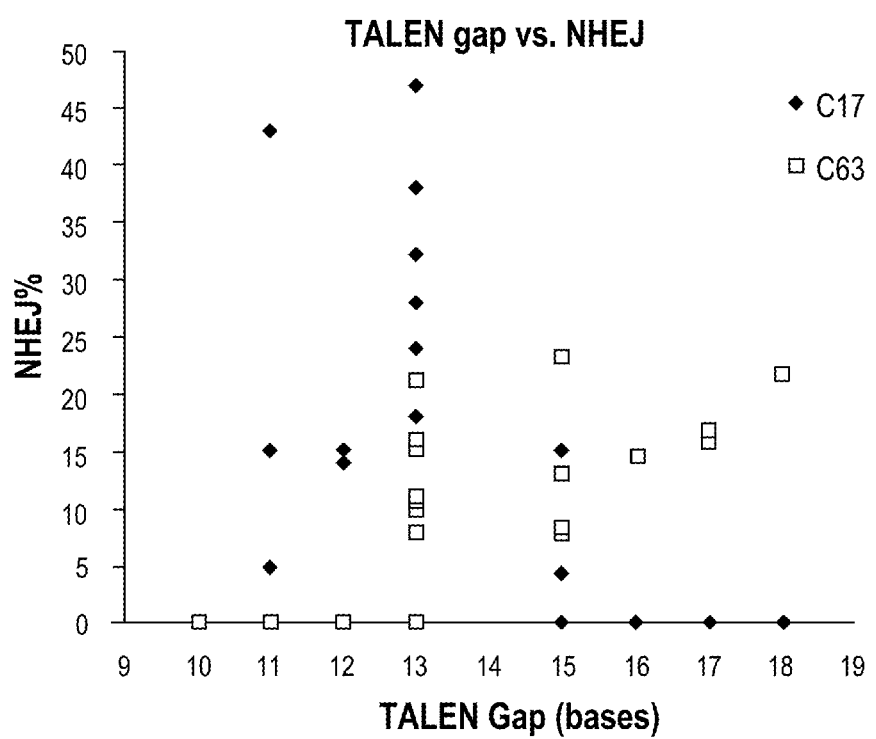
Figures 12A, 12B:
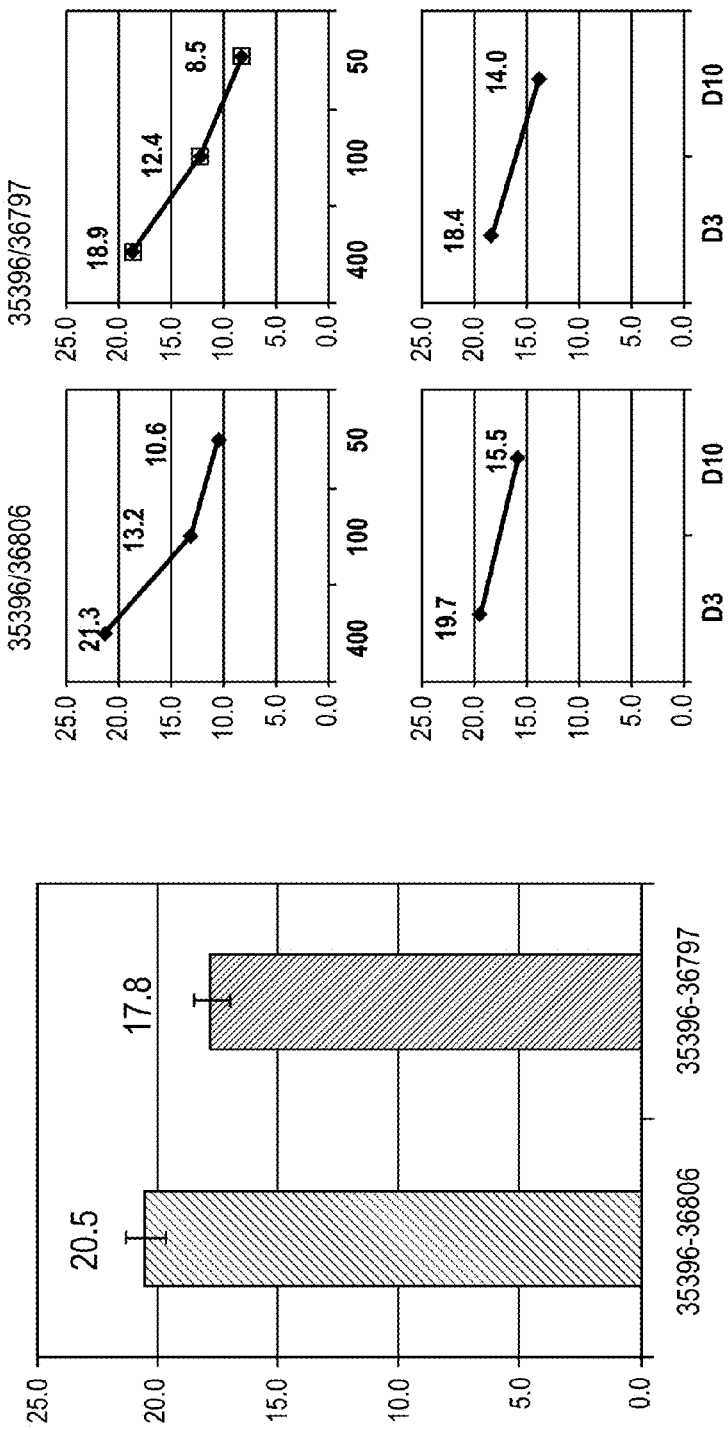
FIG. 12A shows the percent of NHEJ activity for the 35396/36806 pair in comparison with the 35396/36797 pair, tested in RF/6A cells in 3 independent experiments all done using a ZFN concentration of 400 ng.
FIG. 12B depicts a dose titration for the two pairs, from 50 ng of each ZFN to 400 ng where the samples were analyzed at day 3 following transduction. The lower half of FIG. 12B depicts another experiment comparing the two pairs at day 3 or day 10 using 400 ng of ZFN.
Figure 12C:
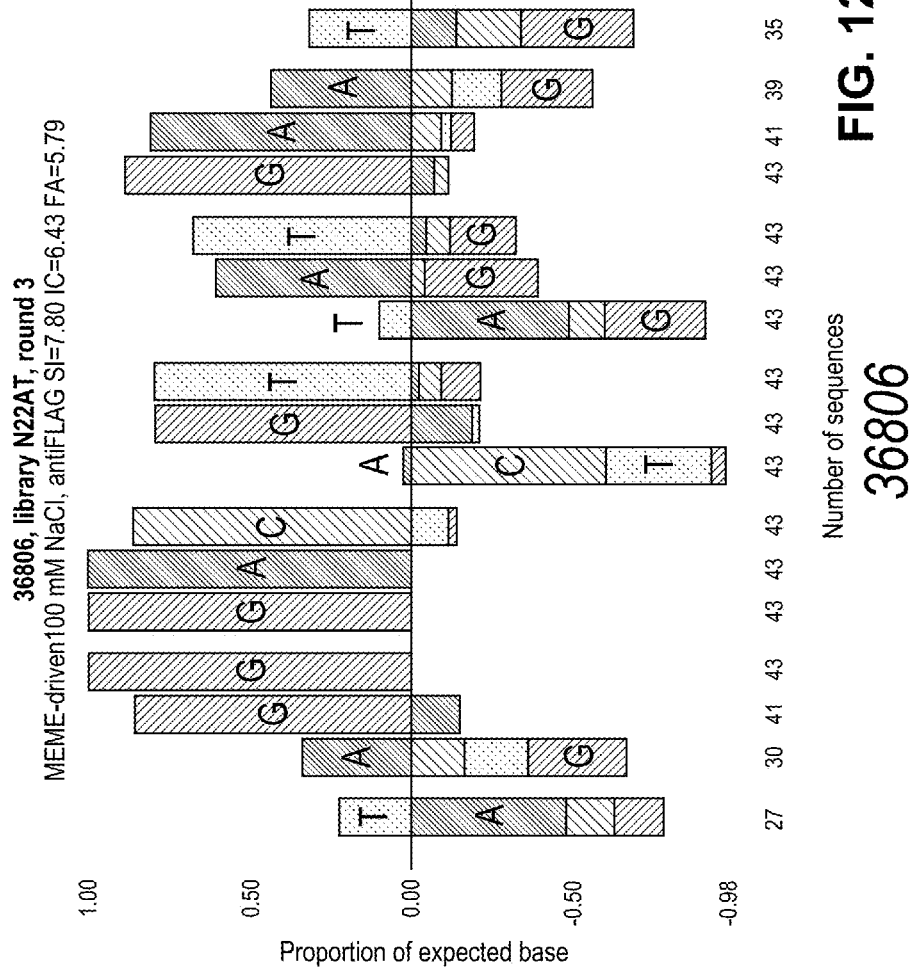
FIG. 12C depicts the results of the SELEX analysis (done at 100 mM salt concentration) of the three ZFNs that were being compared where the size of the bar above the middle line shows the results for that position that were expected (i.e., a single bar with a value of 1.0 above the line would mean that every base at that position analyzed in the SELEX analysis was the expected base), while bars below the line indicate the presence of non-expected bases. Bars that are divided indicate the relative contributions of other bases.
Figure 12C:
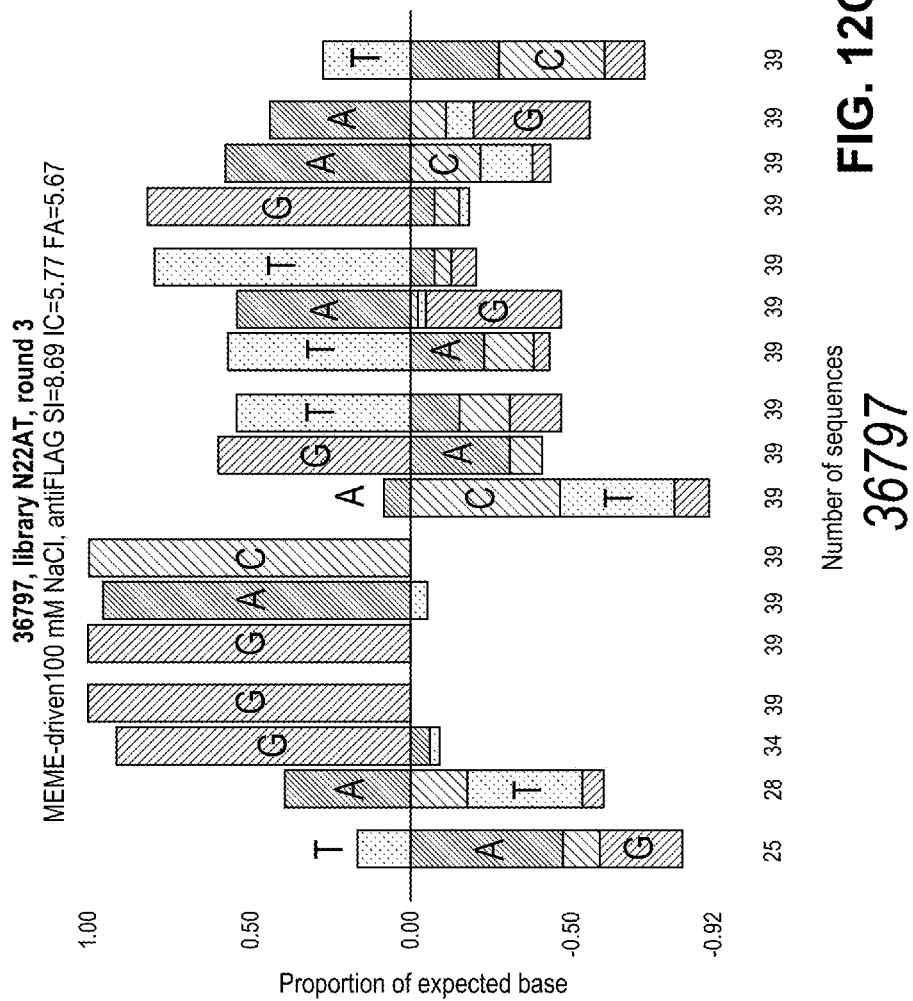
Figure 12C:
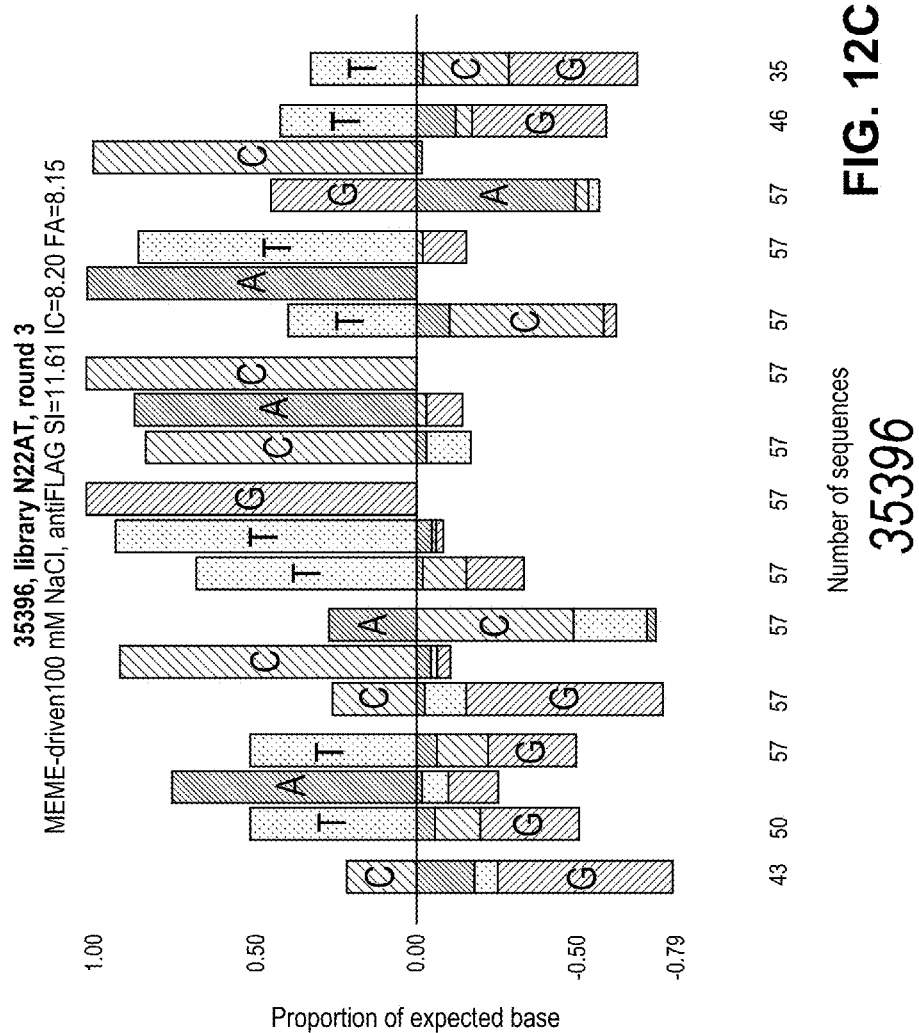

The TALENs were then tested in pairs in HepG2 cells for the ability to induce modifications at their endogenous chromosomal targets, and the results showed that many proteins bearing the +17 truncation point were active. Similarly, many TALENs bearing the +63 truncation point were also active (see Table 13 and FIG. 11). Note that the pair numbers shown in Table 13 correspond with the pair numbers shown above the lanes in FIG. 11. Side by side comparisons with three sets of non-optimized albumin ZFNs showed that the TALENs and ZFNs have activities that are in the same approximate range.

TABLE 13

TALEN-induced target modification in HepG2-C3a cells

| Sample pair | TALEN C17 | % modification, C17 | TALEN C63 | % modification, C63 | Gap |
|---|---|---|---|---|---|
| 1 | 102251:102249 | 15 | 102251:102249 | 0 | 12 |
| 2 | 102251:102250 | 0 | 102251:102250 | 0 | 10 |
| 3 | 102252:102249 | 0 | 102252:102249 | 8.3 | 15 |
| 4 | 102252:102250 | 32 | 102252:102250 | 8.0 | 13 |
| 5 | 102255:102253 | 38 | 102255:102253 | 21 | 13 |
| 6 | 102255:102254 | 43 | 102255:102254 | 0 | 11 |
| 7 | 102256:102253 | 0 | 102256:102253 | 23 | 15 |
| 8 | 102256:102254 | 28 | 102256:102254 | 16 | 13 |
| 9 | 102259:102257 | 18 | 102259:102257 | 15 | 13 |
| 10 | 102259:102258 | 15 | 102259:102258 | 0 | 11 |
| 11 | 102260:102257 | 15 | 102260:102257 | 13 | 15 |
| 12 | 102260:102258 | 24 | 102260:102258 | 11 | 13 |
| 13 | 102263:102261 | 0 | 102263:102261 | 16 | 17 |
| 14 | 102263:102262 | 0 | 102263:102262 | 15 | 16 |
| 15 | 102264:102261 | 0 | 102264:102261 | 22 | 18 |
| 16 | 102264:102262 | 0 | 102264:102262 | 17 | 17 |
| 20 | 102267:102265 | 47 | 102267:102265 | 9.8 | 13 |
| 21 | 102267:102266 | 4.7 | 102267:102266 | 0 | 11 |
| 22 | 102268:102265 | 4.2 | 102268:102265 | 7.9 | 15 |
| 23 | 102268:102266 | 10 | 102268:102266 | 0 | 13 |
| 24 | 102271:102269 | 14 | 102271:102269 | 0 | 12 |
| 25 | 102271:102270 | 0 | 102271:102270 | 0 | 11 |
| 26 | 102272:102269 | 0 | 102272:102269 | 0 | 13 |
| 27 | 102272:102270 | 0 | 102272:102270 | 0 | 12 |
| ZFNs | | | | | |
| 17 | 35361:35396 | 31 | 35361:35396 | 29 | 6 |
| 18 | 35426:35458 | 10 | 35426:35458 | 7 | 6 |
| 19 | 34931:33940 | 7.3 | 34931:33940 | 7 | 6 |

Figure 10:
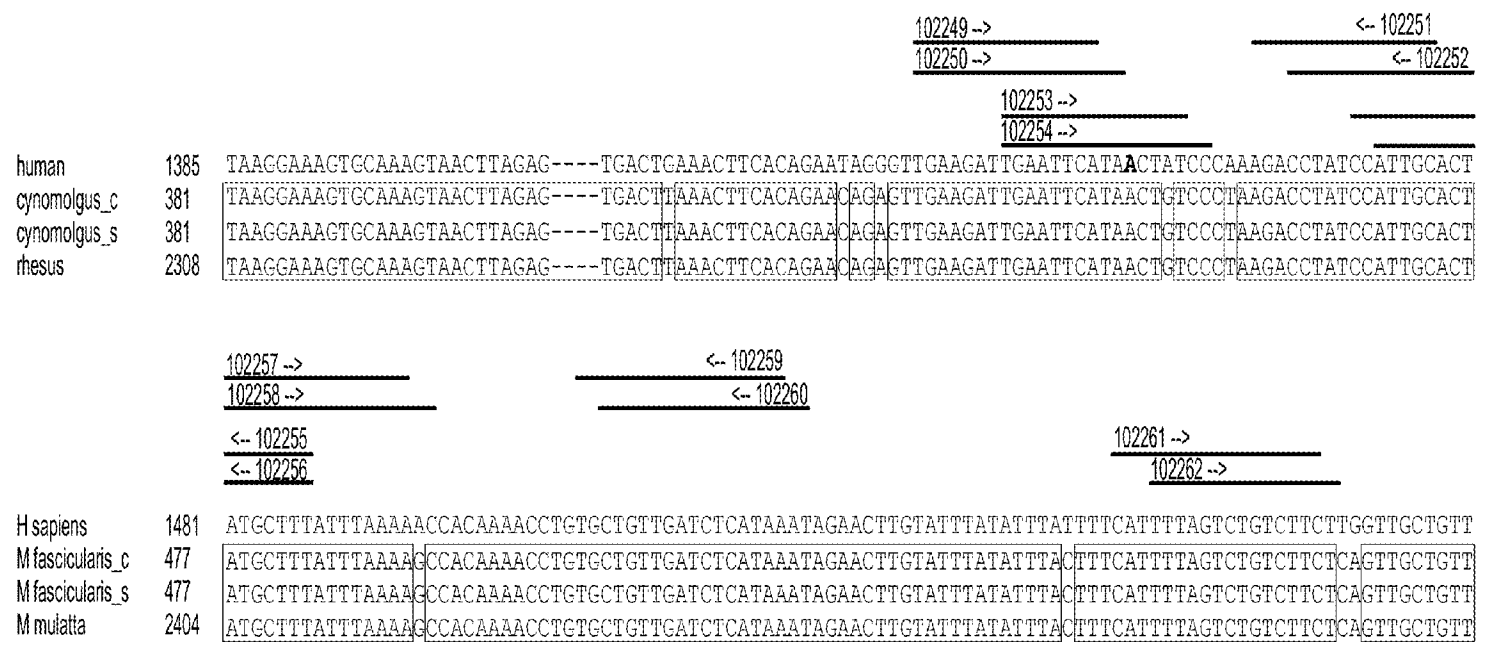
Figure 10:
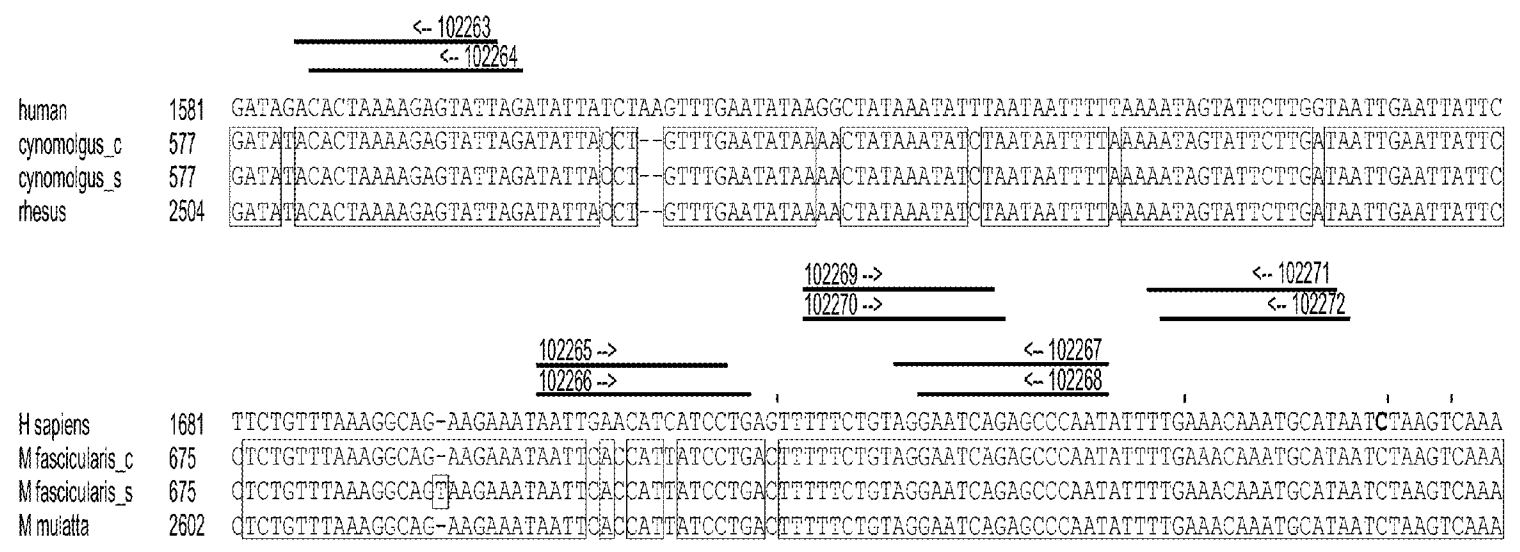

As noted previously (see co-owned U.S. Patent Publication No. 20110301073), the C17 TALENs have greater activity when the gap size between the two TALEN target sites is approximately 11-15 bp, while the C63 TALENs sustain activity at gap sizes up to 18 bp (see FIG. 10, 11C and Table 13).

All patents, patent applications and publications mentioned herein are hereby incorporated by reference in their entirety.

Although disclosure has been provided in some detail by way of illustration and example for the purposes of clarity of understanding, it will be apparent to those skilled in the art that various changes and modifications can be practiced without departing from the spirit or scope of the disclosure. Accordingly, the foregoing descriptions and examples should not be construed as limiting.

What is claimed is:

1. A non-naturally occurring fusion protein comprising a zinc finger DNA-binding protein that binds to an endogenous albumin gene and a cleavage domain, wherein the non-naturally occurring fusion protein cleaves the endogenous albumin gene and further wherein the zinc finger protein DNA-binding domain comprises 4, 5 or 6 zinc finger domains, each zinc finger domain comprising a recognition helix region, wherein the zinc finger proteins comprise the recognition helix regions in the order shown in a single row of Table 1, Table 3, Table 5 or Table 8.

2. An isolated cell comprising one or more fusion proteins according to claim 1.

3. The cell of claim 2, wherein the cell is a stem cell.

4. The cell of claim 3, wherein the stem cell is selected from the group consisting of an embryonic stem cell (ESC), an induced pluripotent stem cell (iPSC), a hepatic stem cell and a liver stem cell.

5. A kit comprising one or more non-naturally occurring fusion proteins according to claim 1.

* * * * *

```
                              SEQUENCE LISTING

<160> NUMBER OF SEQ ID NOS: 165

<210> SEQ ID NO 1
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Thr Ser Gly Ser Leu Thr Arg
1               5

<210> SEQ ID NO 2
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Arg Ser Asp Ala Leu Ser Thr
1               5

<210> SEQ ID NO 3
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Gln Ser Ala Thr Arg Thr Lys
1               5

<210> SEQ ID NO 4
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Thr Ser Gly His Leu Ser Arg
1               5

<210> SEQ ID NO 5
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Gln Ser Gly Asn Leu Ala Arg
1               5
```

<210> SEQ ID NO 6
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Arg Ser Asp His Leu Ser Ala
1               5

<210> SEQ ID NO 7
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Thr Lys Ser Asn Arg Thr Lys
1               5

<210> SEQ ID NO 8
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Asp Arg Ser Asn Leu Ser Arg
1               5

<210> SEQ ID NO 9
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Trp Arg Ser Ser Leu Arg Ala
1               5

<210> SEQ ID NO 10
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Asp Ser Ser Asp Arg Lys Lys
1               5

<210> SEQ ID NO 11
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 11

Thr Ser Gly Asn Leu Thr Arg
1               5

<210> SEQ ID NO 12
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Asp Arg Ser Thr Arg Arg Gln
1               5

<210> SEQ ID NO 13
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Glu Arg Gly Thr Leu Ala Arg
1               5

<210> SEQ ID NO 14
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Thr Ser Ala Asn Leu Ser Arg
1               5

<210> SEQ ID NO 15
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Asp Arg Ser Ala Leu Ala Arg
1               5

<210> SEQ ID NO 16
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Arg Ser Asp His Leu Ser Glu
1               5

<210> SEQ ID NO 17
<211> LENGTH: 7
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 17

His Arg Ser Asp Arg Thr Arg
1               5

<210> SEQ ID NO 18
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Gln Ser Gly Ala Leu Ala Arg
1               5

<210> SEQ ID NO 19
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Gln Ser Gly His Leu Ser Arg
1               5

<210> SEQ ID NO 20
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Arg Ser Asp Asn Leu Ser Thr
1               5

<210> SEQ ID NO 21
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Asp Gly Arg Asn Leu Arg His
1               5

<210> SEQ ID NO 22
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Arg Ser Asp Asn Leu Ala Arg
1               5
```

<210> SEQ ID NO 23
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Gln Ser Asn Ala Leu Asn Arg
1               5

<210> SEQ ID NO 24
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Leu Lys Gln Val Leu Val Arg
1               5

<210> SEQ ID NO 25
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Gln Ser Thr Pro Leu Phe Ala
1               5

<210> SEQ ID NO 26
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Arg Ser Asp Asn Leu Ser Val
1               5

<210> SEQ ID NO 27
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

His Ser Asn Ala Arg Lys Thr
1               5

<210> SEQ ID NO 28
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 28

Arg Ser Asp Ser Leu Ser Ala
1               5

<210> SEQ ID NO 29
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Arg Ser Asp Ser Leu Ser Val
1               5

<210> SEQ ID NO 30
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Arg Ser Asp Asn Leu Ser Glu
1               5

<210> SEQ ID NO 31
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Glu Arg Ala Asn Arg Asn Ser
1               5

<210> SEQ ID NO 32
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Gln Ser Ala Asn Arg Thr Lys
1               5

<210> SEQ ID NO 33
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Arg Ser Asp Ala Leu Thr Gln
1               5

<210> SEQ ID NO 34
<211> LENGTH: 7
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Gln Ser Gly His Leu Ala Arg
1               5

<210> SEQ ID NO 35
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Arg Ser Asp His Leu Thr Gln
1               5

<210> SEQ ID NO 36
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Arg Ser Asp His Leu Ser Gln
1               5

<210> SEQ ID NO 37
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Trp Arg Ser Ser Leu Val Ala
1               5

<210> SEQ ID NO 38
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Arg Ser Asp Val Leu Ser Glu
1               5

<210> SEQ ID NO 39
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Arg Asn Gln His Arg Lys Thr
```

```
1               5

<210> SEQ ID NO 40
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Gln Ser Gly Asp Leu Thr Arg
1               5

<210> SEQ ID NO 41
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Arg Ser Asp Ala Leu Ala Arg
1               5

<210> SEQ ID NO 42
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Arg Arg Asp Pro Leu Ile Asn
1               5

<210> SEQ ID NO 43
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Ile Arg Ser Thr Leu Arg Asp
1               5

<210> SEQ ID NO 44
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Tyr Ser Ser Thr Arg Asn Ser
1               5

<210> SEQ ID NO 45
<211> LENGTH: 7
<212> TYPE: PRT
<213> ORGANISM: Artificial Sequence
<220> FEATURE:
<223> OTHER INFORMATION: Description of Artificial Sequence: Synthetic
```

```
                        peptide

<400> SEQUENCE: 45

Ser Tyr Trp Ser Arg Thr Val
1               5

<210> SEQ ID NO 46
<211> LENGTH: 7
<212> TYPE: PRT
<213> ORGANISM: Artificial Sequence
<220> FEATURE:
<223> OTHER INFORMATION: Description of Artificial Sequence: Synthetic
        peptide

<400> SEQUENCE: 46

Gln Ser Ser Asp Leu Ser Arg
1               5

<210> SEQ ID NO 47
<211> LENGTH: 7
<212> TYPE: PRT
<213> ORGANISM: Artificial Sequence
<220> FEATURE:
<223> OTHER INFORMATION: Description of Artificial Sequence: Synthetic
        peptide

<400> SEQUENCE: 47

Arg Thr Asp Ala Leu Arg Gly
1               5

<210> SEQ ID NO 48
<211> LENGTH: 7
<212> TYPE: PRT
<213> ORGANISM: Artificial Sequence
<220> FEATURE:
<223> OTHER INFORMATION: Description of Artificial Sequence: Synthetic
        peptide

<400> SEQUENCE: 48

Gln Lys Ser Pro Leu Asn Thr
1               5

<210> SEQ ID NO 49
<211> LENGTH: 7
<212> TYPE: PRT
<213> ORGANISM: Artificial Sequence
<220> FEATURE:
<223> OTHER INFORMATION: Description of Artificial Sequence: Synthetic
        peptide

<400> SEQUENCE: 49

Gln Ala Glu Asn Leu Lys Ser
1               5

<210> SEQ ID NO 50
<211> LENGTH: 7
<212> TYPE: PRT
<213> ORGANISM: Artificial Sequence
<220> FEATURE:
<223> OTHER INFORMATION: Description of Artificial Sequence: Synthetic
        peptide

<400> SEQUENCE: 50

Arg Arg Ala His Leu Asn Gln
1               5

<210> SEQ ID NO 51
```

```
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Ser Asp Thr Asn Arg Phe Lys
1               5

<210> SEQ ID NO 52
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Asp Arg Ser Ala Leu Ser Arg
1               5

<210> SEQ ID NO 53
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Thr Ser Ser Asn Arg Lys Thr
1               5

<210> SEQ ID NO 54
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Arg Ser Asp His Leu Ser Arg
1               5

<210> SEQ ID NO 55
<211> LENGTH: 28
<212> TYPE: DNA
<213> ORGANISM: Mus sp.

<400> SEQUENCE: 55
ctgaaggtgg caatggttcc tctctgct                                           28

<210> SEQ ID NO 56
<211> LENGTH: 28
<212> TYPE: DNA
<213> ORGANISM: Mus sp.

<400> SEQUENCE: 56
tttcctgtaa cgatcgggaa ctggcatc                                           28

<210> SEQ ID NO 57
<211> LENGTH: 28
<212> TYPE: DNA
<213> ORGANISM: Mus sp.
```

```
<400> SEQUENCE: 57
aagatgccag ttcccgatcg ttacagga                                          28

<210> SEQ ID NO 58
<211> LENGTH: 28
<212> TYPE: DNA
<213> ORGANISM: Mus sp.

<400> SEQUENCE: 58
agggagtagc ttaggtcagt gaagagaa                                          28

<210> SEQ ID NO 59
<211> LENGTH: 28
<212> TYPE: DNA
<213> ORGANISM: Mus sp.

<400> SEQUENCE: 59
acgtagagaa caacatctag attggtgg                                          28

<210> SEQ ID NO 60
<211> LENGTH: 28
<212> TYPE: DNA
<213> ORGANISM: Mus sp.

<400> SEQUENCE: 60
ctgtaataga aactgactta cgtagctt                                          28

<210> SEQ ID NO 61
<211> LENGTH: 28
<212> TYPE: DNA
<213> ORGANISM: Mus sp.

<400> SEQUENCE: 61
agggaatgtg aaatgattca gatatata                                          28

<210> SEQ ID NO 62
<211> LENGTH: 28
<212> TYPE: DNA
<213> ORGANISM: Mus sp.

<400> SEQUENCE: 62
ccatggccta acaacagttt atcttctt                                          28

<210> SEQ ID NO 63
<211> LENGTH: 28
<212> TYPE: DNA
<213> ORGANISM: Mus sp.

<400> SEQUENCE: 63
cttggctgtg taggagggga gtagcagt                                          28

<210> SEQ ID NO 64
<211> LENGTH: 28
<212> TYPE: DNA
<213> ORGANISM: Mus sp.

<400> SEQUENCE: 64
ttcctaagtt ggcagtggca tgcttaat                                          28

<210> SEQ ID NO 65
<211> LENGTH: 28
<212> TYPE: DNA
```

<213> ORGANISM: Mus sp.

<400> SEQUENCE: 65
ctttggcttt gaggattaag catgccac                28

<210> SEQ ID NO 66
<211> LENGTH: 28
<212> TYPE: DNA
<213> ORGANISM: Mus sp.

<400> SEQUENCE: 66
acttggctcc aagatttata gccttaaa                28

<210> SEQ ID NO 67
<211> LENGTH: 28
<212> TYPE: DNA
<213> ORGANISM: Mus sp.

<400> SEQUENCE: 67
caggaaagta agataggaag gaatgtga                28

<210> SEQ ID NO 68
<211> LENGTH: 28
<212> TYPE: DNA
<213> ORGANISM: Mus sp.

<400> SEQUENCE: 68
ctggggtaaa tgtctccttg ctcttctt                28

<210> SEQ ID NO 69
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 69
cctgctcgac catgctatac t                21

<210> SEQ ID NO 70
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 70
caggcctttg aaatgttgtt c                21

<210> SEQ ID NO 71
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 71
aagtgcaaag cctttcagga                20

<210> SEQ ID NO 72
<211> LENGTH: 20
<212> TYPE: DNA

```
<213> ORGANISM: Artificial Sequence
<220> FEATURE:
<223> OTHER INFORMATION: Description of Artificial Sequence: Synthetic
      primer

<400> SEQUENCE: 72
gtgtccttgt cagcagcctt                                              20

<210> SEQ ID NO 73
<211> LENGTH: 349
<212> TYPE: DNA
<213> ORGANISM: Macaca mulatta

<400> SEQUENCE: 73
ttgaagaagt atattagtgc taatttccct ccgtttgtcc tagcttttct cttctgtcaa    60
tcccacgagc ctttggcaca atgaagtggg taacctttat ttcccttctc tttctcttta   120
gctcagctta ttcaggggt gtgtttcgtc gagatacacg taagaaatcc attttttctat   180 tgttcaactt ttattctatt ttcctagtaa aataaagttt tagtaaactc tgcatcttta   240
aagaattgtt ttgtcatgta tttctaaaat gggatagtat tttgtatttg tgaagtctta   300
caaagttatc ttattaataa aattcaaaca tcctaggtaa aataaaagg              349

<210> SEQ ID NO 74
<211> LENGTH: 349
<212> TYPE: DNA
<213> ORGANISM: Callithrix jacchus

<400> SEQUENCE: 74
ttaaagaagt atattagtgc taatttctct ccatttgtcc tagcttttct cttctgtcaa    60
ccccacgagc ctttggcaca atgaagtggg taacctttat ttcccttctc tttctcttta   120
gctcagctta ttcaggggt gtgtttcgtc gagatgcacg taagaatttc attttttctat   180 tgttcaactt ttattctttt tcctagtaac ataaagtttt agtaaactgc atttttaaag   240
aattattttg gcatttattt ctaaaatggg atgcatttg tatttgtgaa gtcttacaag   300
gttatattat taataaattt caaacatcct aggtaaaaga aaaagaggg              349

<210> SEQ ID NO 75
<211> LENGTH: 395
<212> TYPE: DNA
<213> ORGANISM: Canis familiaris

<400> SEQUENCE: 75
ttaaagaagt atattagtgt gaatttccct ctgttcgtcc tacctttttct cttctatcaa   60 ccccacaagc ctttggcaca atgaagtggg taactttttat ttccctttttc tttctcttta 120 gctctgctta ttcaggggc ttggttcgac gagaagcatg taagaattct attttccctat  180 tgttcaactt tatttttagtt tcctagtaaa ataaattttt ttttgtaaaa gaaatttttta 240 gaaaccctg catctttcca gaattgcttt tctttagcat ttatttctag acagtgatga   300 tatttttatat ttgtgacccc tttgaaagtt attattttttt aagatctgcg agagagcatg  360
aagtggtggg ggcagggaga gggagaagca gggag                            395

<210> SEQ ID NO 76
<211> LENGTH: 364
<212> TYPE: DNA
<213> ORGANISM: Mus musculus

<400> SEQUENCE: 76
```

```
ttaaagaagt atattagagc gagtctttct gcacacagat caccttttcct atcaaccccca    60 ctagcctctg gcaaaatgaa gtgggtaacc tttctcctcc tcctcttcgt ctccggctct   120 gcttttcca ggggtgtgtt tcgccgagaa gcacgtaaga gttttatgtt ttttcatctc   180
tgcttgtatt tttctagtaa tggaagcctg gtattttaaa atagttaaat tttcctttag   240
tgctgatttc tagattatta ttactgttgt tgttgttatt attgtcatta tttgcatctg   300 agaacccta ggtggttata ttattgatat attttttggta tctttgatga caataatggg   360
ggat                                                                364

<210> SEQ ID NO 77
<211> LENGTH: 521
<212> TYPE: DNA
<213> ORGANISM: Macaca mulatta

<400> SEQUENCE: 77
tcagaattgt ttagtggctg taatttttctt tgcccacta aggaaagtgc aaagtaactt    60
agagtgactt aaacttcaca gaacagagtt gaagattgaa ttcataactg tccctaagac   120
ctatccattg cactatgctt tatttaaaag ccacaaaacc tgtgctgttg atctcataaa   180
tagaacttgt atttatattt actttcattt tagtctgtct tctcagttgc tgttgatata   240
cactaaaaga gtattagata ttacctgttt gaatataaaa ctataaatat ctaataattt   300
taaaaatagt attcttgata attgaattat tcctctgttt aaaggcagaa gaaataattc   360
accattatcc tgacttttc tgtaggaatc agagcccaat attttgaaac aaatgcataa   420
tctaagtcaa atgaaagaa atataaaag taacattatt acttcttgtt ttcttcagta   480
tttaacaacc cttttttttc tccccttccc cagacaagag t                      521

<210> SEQ ID NO 78
<211> LENGTH: 523
<212> TYPE: DNA
<213> ORGANISM: Callithrix jacchus

<400> SEQUENCE: 78
tcagaattgt ttagtggcta atttctttt gaatatgtag aaaagtgcag agtgacttag    60
acagaatgac ttaaacttca cagaatagag ttgaagattg aattcataac tatcccaaag   120
acctattcat tgcactatgc ttatttaaa aatcacaaaa cctgtgctgt tgatctaata   180
aatagaactt gtatttatat ttactttcat ttcagcctgt cttctcagta gttgttaata   240
gacactgaga gtattagatg atatctaagt ctgaatataa agctataaat atttaataat   300
taaaaaatta gtattattgg taattgaatt attcttctgt ttaaaggcag gagaaataat   360
tcagcatcat cctgagtttt tctgtaggaa tcagagtcca atattttgaa gtaaatgcat   420
aatctaagtc aaatggaaaa aaatataaaa agtaattta ttacttgttt tcctcagtat   480
ttcacaacct ttttttctc tctctctctg cccagacaaa agt                     523

<210> SEQ ID NO 79
<211> LENGTH: 587
<212> TYPE: DNA
<213> ORGANISM: Canis familiaris

<400> SEQUENCE: 79
cctgaggaag ttatcttatt aatatatttc caacatccta tgtgaaaaaa aatagaatta    60
tttagtagct gtaactacct tctgtacatg aaggagctta gagtgcctta aacttcacag   120
aatatagttg acgttagaat tgatagctcc gtattcccaa aggctattgc actgtgattt   180
```

```
atgggaaaaa aaaaacccac aaacctgtgt tgctaatctt gtaaatagaa cttgtattta    240
tatttttcat ttcagtctgt cctctcagca gctgttaata gacattacaa gagcattaga    300
tcttatccaa gtttgaatat aaggctacaa atatttaatg attttaatga ttttttgaaa    360
tcatatcatt cgtgattgaa taacttatct gttttaatgc agaatgaata cttcatcatt    420
ctaagatttt tctgtcagga taagaggcaa atattttgga gcaaacgaat acttaagtca    480
tgtggagaga aacacaaaga gtaacatcat aacgaggtca ttttcttcag aatgtaacaa    540
atctgtttta tttttatttt tttctttttt cctctccaga taagagt                587
```

<210> SEQ ID NO 80
<211> LENGTH: 502
<212> TYPE: DNA
<213> ORGANISM: Rattus norvegicus

<400> SEQUENCE: 80

```
tttgaaagat tagttttaaa atttctttta attaaaataa aatgctagct agaatgattt     60
gaactatgtc agatacagct gaactcacta gtttcaaagg gcctgcctgc tctacctagc    120
tatactaaac acgcatagcc tgtattagta atttacgaa tggagtttcc acttatattt     180
acttttattt cttatttact attgccttag tagacattta caaacatgac tgaaacattc    240
cgtcttgggg ttgaatgcaa agttataagc acttaatgag tctttaaaaa taatagtttc    300
ggtgaaagaa taaaactctg aatgtagtcg aaaggaattg ccatcttccg attttcctgt    360
agcgattgga ggctgggaac ttcagggaat agtttaagtg agtgaagaga agggtgaaaa    420
gcagcgtgtt gtaatttgat gtcttcaata tttaaatatg ttttgtggtt tttttctctc    480
ccccattccc acagacaaga gt                                             502
```

<210> SEQ ID NO 81
<211> LENGTH: 505
<212> TYPE: DNA
<213> ORGANISM: Mus musculus

<400> SEQUENCE: 81

```
tttgaaagct tagcttaaa tttcttttaa ttaaaaaaa atgctaggca gaatgactca      60
aattacgttg gatacagttg aatttattac ggtctcatag ggcctgcctg ctcgaccatg    120
ctatactaaa aattaaaagt gtgtgttact aattttataa atggagtttc catttatatt    180
tacctttatt tcttatttac cattgtctta gtagatattt acaaacatga cagaaacact    240
aaatcttgag tttgaatgca cagatataaa cacttaacgg ttttaaaaaa taataatgtt    300
ggtgaaaaaa tataactttg agtgtagcag agaggaacca ttgccacctt cagattttcc    360
tgtaacgatc gggaactggc atcttcaggg agtagcttag gtcagtgaag agaagaacaa    420
aaagcagcat attacagtta gttgtcttca tcaatcttta aatatgttgt gtggtttttc    480
tctccctgtt tccacagaca agagt                                          505
```

<210> SEQ ID NO 82
<211> LENGTH: 480
<212> TYPE: DNA
<213> ORGANISM: Homo sapiens

<400> SEQUENCE: 82

```
gtcgagatgc acgtaagaaa tccatttttc tattgttcaa cttttattct attttcccag     60
taaaataaag tttagtaaaa ctctgcatct ttaaagaatt attttggcat ttatttctaa    120
```

```
aatggcatag tattttgtat ttgtgaagtc ttacaaggtt atcttattaa taaaattcaa    180
acatcctagg taaaaaaaaa aaaggtcag  aattgtttag tgactgtaat tttcttttgc    240
gcactaagga agtgcaaag  taacttagag tgactgaaac ttcacagaat agggttgaag    300
attgaattca taactatccc aaagacctat ccattgcact atgctttatt taaaaaccac    360
aaaacctgtg ctgttgatct cataaataga acttgtattt atatttattt tcattttagt    420
atggctattg agtacttcaa atatgacaag tgcaactgag aaacaaaaac ttaaattgta    480
```

<210> SEQ ID NO 83
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Gln Arg Ser Asn Leu Asp Ser
1               5

<210> SEQ ID NO 84
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Tyr His Trp Tyr Leu Lys Lys
1               5

<210> SEQ ID NO 85
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Arg Ser Asp Asp Leu Ser Val
1               5

<210> SEQ ID NO 86
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Thr Ser Ser Asn Arg Thr Lys
1               5

<210> SEQ ID NO 87
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

```
Gln Tyr Thr His Leu Val Ala
1               5

<210> SEQ ID NO 88
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Arg Ser Asp His Leu Ser Thr
1               5

<210> SEQ ID NO 89
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Arg Ser Asp Ala Arg Thr Thr
1               5

<210> SEQ ID NO 90
<211> LENGTH: 28
<212> TYPE: DNA
<213> ORGANISM: Canis sp.

<400> SEQUENCE: 90
agtattcgtt tgctccaaaa tatttgcc                                      28

<210> SEQ ID NO 91
<211> LENGTH: 28
<212> TYPE: DNA
<213> ORGANISM: Canis sp.

<400> SEQUENCE: 91
aagtcatgtg gagagaaaca caaagagt                                      28

<210> SEQ ID NO 92
<211> LENGTH: 60
<212> TYPE: DNA
<213> ORGANISM: Homo sapiens

<400> SEQUENCE: 92
attgaattca taactatccc aaagacctat ccattgcact atgctttatt taaaaaccac   60

<210> SEQ ID NO 93
<211> LENGTH: 60
<212> TYPE: DNA
<213> ORGANISM: Macaca mulatta

<400> SEQUENCE: 93
attgaattca taactgtccc taagacctat ccattgcact atgctttatt taaaagccac   60

<210> SEQ ID NO 94
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 94

His Leu Gly Asn Leu Lys Thr
1               5

<210> SEQ ID NO 95
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Leu Lys His His Leu Thr Asp
1               5

<210> SEQ ID NO 96
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Arg Leu Asp Asn Arg Thr Ala
1               5

<210> SEQ ID NO 97
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Leu Met Gln Asn Arg Asn Gln
1               5

<210> SEQ ID NO 98
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Arg Ser Asp His Leu Thr Thr
1               5

<210> SEQ ID NO 99
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Gln Arg Ser Asn Leu Val Arg
1               5

<210> SEQ ID NO 100
<211> LENGTH: 7
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

Leu Arg Met Asn Leu Thr Lys
1               5

<210> SEQ ID NO 101
<211> LENGTH: 28
<212> TYPE: DNA
<213> ORGANISM: Macaca mulatta

<400> SEQUENCE: 101
ttagggacag ttatgaattc aatcttca                                        28

<210> SEQ ID NO 102
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 102
gttgccagcc atctgttgtt t                                               21

<210> SEQ ID NO 103
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 103
gacagtggga gtggcacctt                                                 20

<210> SEQ ID NO 104
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 104
ctcccccgtg ccttccttga cc                                              22

<210> SEQ ID NO 105
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

Leu Arg His Asn Leu Arg Ala
1               5

<210> SEQ ID NO 106
<211> LENGTH: 7
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 106

Asp Gln Ser Asn Leu Arg Ala
1               5

<210> SEQ ID NO 107
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

Arg Pro Tyr Thr Leu Arg Leu
1               5

<210> SEQ ID NO 108
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108

His Arg Ser Asn Leu Asn Lys
1               5

<210> SEQ ID NO 109
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 109

Leu Lys Trp Asn Leu Arg Thr
1               5

<210> SEQ ID NO 110
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 110

Trp Lys Trp Asn Leu Arg Ala
1               5

<210> SEQ ID NO 111
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 111

Leu Lys Gln His Leu Asn Glu
1               5
```

<210> SEQ ID NO 112
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 112

Arg Arg Tyr Tyr Leu Arg Leu
1               5

<210> SEQ ID NO 113
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 113

Arg Arg Asp Trp Arg Arg Asp
1               5

<210> SEQ ID NO 114
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 114

Asp Lys Ser Tyr Leu Arg Pro
1               5

<210> SEQ ID NO 115
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 115

His Arg Ser Ala Arg Lys Arg
1               5

<210> SEQ ID NO 116
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 116

Trp Arg Ser Ser Leu Lys Thr
1               5

<210> SEQ ID NO 117
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 117

Gln Ser Gly Asn Leu His Val
1               5

<210> SEQ ID NO 118
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 118

Gln Ser Ala His Arg Lys Asn
1               5

<210> SEQ ID NO 119
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 119

Ser Thr Ala Ala Leu Ser Tyr
1               5

<210> SEQ ID NO 120
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 120

Thr Ser Gly Ser Leu Ser Arg
1               5

<210> SEQ ID NO 121
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 121

Gln Arg Ser Asn Leu Asn Ile
1               5

<210> SEQ ID NO 122
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 122

Gln Arg Thr His Leu Thr Gln
1               5

<210> SEQ ID NO 123
<211> LENGTH: 7
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 123

Asp Arg Ser Asn Leu Thr Arg
1               5

<210> SEQ ID NO 124
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 124

Gln Lys Val Asn Arg Ala Gly
1               5

<210> SEQ ID NO 125
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 125

Gln Asn Ala Asn Arg Ile Thr
1               5

<210> SEQ ID NO 126
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 126

Gln Ser Ala His Arg Ile Thr
1               5

<210> SEQ ID NO 127
<211> LENGTH: 28
<212> TYPE: DNA
<213> ORGANISM: Homo sapiens

<400> SEQUENCE: 127
cctatccatt gcactatgct ttatttaa                                    28

<210> SEQ ID NO 128
<211> LENGTH: 28
<212> TYPE: DNA
<213> ORGANISM: Homo sapiens

<400> SEQUENCE: 128
tttgggatag ttatgaattc aatcttca                                    28

<210> SEQ ID NO 129
<211> LENGTH: 28
<212> TYPE: DNA
<213> ORGANISM: Homo sapiens

<400> SEQUENCE: 129
```

```
cctgtgctgt tgatctcata aatagaac                                          28

<210> SEQ ID NO 130
<211> LENGTH: 28
<212> TYPE: DNA
<213> ORGANISM: Homo sapiens

<400> SEQUENCE: 130
ttgtggtttt taaataaagc atagtgca                                          28

<210> SEQ ID NO 131
<211> LENGTH: 28
<212> TYPE: DNA
<213> ORGANISM: Homo sapiens

<400> SEQUENCE: 131
accaagaaga cagactaaaa tgaaaata                                          28

<210> SEQ ID NO 132
<211> LENGTH: 28
<212> TYPE: DNA
<213> ORGANISM: Homo sapiens

<400> SEQUENCE: 132
ctgttgatag acactaaaag agtattag                                          28

<210> SEQ ID NO 133
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 133
gttgaagatt gaattcata                                                    19

<210> SEQ ID NO 134
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 134
gtgcaatgga taggtcttt                                                    19

<210> SEQ ID NO 135
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 135
atagtgcaat ggataggtc                                                    19

<210> SEQ ID NO 136
<211> LENGTH: 19
<212> TYPE: DNA
<213> ORGANISM: Artificial Sequence
<220> FEATURE:
<223> OTHER INFORMATION: Description of Artificial Sequence: Synthetic
```

-continued oligonucleotide

<400> SEQUENCE: 136
attgaattca taactatcc                                                  19

<210> SEQ ID NO 137
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 137
attgaattca taactatccc a                                                21

<210> SEQ ID NO 138
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 138
ataaagcata gtgcaatgga t                                                21

<210> SEQ ID NO 139
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 139
ataaagcata gtgcaatgg                                                   19

<210> SEQ ID NO 140
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 140
ctatgcttta tttaaaaac                                                   19

<210> SEQ ID NO 141
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 141
ctatgcttta tttaaaaacc a                                                21

<210> SEQ ID NO 142
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 142
atttatgaga tcaacagcac a                                              21

<210> SEQ ID NO 143
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 143
ttcattttag tctgtcttct t                                              21

<210> SEQ ID NO 144
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 144
attttagtct gtcttcttg                                                 19

<210> SEQ ID NO 145
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 145
ctaatactct tttagtgtct                                                20

<210> SEQ ID NO 146
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 146
atctaatact cttttagtgt c                                              21

<210> SEQ ID NO 147
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 147
ataattgaac atcatcctg                                                 19

<210> SEQ ID NO 148
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
```

<400> SEQUENCE: 148
ataattgaac atcatcctga g                                            21

<210> SEQ ID NO 149
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 149
atattgggct ctgattccta c                                            21

<210> SEQ ID NO 150
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 150
atattgggct ctgattcct                                               19

<210> SEQ ID NO 151
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 151
tttttctgta ggaatcagag                                              20

<210> SEQ ID NO 152
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 152
ttatgcattt gtttcaaaa                                               19

<210> SEQ ID NO 153
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 153
attatgcatt tgtttcaaa                                               19

<210> SEQ ID NO 154
<211> LENGTH: 395
<212> TYPE: DNA
<213> ORGANISM: Homo sapiens

<400> SEQUENCE: 154
taaggaaagt gcaaagtaac ttagagtgac tgaaacttca cagaataggg ttgaagattg    60

```
aattcataac tatcccaaag acctatccat tgcactatgc tttatttaaa aaccacaaaa    120
cctgtgctgt tgatctcata aatagaactt gtatttatat ttattttcat tttagtctgt    180
cttcttggtt gctgttgata gacactaaaa gagtattaga tattatctaa gtttgaatat    240
aaggctataa atatttaata attttttaaaa tagtattctt ggtaattgaa ttattcttct    300
gtttaaaggc agaagaaata attgaacatc atcctgagtt tttctgtagg aatcagagcc    360
caatattttg aaacaaatgc ataatctaag tcaaa                               395
```

<210> SEQ ID NO 155
<211> LENGTH: 393
<212> TYPE: DNA
<213> ORGANISM: Macaca fascicularis

<400> SEQUENCE: 155

```
taaggaaagt gcaaagtaac ttagagtgac ttaaacttca cagaacagag ttgaagattg     60
aattcataac tgtccctaag acctatccat tgcactatgc tttatttaaa agccacaaaa    120
cctgtgctgt tgatctcata aatagaactt gtatttatat ttactttcat tttagtctgt    180
cttctcagtt gctgttgata tacactaaaa gagtattaga tattacctgt ttgaatataa    240
aactataaat atctaataat tttaaaaata gtattcttga taattgaatt attcctctgt    300
ttaaaggcag aagaaataat tcaccattat cctgactttt tctgtaggaa tcagagccca    360
atattttgaa acaaatgcat aatctaagtc aaa                                 393
```

<210> SEQ ID NO 156
<211> LENGTH: 394
<212> TYPE: DNA
<213> ORGANISM: Macaca fascicularis

<400> SEQUENCE: 156

```
taaggaaagt gcaaagtaac ttagagtgac ttaaacttca cagaacagag ttgaagattg     60
aattcataac tgtccctaag acctatccat tgcactatgc tttatttaaa agccacaaaa    120
cctgtgctgt tgatctcata aatagaactt gtatttatat ttactttcat tttagtctgt    180
cttctcagtt gctgttgata tacactaaaa gagtattaga tattacctgt ttgaatataa    240
aactataaat atctaataat tttaaaaata gtattcttga taattgaatt attcctctgt    300
ttaaaggcag taagaaataa ttcaccatta tcctgactttt ttctgtagga atcagagccc    360
aatattttga aacaaatgca taatctaagt caaa                                394
```

<210> SEQ ID NO 157
<211> LENGTH: 393
<212> TYPE: DNA
<213> ORGANISM: Macaca mulatta

<400> SEQUENCE: 157

```
taaggaaagt gcaaagtaac ttagagtgac ttaaacttca cagaacagag ttgaagattg     60
aattcataac tgtccctaag acctatccat tgcactatgc tttatttaaa agccacaaaa    120
cctgtgctgt tgatctcata aatagaactt gtatttatat ttactttcat tttagtctgt    180
cttctcagtt gctgttgata tacactaaaa gagtattaga tattacctgt ttgaatataa    240
aactataaat atctaataat tttaaaaata gtattcttga taattgaatt attcctctgt    300
ttaaaggcag aagaaataat tcaccattat cctgactttt tctgtaggaa tcagagccca    360
atattttgaa acaaatgcat aatctaagtc aaa                                 393
```

<210> SEQ ID NO 158
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 158
ctatttatga gatcaacagc a                                              21

<210> SEQ ID NO 159
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 159
tttttctgta ggaatcaga                                                 19

<210> SEQ ID NO 160
<211> LENGTH: 353
<212> TYPE: DNA
<213> ORGANISM: Homo sapiens

<400> SEQUENCE: 160
ttaaagaagt atattagtgc taatttccct ccgtttgtcc tagcttttct cttctgtcaa     60
ccccacacgc ctttggcaca atgaagtggg taacctttat ttccttctt tttctcttta    120 gctcggctta ttccaggggt gtgtttcgtc gagatgcacg taagaaatcc attttttctat  180 tgttcaactt ttattctatt tcccagtaa aataaagttt tagtaaactc tgcatcttta    240
aagaattatt ttggcattta tttctaaaat ggcatagtat tttgtatttg tgaagtctta   300
caaggttatc ttattaataa aattcaaaca tcctaggtaa aaaaaaaaaa agg           353

<210> SEQ ID NO 161
<211> LENGTH: 523
<212> TYPE: DNA
<213> ORGANISM: Homo sapiens

<400> SEQUENCE: 161
tcagaattgt ttagtgactg taattttctt ttgcgcacta aggaaagtgc aaagtaactt     60
agagtgactg aaacttcaca gaatagggtt gaagattgaa ttcataacta tcccaaagac   120
ctatccattg cactatgctt tatttaaaaa ccacaaaacc tgtgctgttg atctcataaa   180
tagaacttgt atttatattt attttcattt tagtctgtct tcttggttgc tgttgataga   240
cactaaaaga gtattagata ttatctaagt ttgaatataa ggctataaat atttaataat   300
ttttaaaata gtattcttgg taattgaatt attcttctgt ttaaaggcag aagaaataat   360
tgaacatcat cctgagtttt tctgtaggaa tcagagccca atattttgaa acaaatgcat   420
aatctaagtc aaatggaaag aaatatataaa agtaacatta ttacttcttg ttttcttcag  480
tatttaacaa tccttttttt tcttcccttg cccagacaag agt                     523

<210> SEQ ID NO 162
<211> LENGTH: 9
<212> TYPE: PRT
<213> ORGANISM: Unknown
<220> FEATURE:
<223> OTHER INFORMATION: Description of Unknown: 'LAGLIDADG' family
      peptide motif sequence

```
<400> SEQUENCE: 162

Leu Ala Gly Leu Ile Asp Ala Asp Gly
1               5

<210> SEQ ID NO 163
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 163

Asn Arg His His Leu Lys Ser
1               5

<210> SEQ ID NO 164
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 164
gttgaagatt gaattcataa c                                              21

<210> SEQ ID NO 165
<211> LENGTH: 364
<212> TYPE: DNA
<213> ORGANISM: Rattus norvegicus

<400> SEQUENCE: 165
ttagagaagt atattagagc gagtttctct gcacacagac cacctttcct gtcaacccca    60
ctagcctctg gcacaatgaa gtgggtaacc tttctcctcc tcctcttcat ctccggttct   120
gccttttcca ggggtgtgtt tcgccgagaa gcacgtaagc attctatgtt ttctcatctc   180
tacttttatt tttcgtagta acggaagcca ggtatttcaa aattacttaa attttccttt   240
ggtgatgatt aatatcacca ttattattat tattattatt attattatta catttgcatc   300
tgagaatcct tatgtggtta tattaatgta ttttagataa ctccgatgac aataatgggg   360
ggac                                                                364
```